US007435755B2

(12) United States Patent
Konopleva et al.

(10) Patent No.: US 7,435,755 B2
(45) Date of Patent: Oct. 14, 2008

(54) CDDO-COMPOUNDS AND COMBINATION THERAPIES THEREOF

(75) Inventors: Marina Konopleva, Houston, TX (US); Michael Andreeff, Houston, TX (US); Michael B. Sporn, Tunbridge, VT (US)

(73) Assignees: The Trustees of Dartmouth College, Hanover, NH (US); Board of Regents, The University of Texas System, Austin, TX (US)

( * ) Notice: Subject to any disclaimer, the term of this patent is extended or adjusted under 35 U.S.C. 154(b) by 961 days.

(21) Appl. No.: 09/998,009

(22) Filed: Nov. 28, 2001

(65) Prior Publication Data

US 2003/0119732 A1    Jun. 26, 2003

Related U.S. Application Data

(60) Provisional application No. 60/253,673, filed on Nov. 28, 2000.

(51) Int. Cl.
*A61K 31/21* (2006.01)
(52) U.S. Cl. ...................................... 514/510
(58) Field of Classification Search ................. 514/510, 514/569, 310
See application file for complete search history.

(56) References Cited

U.S. PATENT DOCUMENTS

| 4,395,423 | A | 7/1983 | Neumann | 424/304 |
| 5,064,823 | A | 11/1991 | Lee et al. | 514/198 |
| 5,603,958 | A | 2/1997 | Morein et al. | 424/489 |
| 6,326,507 | B1 | 12/2001 | Gribble et al. | 558/415 |
| 6,485,756 | B1 | 11/2002 | Aust et al. | 424/725 |
| 2002/0042535 | A1 | 4/2002 | Gribble et al. | 558/429 |

FOREIGN PATENT DOCUMENTS

WO    WO 99/65478    12/1999

OTHER PUBLICATIONS

Elstner et al. Ligands for peroxisome proliferator-activated receptor [gamma] and retinoic acid receptor inhibit growth and induce apoptosis of human breast cancer cells in vitro and in BNX mice. Proc. Natl. Acad. Sci. USA, 1998, v. 95, pp. 8806-8811.*
Al-alami et al., Divergent effect of taxol on proliferation, apoptosis and nitric oxide production in MHH225 CD34 positive and U937 CD34 negative human leukaemia cells. Leukemia Research, 1998, v. 22, pp. 939-945.*
Lieu et al. Dual cytotoxic mechanisms of submicromolar taxol on human leukemia HL-60 cells. Biochemical Pharmacology, 1997, v. 53, pp. 1587-1596.*
Kurbacher et al. Ascorbic acid (vitamin C) improves the antineoplastic activity of doxorubicin, cisplatin, and paclitaxel in human breast carcinoma cells in vitro. Cancer Letters, 1996, v. 103, pp. 183-189.*
Gura et al. Systems for identifying new drugs are often faulty. Science, 1997, 278:1041-1042.*

Johnson et al. Relationships between drug activity in NCI preclinical in vitro and in vivo models and early clinical trials. British J. of Cancer, 2001, 84(10):1424-1431.*
Agarwal and Mehta, "Possible involvement of Bcl-2 pathway in retinoid X receptor alpha-induced apoptosis of HL-60 cells," *Biochem Biophys Res Common*, 230(2):251-253, 1997.
Andreeff et al., "Expression of bcl-2-related genes in normal and AML progenitors: Changes induced by chemotherapy and cationic acid," *Leukemia*, 13:1881-1892, 1999.
Andreeff, "Acute myeloid leukemia," In: *Cancer Treatment*, Haskell (Ed.), W. B. Saunders, 911-922, 1995.
Beran et al., "Topotecan and cytarabine is an active combination regimen in myelodysplastic syndromes and chronic myelomonocytic leukemia," *J. Clinical Oncology*, 17(9):2819-2830, 1999.
Carter et al., "Expression of survivin, a member of the inhibitor of apoptosis (IAP) family of caspase inhibitors is expressed in AML and regulated by cytokines and ATRA," *Blood*, 94(Suppl 1):479a, Abstract # 2142, 1999.
Castaigne et al., "All-trans retinoic acid as a differentiation therapy for acute promyelocytic leukemia," *Blood*, 76(9):1704-1709, 1990.
Drach et al., "Induction of differentiation in myeloid leukemia cell lines and acute promyelocytic leukemia cells by liposomal all-trans-retinoic acid," *Cancer Research*, 53:2100-2104, 1993.
Engel et al., "Quantitation of minimal residual disease in acute myelogenous leukemia and myelodysplastic syndromes in complete remission by molecular cytogenetics of progenitor cells," *Leukemia*, 13:568-577, 1999.
Estey et al., "Molecular remissions induced by liposomal-encapsulated all-trans retinoic acid in newly diagnosed acute promyelocytic leukemia," *Blood*, 94:2230-2235, 1999.
Estey et al., "Randomized phase II study of fludarabine+cytosine arabinoside+idarubicin+all-trans retinoic acid+granulocyte-colony stimulating factor in poor prognosis newly diagnosed acute myeloid leukemia and myelodysplastic syndrom," *Blood*, 93(8):2478-2484, 1998.
Kim et al., "Capasase-3 activation is involved in apoptosis induced by a synthetic triterpenoid in Non-small cell lung cancer (NSCLC) cells," *Proc. Amer. Assoc. Cancer Res.*, 41:770, Abstract #4894, 2000.
Konopleva and Andreeff, "Regulatory pathways in programmed cell death," *Cancer Mol Biol.*, 6:1229-1260, 1999.
Konopleva et al., "Apoptosis: molecules and mechanisms," *Adv Exp Med Biol*, 457:217-236, 1998.
Konopleva et al., "Engraftment potential of AML progenitors into NOD/scid mice is dependent on baseline CXCR4 expression," *Blood*, 94(Suppl 1):166b, Abstract #3916, 1999.

(Continued)

*Primary Examiner*—Ardin Marschel
*Assistant Examiner*—James D Anderson
(74) *Attorney, Agent, or Firm*—Fulbright & Jaworski

(57) ABSTRACT

CDDO-compounds in combination with other chemotherapeutic agents induce and potentiate cytotoxicity and apoptosis in cancer cell. One class of chemotherapeutic agents include retinoids. Cancer therapies based on these combination therapies are provided. Also provided are methods to treat graft versus host diseases using the CDDO compounds.

51 Claims, 35 Drawing Sheets

OTHER PUBLICATIONS

Konopleva et al., "Novel synthetic triterpenoid, CDDO, and its methyl ester: Potent antiproliferative, proapoptotic and differentiating agents in AML," *Blood*, 94(Suppl 1):479a, Abstraact #2140, 1999.

Konopleva et al., "Novel triterpenoid CDD0-Me is a potent inducer of apoptosis and differentiation in acute myelogenous leukemia," *Blood*, 99(1):326-335, 2002.

Konopleva et al., "PPARγ nuclear receptor as a novel therapeutic target in AML," *Blood*, 96(11):460a, Abstract #1982, 2000.

Kornblau et al., "Phase I study of mitoxantrone plus etoposide with mutidrug blockage by SDZ PSC-833 in relapsed or refractory acute myelogenous leukemia," *J. Clin. Oncol.*, 15(5):1796-1802, 1997.

Mehta et al., "Activation of retinoid receptors RAR alpha and RXR alpha induces differentiation and apoptosis, respectively, in HL-60 cells," *Cell, Growth Differ*, 7(2): 179-186, 1996.

Sporn et al., "Prospects for prevention and treatment of cancer with selective PPARγ modulators (SPARMs)," *Trends in Molecular Medicine*, 7(9):395-400, 2001.

Suh et al., "A novel synthetic oleanane triterpenoid, 2-cyano-3, 12-dioxoolean-1,9-dien-28-oic acid, with potent differentiating, antiproliferative, and anti-inflammatory activity," *Cancer Res.*, 59(2):336-341, 1999.

Tamm et al., "Expression and prognostic significance of IAP-family genes in human cancers and leukemias," *Blood*, 94 (Suppl. 1):69a, Abstract # 298, 1999.

Walczak et al., "Tumoricidal activity of tumor necrosis factor-related apoptosis-inducing ligand in vivo", *Nature Medicine*,5(2):157-163, 1999.

Wang et al., "A synthetic triterpenoid, 2-cyano-3,12-dioxooleana-1,9-dien-28-oic acid (CDDO), is a ligand for the peroxisome proliferator-activated receptor gamma," *Mol.Endocrinol.*, 14(10): 1550-1556, 2000.

Warrell et al., "Differentiation therapy of acute promyelocytic leukemia with tretinoin (all-trans-retinoic acid)," *N. Engl. J. Med.*, 324(20):1385-1393, 1991.

Xie et al., "Differential expression patterns in human myeloblastic leukemia HL-60 and multidrug resistant HL-60/Dox cells analyzed by human cDNA expression array," *Blood*, 92 (Suppl 1):387a, Abstract #1600. 1998.

Ito et al., "The novel triterpenoid 2-cyano-3, 12-dioxoolean-1,9-dien-28-oic acid induces apoptosis of human myeloid leukemia cells by a caspase-8-dependent mechanism," *Cell Growth & Differentiation*, 11(5):261-267, 2000.

Konopleva et al., "Novel synthetic triterpenoid CDDO-Me: potent antiproliferative, proapoptotic and differentiating agent in AML," *Blood*, 96(11), Part 1: 121A, abstract # 522, 2000.

Ruvolo et al., "The novel triterpenoid methyl-CDDO inhibits Bcl2 phosphorylation and potently kolls U937 cells," *Blood*, 94(10), Suppl. 1, Part 1: 280A, abstract #1251, 1999.

Suh et al., "A novel synthetic oleanane triterpenoid, 2-cyano-3, 12-dioxoolean-1,9-dien-28-oic acid (CDDO), induces cell differentiaion in human myeloid leukemias," *Proceedings of the American Association for Cancer Research Annual Meeting*, 40:300, abstract # 1988, 1999.

Wang et al., "A novel synthetic triterpenoid, 2-cyano-3,12-dioxoolean-1,9-dien-28-oic acid (CDDO) induces adipocyte differentiation in 3T3-L1 cells," *Proceedings of the American Association for Cancer Research Annual Meeting*, 40:300, abstract # 1989, 1999.

Ambs et al., "p53 and vascular endothelial growth factor regulate tumor growth of NOS2-expressing human carcinoma cells," *Nat. Med.*, 4(12):1371-1376, 1998.

Andreeff et al., "PPARgamma nuclear receptor as a novel molecular target in leukemias," *2002 Keystone Symposia*, Abstract No. 501, 2002.

Bliard et al., "Glycosylation of acids under phase transfer conditions. Partial synthesis of saponins," *Tetrahedron Lett.*, 35:6107-6108, 1994.

Bogdan et al., "Contrasting mechanisms for suppression of macrophage cytokine release by transforming growth factor-beta and interleukin-10," *J. Biol. Chem.*, 267:23301-23308, 1992.

Bogdon and Ding, "Taxol, a microtubule-stablizing antineoplastic agent, induces expression of tumor necrosis factor α and interleukin-1 in macrophages," *J. Leukoc. Biol.*, 52(1):119-121, 1992.

Boolbol et al., "Cyclooxygenase-2 overexpression and tumor formation are blocked by sulindac in a murine model of familial adenomatous polyposis," *Cancer Res.*, 56(11):2556-2560, 1996.

Bore et al., "The anti-inflammatory triterpenoid methyl 2-cyano-3, 12-dioxoolean 1,9(11)-dien-28-oate methanol solvate hydrate," Acta Crystallorg C., 58(Pt 3):o199-o200, 2002.

Brookes et al., "The tritepenoid 2-cyano-3,12-dioxooleana-1,9-dien-28-oic acid and its derivatives elicit human lymphoid cell apoptosis through a novel pathway involving the unregulated mitochondrial permeability transition pore," *Cancer Res.*, 67:1793-1802, 2007.

Chauhan et al., "The bortezomib/proteasome inhibitor PS-341 and triterpenoid CDDO-Im induce synergistic anti-multiple myeloma (MM) activity and overcome bortezomib resistance," *Blood*, 103:3158-3166, 2004.

Chintharlapalli et al., "2-Cyano-3,12-dioxoolean-1,9-dien-28-oic acid and related compounds inhibit growth of colon cancer cells through peroxisome proliferator-activated receptor gamma-dependent and -independent pathways," *Mol. Pharmacol.*, 68:119-128, 2005.

Clinton et al., "Steroidal[3,2-c]pyrazoles. II. Androstanes, 19-norandrostanes and their unsaturated analogs," *J. Am Chem Soc.*, 83:1478-1491, 1961.

Dean et al., "Halogenolysis of methyl glycyrrhetate with lithium iodidedimethylformamide," *J. Chem. Soc.*, 6655-6659, 1965.

Dezulbe et al., "Interim results of a phase I trial with a novel orally administered synthetic triterpenoid RTA 402 (CDDO-Me) in patients with solid tumors and lymphoid malignancies," *J. Clin. Oncol.*, 2007 ASCO Annual Meeting Proceedings, 25(18S):14101, 2007.

Ding et al., "Macrophage deactivating factor and transforming growth factors-$\beta_1$,-$\beta_2$ and -$\beta_3$ inhibit induction of macrophage nitrogen oxide synthesis by IFN-$\gamma^1$," *J Immunol.*, 145(3):940-944, 1990.

Drefahl and Huneck, "Nor-olea-12-enol-17-amin und Olea-12-enol-28-amin," *Chem. Ber.*, 91:278-281, 1958.

DuBois et al., "Increased cyclooxygenase-2 levels in carcinogen-induced rat colonic tumors," *Gastroenterology*, 110:1259-1262, 1996.

Elliot et al., "The triterpenoid CDDO inhibits expression of matrix metalloproteinase-1, matrix metalloproteinase-13 and Bcl-3 in primary human chondrocytes," *Arthritis Res. Ther.*, 5:R285-R291, 2003.

Elsawa et al., "Preferential Inhibition of Malignant Cell Growth by CDDO in Waldenstrom Macroglobulinemia," *Blood*, 108(11):2528, 2006.

Favaloro, Jr. et al., "Design and synthesis of tricyclic compounds with enone functionalities in rings A and C: a novel class of highly active inhibitors of nitric oxide production in mouse macrophages," J Med Chem, 45(22):4801-4805, 2002.

Hail et al., "Evidence supporting a role for calcium in apoptosis induction by the synthetic triterpenoid 2-cyano-3,12-dioxooleana-1,9-dien-28-oic acid (CDDO)," *J. Biol. Chem.*, 279:11179-11187, 2004.

Honda et al., "A novel dicyanotriterpenoid, 2-cyano-3,12-dioxoolean-1,9(11)-dien-28-onitrile, active at picomolar concentrations for inhibition of nitric oxide production," *Bioorganic & Medicinal Chemistry Letters*, 12:1027-1030, 2002.

Honda et al., "Design and synthesis of 2-cyano-3,12-dioxoolean-1,9-dien-28-oic acid, a novel and highly active inhibitor of nitric oxide production in mouse macrophages," *Bioorg Med Chem Lett.*, 8(19):2711-2714, 1998.

Honda et al., "Efficient synthesis of (−)- and (+)-tricyclic compounds with enome functionalities in rings A and C. A novel class of orally active anti-inflammatory and cancer chemopreventive agents," Org Biomol Chem, 1:4384-4391, 2003.

Honda et al., "New enone derivatives of oleanolic acid and ursolic acid as inhibitors of nitric oxide production in mouse macrophages," *Bioorg. Med. Chem. Lett.*, 7:1623-1628, 1997.

Honda et al., "Novel synthetic oleanane and ursane tritepenoids with various enone functionalities in ring A as inhibitors of nitric oxide production in mouse macrophages," *J. Med. Chem.*, 43:1866-1877, 2000.

Honda et al., "Novel synthetic oleanane triterpenoids: a series of highly active inhibitors of nitric oxide production in mouse macrophages," *Bioorg Med Chem Lett*, 9(24):3429-3434, 1999.

Honda et al.,. "Synthetic oleanane and ursane triterpenoids with modified rings A and C: a series of highly active inhibitors of nitric oxide production in mouse macrophages," *J. Med. Chem.*, 43:4233-4246, 2000.

Huang et al., "Inhibition of skin tumorigenesis by Rosemary and its constituents carnosol and ursolic acid," *Cancer Res.*, 54:701-708, 1994.

Hyer et al., "Synthetic triterpenoids cooperate with tumor necrosis factor-related apoptosis-inducing ligand to induce apoptosis of breast cancer cells," *Cancer Res.*, 65:4799-4808, 2005.

Ikeda et al., "Induction of redox imbalance and apoptosis in multiple myeloma cells by the novel triterpenoid 2-cyano-3,12-dioxoolean-1,9-dien-28-oic acid," *Mol. Cancer Ther.*, 3:39-49, 2004.

Ikeda et al., "The novel triterpenoid CDDO and its derivatives induce apoptosis by disruption of intracellular redox balance," *Cancer Res.*, 63:5551-5558, 2003.

Johansen et al., "Pharmacology and preclinical pharmacokinetics of the triterpenoid CDDO methyl ester," *Proc. Amer. Assoc. Cancer Res.*, 44:1728, 2003.

Johnson et al., "A plan for distinguishing between some five- and six-membered ring ketones," *J. Am Chem. Soc.*, 67:1745-1754, 1945.

Kawamori et al., "Chemopreventive activity of celecoxib, as specific cyclooxygenase-2 inhibitor, against colon l carcinogenesis," *Cancer Res.*, 58(3):409-412, 1998.

Kim et al., "Identification of a novel synthetic triterpenoid, methyl-2-cyano-3,12-dioxooleana-1,9-dien-28,oate, that potently induces caspace-mediated apoptosis in human lung cancer cells," Molecular Cancer Therapeutics, 1:177-184, 2002.

Kircher, "Triterpenes, in organ pipe cactus," *Phytochemistry*, 19:2707-2712, 1980; Database Caplus on STN AN:1981:550946.

Konopleva et al., "Activation of nuclear transcription factor PPARgamma by the novel triterpenoid CDDO as targeted in breast cancer," *2002 Keystone Symposium*, Abstract No. 539, 2002.

Konopleva et al., "Mechanisms and Activity of PPARgamma-Avitve Triterpenoids CDDO and CDDO-Me in Leukemias," *Blood*, 106:2460, 2005.

Konopleva et al., "Peroxisome proliferator-activated receptor gamma and retinoid X receptor ligands are potent inducers of differentiation and apoptosis in leukemias," *Mol. Cancer Ther.*, 3:1249-1262, 2004.

Konopleva et al., "PPARgamma Ligand CDDO Induces Apoptosis in Leukemias Via Multiple Apoptosis Pathways," *Abstracts of the 44th Annual Meeting of the American Society of Hematology*, Abstract No. 2209, 2002.

Konopleva et al., "PPARgamma Ligands Are Potent Inducers of Apoptosis in Leukemias and Lymphomas," *American Society of Hematology 43rd Annual Meeting and Exposition*, Abstract No. 501, 2001.

Konopleva et al., "PPARgamma Nuclear Receptor as a Novel Molecular Target in Leukemia Therapy," *Proc. Amer. Assoc. Cancer Res.*, 43:4730, 2002.

Konopleva et al., "PPARgamma Nuclear Receptor as a Novel Therapeutic Target in AML," *Proc. Amer. Assoc. Cancer Res.*, 42:4458, 2001.

Konopleva et al., "Suppression of ERK Activation is Required for Triterpenoid Methyl-CDDO-Induced Apoptosis in AML," *Blood*, 102(11):1404, 2003.

Konopleva et al., "Synthetic triterpenoid 2-cyano-3,12-dioxooleana-1,9-dien-28-oic acid induces growth arrest in HER2-overexpressing breast cancer cells," *Mol. Cancer Ther.*, 5:317-328, 2006.

Konopleva et al., "Synthetic triterpenoid CDDO as a novel therapy for resistant breast cancer," *Proc. Amer. Assoc. Cancer Res.*, 44:2726, 2003.

Konopleva et al., "The novel triterpenoid CDDO-Me suppresses MAPK pathways and promotes p38 activation in acute myeloid leukemia cells," *Leukemia*, 19:1350-1354, 2005.

Konopleva et al., "The synthetic triterpenoid 2-cyano-3,12-dioxooleana-1,9-dien-28-oic acid induces caspase-dependent and -independent apoptosis in acute myelogenous leukemia," *Cancer Res.*, 64:7927-7935, 2004.

Konopleva et al., "Triterpenoid Methyl-CDDO Is a Potent Inducer of Apoptosis in CD34+AML Progenitor Cells Via Activation of SAPK Pathways and Inhibition of MAPK Cascades," *Blood*, 104:2533, 2004.

Kress et al., "Triterpenoids Display Single Agent Activity in a Mouse Model of CLL/SBL," *Blood*, 108(11):2530, 2006.

Kress et al., "Triterpenoids Display Single Agent Anti-tumor Activity in a Transgenic Mouse Model of Chronic Lymphocytic Leukemia and Small B Cell Lymphoma," *PLoS One*, 6(e559):1-11, 2007.

Kurinna et al., "The novel triterpenoid CDDO-Me promotes apoptosis in Gleevec-resistant chronic myeloid leukemia cells by caspase-independent mechanisms," *Proc. Amer. Assoc. Cancer Res.*, 46:2240, 2005.

Lapillone et al., "Activation of peroxisome proliferator-activated receptor gamma by a novel synthetic triterpenoid 2-cyano-3,12-dioxooleana-1,9-dien-28-oic acid induces growth arrest and apoptosis in breast cancer cells," *Cancer Res.*, 63:5926-5939, 2003.

Lemieux, "Acylglycosyl Halides. [55] tetra-O-acetyl-$\alpha$-D-glucopyranosyl bromide," *Methods Carbohydr. Chem.*, 2:221-222, 1963.

Ling et al., "The novel triterpenoid C-28 methyl ester of 2-cyano-3, 12-dioxoolen-1, 9-dien-28-oic acid inhibits metastatic murine breast tumor growth through inactivation of STAT3 signaling," *Cancer Res.*, 67:4210-4218, 2007.

Ling et al., "The novel triterpenoid CDDO-Me inhibits metastatic murine breast tumor through inhibition of Stat3 signaling," 2007 AACR Annual Meeting, Abstract No. 301, 2007.

Marnett, "Aspirin and the potential role of prostaglandins in colon cancer," *Cancer Res.*, 52(20):5575-5589, 1992.

Melichar et al., "Growth-inhibitory effect of a novel synthetic triterpenoid, 2-cyano-3,12-dioxoolean-1,9-dien-28-oic acid, on ovarian carcinoma cell lines not dependent on peroxisome proliferator-activated receptor-gamma expression," *Gynecologic Oncology*, 93:149-154, 2004.

Minns et al., "A novel triterpenoid induces transforming growth factor beta production by intraepithelial lymphocytes to prevent ileitis," *Gastroenterology*, 127:119-126, 2004.

Mix et al., "Peroxisome proliferator-activated receptor-gamma-independent repression of collagenase gene expression by 2-cyano-3,12-dioxooleana-1,9-dien-28-oic acid and prostaglandin 15-deoxy-delta(12,14) J2: a role for Smad signaling," *Mol. Pharmacol.*, 65:309-318, 2004.

Moncada et al., "Nitric oxide: physiology, pathophysiology, and pharmacology," *Pharmacol. Rev.*, 43:109-142, 1991.

Murphy et al., "Immunomodulatory Effects of the Triterpenoid CDDO after Allogeneic Bone Marrow Transplantation in Mice: Reduction of Acute Graft-Versus-Host Disease Lethality," *Blood*, 106:1316, 2005.

Nathan and Xie, "Nitric oxide synthases: roles, tolls, and controls," *Cell*, 78:915-918, 1994.

Nishino et al., "Inhibition of the tumor-promoting action of 12-O tetradecanoylphorbol-13-acetate by some oleanane-type triterpenoid compounds," *Cancer Res.*, 48:5210-5215, 1988.

Ohshima and Bartsch, "Chronic infections and inflammatory process as cancer risk factors: possible role of nitric oxide in carcinogenesis," *Mutat. Res.*, 305:253-264, 1994.

Ono et al., "A convenient procedure for esterification of carboxylic acids," *Bull. Chem. Soc. Jpn.*, 51:2401-2404, 1978.

Oshima et al., "Suppression of intestinal polyposis in Apc$^{A716}$ knockout mice by inhibition of cyclooxygenase 2 (COX-2)," *Cell*, 87:803-809, 1996.

Pedersen et al., "The triterpenoid CDDO induces apoptosis in refractory CLL B cells," *Blood*, 100:2965-2972, 2002.

Picard et al., "The triterpene resinols and related acids, part VI," *J. Chem. Soc.*, 1045-108, 1939.

Place et al., "The novel synthetic triterpenoid, CDDO-imidazolide, inhibits inflammatory response and tumor growth in vivo," *Clin. Cancer Res.*, 9:2798-2806, 2003.

Prescott and White, "Self-promotion? Intimate connections between APC and prostaglandin H synthase-2," *Cell*, 87:783-786, 1996.

Reddy et al., "Evaluation of cyclooxygenase-2 inhibitor for potential chemopreventive properties in colon carcinogenesis," *Cancer Res.*, 56(20):4566-4569, 1996.

Salvemini et al., "Endogenous nitric oxide enhances prostaglandin production in a model of renal inflammation," *J. Clin. Invest.*, 93(5):1940-1947, 1994.

Salvemini et al., "Nitric oxide activates cyclooxygenase enzymes," *Proc. Natl. Acad. Sci. USA*, 90(15):7240-7244, 1993.

Samudio et al., "2,cyano-3,12 dioxoolean-1,9 diene-28-imidazolide induces apoptosis in pancreatic cancer via redox-dependent cytoplasmic stress," *Proc. Amer. Assoc. Cancer Res.*, 46:5899, 2005.

Samudio et al., "2-Cyano-3,12-dioxooleana-1,9-dien-28-imidazolide (CDDO-Im) directly targets mitochondrial gluthatione to induce apoptosis in pancreatic cancer," *J. Biol. Chem.*, 280:36273-36282, 2005.

Samudio et al., "A novel mechanism of action of methyl-2-cyano-3,12 dioxoolean-1,9 diene-28-oate: direct permeabilization of the inner mitochondrial membrane to inhibit electron transport and induce apoptosis," *Mol. Pharmacol.*, 69:1182-1193, 2006.

Samudio et al., "A novel mechanism of action of methyl-2-cyano-3,12 dioxoolean-1,9 diene-28-oate (CDDO-Me): Direct permeabilization of the inner mitochondrial membrane to inhibit electron transport and induce apoptosis," *Proc. Am. Assoc. Cancer Res.*, 47: 4693, 2006.

Samudio et al., "A Novel Mechanism of Action of Methyl-2-cyano-3,12 dioxoolean-1,9 diene-28-oate (CDDO-Me): Direct Permeabilization of the Inner Mitochondrial Membrane to Inhibit Electron Transport and Induce Apoptosis," *Blood*, 106:4462, 2005.

Samudio et al., "The novel triterpenoid CDDOme potently synergizes with inhibition of bcl-2 function to induce apoptosis in AML via disruption of intracellular redox homeostasis," *Proc. Amer. Assoc. Cancer Res.*, 46:4955, 2005.

Scholz et al., "Sensitive and specific methods for the determination of CDDO methyl ester in mouse, rat, dog, monkey, and human plasma by LC-tandem mass spectrometry," *Proc. Amer. Assoc. Cancer Res.*, 4:6321, 2003.

Seibert and Masferrer, "Role of inducible cyclooxygenase (COX-2) in inflammation," *Receptor*, 4(1):17-23, 1994.

Sharpless et al., "Electrophilic and nucleophilic organoselenium reagents. New routes to alpha, beta-unsaturated carbonyl compounds," *J. Am. Chem. Soc.*, 95:6137, 1973.

Sheng et al., "Inhibition of human colon cancer cell growth by selective inhibition of cyclooxygenase-2," *J. Clin. Invest.*, 99(9):2254-2259, 1997.

Shishodia et al., "A synthetic triterpenoid, CDDO-Me, inhibits IkappaBalpha kinase and enhances apoptosis induced by TNF and chemotherapeutic agents through down-regulation of expression of nuclear factor kappaB-regulated gene products in human leukemic cells," *Clin. Cancer Res.*, 12:1828-1838, 2006.

Simonsen et al., "Tetracyclic hydroxy acids," In *the Terpenes*, Cambridge University, Cambridge, 5:221-285, 1957.

Sporn and Roberts, "Peptide growth factors and inflammation, tissue repair, and cancer," *J. Clin. Invest.*, 78:329-332, 1986.

Stadheim et al., "The novel triterpenoid 2-cyano-3,12-dioxooleana-1,9-dien28-oic acid (CDDO) potently enhances apoptosis induced by tumor necrosis factor in human leukemia cells," *J. Biol. Chem.*, 277:16448-16455, 2002.

Suh et al., "Novel triterpenoids suppress inducible nitric oxide synthase (iNOS) and inducible cyclooxygenase (COX-2) in mouse macrophages," *Cancer Res.*, 58:717-723, 1998.

Suh et al., "Novel triterpenoids suppress inducible nitric oxide synthase (iNOS) and inducible cyclooxygenase (COX-2)," *Proceedings of the American Association for Cancer Research Annual Meeting*, 39:266, 1998.

Suh et al., "Synthetic triterpenoids activate a pathway for apoptosis in AML cells involving downregulation of Flip and sensitization to Trail," *Leukemia*, 17:2122-2129, 2003.

Suh et al., "Synthetic triterpenoidds enhance transforming growth factor β/Smad signaling," *Cancer Res.*, 63:1371-1376, 2003.

Suh et al., "Triterpenoids CDDO and CDDO-Me Down-Regulate Flip Expression and Sensitize AML Cells to Trail-Induced Apoptosis," *American Society of Hematology 43rd Annual Meeting and Exposition*, Abstract No. 498, 2001.

Sun et al., "The synthetic triterpenoid, CDDO, suppresses alloreactive T cell responses and reduces murine early acute graft-versus-host disease mortality," *Biology of Blood and Marrow Transplantation*, 13:521-529, 2007.

Tabe et al., "Chrmoatin-Mediated Transcriptional Activation with Novel Peroxisome Proliferator—Activated Receptor gamma(PPARgamma) Ligand 2-cyano-1,9-dien-28-oic Acid (CDDO) in Acute Promyelocytic Leukemia Cells," *Abstracts of the 44th Annual Meeting of the American Society of Hematology*, Abstract No. 2191, 2002.

Takabe et al., "Synthesis of lycosyl esters of oleanolic," *Carbohydrate Research*, 76:101-108, 1979, Database Caplus and STN AN:1980:42278.

Takahashi et al., "Increased expression of inducible and endothelial constitutive nitric oxide synthase in rat colon tumors induced by azoxymethane," *Cancer Res.*, 57:1233-1237, 1997.

Tamir and Tannebaum, "The role of nitric oxide (NO) in the carcinogenic process," *Biochim. Biophys. Acta*, 1288:F31-F36, 1996.

Tsao et al., "DRIP205 co-activator overexpression enhances PPARgamma-mediated differentiation of leukemia cells by CDDO," *Proc. Amer. Assoc. Cancer Res.*, 46:1855, 2005.

Tsao et al., "Targeted Induction of Apoptosis in Leukemias by PPARgammma Ligation," *American Society of Hematology 43rd Annual Meeting and Exposition*, Abstract No. 2381, 2001.

Tsujii and DuBois, "Alteration in cellular adhesion and apoptosis in epithelial cells overexpressing prostaglandin endoperoxide synthase 2," *Cell*, 83:493-501, 1995.

Tsujii et al., "Cyclooxygenases regulates angiogenesis induced by colon cancer cells," *Cell*, 93:705-716, 1998.

Vazquez et al., "Human immunodeficiency virus type 1-induced macrophage gene expression includes the p21 gene, a target for viral regulation," *J. Virol.*, 79:4479-4491, 2005.

Wang et al., "Synthetic triterpenoid CDDO and its derivatives increase ceramides and are cytotoxic to pediatric acute lymphoblastic leukemia cell lines," *Proc. Am. Assoc. Cancer Res.*, 47: 4643, 2006.

Woodley, "Liposomes For Oral Administration of Drugs," *Crit. Rev. Therapeutic Drug Carrier System*, 2(1):1-18, 1985.

Yates et al., "Pharmacodynamic characterization of chemopreventive triterpenoids as exceptionally potent inducers of Nrf2-regulated genes," *Mol. Cancer Ther.*, 6:154-162, 2007.

Yates et al., "Potent protection against aflatoxin-induced tumorigenesis through induction of Nrf2-regulated pathways by the triterpenoid 1-[2-cyano-3,12-dioxooleana-1,9(11)-dien-28-oyl]imidazole," *Cancer Res.*, 66:2488-2494, 2006.

Zapata et al., "CDDO and CDDO-Im Reduce Tumor Burden in a Transgenic Mouse Model of CLL," *Blood*, 104:3477, 2004.

Zapata et al., "Triterpenoids show activity against leukemic cells in a transgenic mouse model of CLL," *Proc. Amer. Assoc. Cancer Res.*, 46:5179, 2005.

Zhang et al., "Synthetic triterpenoid CDDO as effective therapy for HER2-expressing resistant breast cancer," *Proc. Amer. Assoc. Cancer Res.*, Abstract No. 3799, 2004.

Zhang et al., "The novel synthetic oleanane triterpenoid CDDO (2-cyano-3, 12-dioxoolean-1, 9-dien-28-oic acid) induces apoptosis in Mycosis fungoides/Sézary syndrome cells," *J. Invest. Dermatol.*, 123:380-387, 2004.

Bollag and Holdener, "Retinoids in cancer prevention and therapy," *Annals of Oncology*, 3:513-526, 1992.

Dragnev et al., "The retinoids and cancer prevention mechanism," *The Oncologist*, 5:361-368, 2000.

* cited by examiner

A. Binding of [3H]-rosiglitazone to PPARγ (cold CDDO as a competitor)

B. CDDO transactivates PPARγ

A.

B.

100# CDDO-COMPOUNDS AND COMBINATION THERAPIES THEREOF

The present application is a continuation-in-part of U.S. patent application Ser. No. 60/253,673 filed Nov. 28, 2000. The entire text of each of the above-referenced disclosures is specifically incorporated by reference herein without disclaimer.

BACKGROUND OF THE INVENTION

1. Field of the Invention

The present invention relates generally to the fields of cancer therapy. More particularly, it concerns the use of triterpenoid CDDO-compounds, such as CDDO and/or methyl-CDDO, in combination with other chemotherapeutic agents for the treatment of cancers.

2. Description of Related Art

Cancer has become one of the leading causes of death in the western world, second only behind heart disease. Current estimates project that one person in three in the U.S. will develop cancer, and that one person in five will die from cancer. Major challenges remain to be overcome for all cancers, but this is especially true for the hematological malignancies. For example, increasing the cure rate for acute lymphoblastic leukemia (ALL), especially for middle-aged and older adults has proved difficult. Despite high rates of complete remission, many patients relapse after chemotherapy. Chronic lymphocytic leukemia (CLL), while slow-progressing and well responding initially, frequently transforms into a drug-resistant disease.

Therapeutic regimens employed in the therapy of acute myelogenous leukemia (AML) have not changed over the last three decades and usually encompass ara-C and anthracycline analogs (Andreef, 1995). Use of new drugs such as topoisomerase inhibitors, cytokines and MDR-1 blockers have failed to impact AML patient survival (Kornblau et al., 1997; Greenberg et al., 1999; Kolitz et al., 1999; Estey et al., 1998; Beran et al., 1999). The recently synthesized new and unique triterpenoid, CDDO, has anti-proliferative effects in many human tumor cell lines (Suh, 1999), induces apoptosis in non-small cell lung cancer cells (Kim et al., 2000) and has anti-proliferative and pro-apoptotic properties in several leukemias (Konopleva et al., 1999a).

Recently, the knowledge of mechanisms controlling apoptotic pathways has increased. In general, multiple signaling pathways lead from death-triggering extracellular or intracellular signals to a central control followed by an execution stage. At this stage, CED3/caspases are activated, leading to the characteristic apoptotic structural lesions accompanying cell death which include cytoplasmic and chromatin condensation and DNA fragmentation. Two regulatory pathways have been elucidated. The death receptor pathway (also called the "extrinsic" pathway), which is triggered by members of the tumor necrosis family (TNF) family, and is mediated by recruitment of the proximal regulator caspase 8 to the death receptor complex. The activated initiator caspases in turn activate the effector caspases 3, 6 and 7. The other pathway (called the "intrinsic" pathway) involves the mitochondria and is regulated by the Bcl-2 family of proteins. In this pathway, mitochondrial sequestration or release of cytochrome C (Yang et al., 1997) is followed by the activation of Apaf-1, caspase 9, and caspase 3 (for review, see (Konopleva and Andreeff, 1999; Konopleva et al., 1998; Kornblau et al., 1999).

Most chemotherapeutic agents used in the treatment of hematological malignancies cause cell killing by inducing apoptosis. Newer approaches attempt to induce apoptosis by directly targeting apoptotic pathways. For example, agents that trigger the signaling of Fas or TRAIL receptors induce the extrinsic pathway at the cell surface. Activation of the retinoic acid receptors also results in apoptosis or differentiation via down-modulation of Bcl-2 and Bcl-$X_L$ mRNA and protein levels (Andreef et al., 1999; Agarwal and Mehta, 1997). Clinical trials of several of these agents are under way. The most striking improvement in AML therapy came with the introduction of all-trans-retinoic acid (ATRA) for the treatment of acute promyelocytic leukemia (APL) (Castaigne et al., 1990). Early mortality of APL decreased, and over 90% of patients achieved complete remissions (Warrell et al., 1991) including some molecular remissions with PCR negativity (Estey et al., 1999). The peroxisome proliferator-activated receptor (PPAR) is a member of nuclear receptor family that is involved in apoptosis. Mutations of PPAR gene products are seen in several cancer types demonstrating the role of PPAR in cancer. Thus, PPAR based cancer therapies are another approach for anticancer chemotherapeutics.

Although some agents that target particular points of apoptotic pathways have anti-leukemic activities, none have proven optimal for treatment. There is still a need to systematically investigate new agents and to provide treatment regimens for hematological and other cancers.

SUMMARY OF THE INVENTION

The present invention overcomes deficiencies in the art and provides an anti-cancer therapy that involves the combination of CDDO-compounds, such as CDDO and methyl-CDDO, with other conventional chemotherapeutic compounds and/or with chemotherapeutic agents that activate different parts of apoptotic cascades.

Therefore, provided in the invention is a method for inducing cytotoxicity in a cell comprising contacting the cell with a CDDO-compound and a chemotherapeutic agent, wherein the combination of the CDDO-compound with the chemotherapeutic agent is effective in inducing cytotoxicity in the cell. The CDDO-compound is CDDO or methyl-CDDO.

In one embodiment of the method, the CDDO-compound is contacted with the cell prior to contacting the cell with the chemotherapeutic agent. In another embodiment of the method, the chemotherapeutic agent is contacted with the cell prior to contacting the cell with CDDO.

In other embodiments of the method, the cell is a cancer cell. In some aspects the cancer cell is a leukemic cell. In more specific aspects, the leukemic cell is a blood cancer cell, a myeloid leukemia cell, a monocytic leukemia cell, a myelocytic leukemia cell, a promyelocytic leukemia cell, a myeloblastic leukemia cell, a lymphocytic leukemia cell, an acute myelogenous leukemic cell, a chronic myelogenous leukemic cell, a lymphoblastic leukemia cell, a hairy cell leukemia cell.

In yet other embodiments, the cancer cell is a solid tumor cell. In specific aspects, the solid tumor cell is a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, a soft tissue cancer cell.

In one embodiment of the method, the cell is located in a human subject. In one embodiment, the CDDO-compound may be administered locally. Therefore, the compound may be administered by intratumoral injection and/or by injection into tumor vasculature.

In another embodiment of the method, the CDDO-compound may be administered systemically. In other specific aspects of this embodiment, the CDDO-compounds may be administered intravenously, intra-arterially, intra-peritoneally, orally, and/or during ex vivo bone marrow or blood stem cell purging. CDDO may be administered at dosages in the range of 5-30 mg/kg intravenously (i.v.) or 5-100 mg/kg orally. Thus, about 5, 10, 15, 20, 25, 30, 35, 40, 45, 50, 55, 60, 65, 70, 75, 80, 85, 90, 95, or about 100 mg/kg of CDDO may be administered by i.v. or may be administered orally. CDDO-Me may be administered in the range of 5-100 mg/kg intravenously or 5-100 mg/kg orally for 3-30 days. Thus, about 5, 10, 15, 20, 25, 30, 35, 40, 45, 50, 55, 60, 65, 70, 75, 80, 85, 90, 95, or 100 mg/kg of CDDO may be administered by i.v. or, 5, 10, 15, 20, 25, 30, 35, 40, 45, 50, 55, 60, 65, 70, 75, 80, 85, 90, 95, or about 100 mg/kg of CDDO may be administered orally. The skilled artisan will appreciate that these dosages are only guidelines and a physician will determine exact dosages at the time of administration factoring in other conditions such as age, sex, disease, etc. of the patient.

In one embodiment, the chemotherapeutic agent may be one or more of the listed chemotherapeutics including, doxorubicin, daunorubicin, dactinomycin, decitabine, mitoxantrone, cisplatin, procarbazine, mitomycin, carboplatin, bleomycin, etoposide, teniposide, mechlroethamine, cyclophosphamide, ifosfamide, melphalan, chlorambucil, ifosfamide, melphalan, hexamethylmelamine, thiopeta, busulfan, carmustine, lomustine, semustine, streptozocin, dacarbazine, adriamycin, 5-fluorouracil (5FU), camptothecin, actinomycin-D, hydrogen peroxide, nitrosurea, plicomycin, TRAIL, tamoxifen, taxol, transplatinum, vincristin, vinblastin, mylotarg, dolastatin-10, bryostatin and methotrexate. However, one of ordinary skill in the art will appreciate that the invention is not limited to these chemotherapeutic agents and may involve the use of other DNA damaging agents as well.

It is also contemplated that the chemotherapeutic agent can be an agent that causes immunosupression and may be a corticosteroid or tacrolimus (also known as SK506). Especially in embodiments that concern ex vivo bone marrow or blood cell purging, the bone marrow or blood may be treated with a CDDO compound, either alone or in conjunction with any other agent to eliminate any tumor, malignant or leukemic cell before treating the patient.

In yet other embodiments, the chemotherapeutic agent is a retinoid. The retinoid may be all-trans-retinoic acid (ATRA), 9-cis-retinoic acid, LG100268, LGD1069 (Targretin, bexarotene), fenretinide [N-(4-hydroxyphenyl)retinamide, 4-HPR], CD437 or any RXR- or RAR-specific retinoic acid. In one specific embodiment, the RXR-specific retinoic acid is LG100268 (Ligand Pharmaceuticals). In some embodiments, the retionids may be administered as liposomal formulations. These liposomal formulations may be administered intravenously or through other routes as well, for example a liposomal formulation of ATRA is administered a range of 10-100 mg/m$^2$/day intravenously. Thus, one may administer 10, 20, 25, 30, 35, 40, 45, 50, 55, 60, 65, 70, 75, 80, 85, 90, 95, or 100 mg/m$^2$/day of a liposomal formulation of ATRA. In one specific embodiment, 90 mg/m$^2$/day of ATRA as a liposomal formulation is intravenously. In other embodiments, the retinoids may be administered orally. For example, ATRA may be administered in the range of 10-100 mg/m$^2$/day. Thus, one may administer 10, 20, 25, 30, 35, 40, 45, 50, 55, 60, 65, 70, 75, 80, 85, 90, 95, or 100 mg/m$^2$/day of ATRA. In one specific embodiment, ATRA may be administered at 45 mg/m$^2$/day orally daily. In another example, 9-cis-Retinoid acid may be administered in the range of 20-150 mg/m$^2$ twice a day orally. Thus, one may administer 20, 25, 30, 35, 40, 45, 50, 55, 60, 65, 70, 75, 80, 85, 90, 95, 100, 105, 110, 115, 120, 125, 130, 135, 140, 145, or 150 mg/m$^2$ of 9-cis-retinoid. LG100268 may be effective in a dose range of 5-50 mg/kg. Thus, 5, 10, 15, 20, 25, 30, 35, 40, 45, to 50 mg/kg of LG100268 may be administered. LGD1069 (Targretin, bexarotene) capsules are contemplated for the topical treatment of cutaneous lesions in patients with cutaneous T-cell lymphoma (CTCL) who have refractory or resistant disease after other therapies. The dose ranges of these capusles is 300-400 mg/m$^2$/day orally. Thus, 300, 350, 400 mg/m$^2$/day may be used. LGD1069 gel at 1% may also be used for the topical treatment of cutaneous lesions in patients with CTCL (Stage (1A and 1B) who have refractory or resistant disease after other therapies; two to four times daily. Fenretinide [N-(4-hydroxyphenyl)retinamide, 4-HPR] is contemplated useful at 25-600 mg daily and the administration in some embodiments may be continuous. Thus, 25, 30, 35, 40, 45, 50, 55, 60, 65, 70, 75, 80, 85, 90, 95, 100, 120, 140, 160, 180, 200, 220, 240, 260, 280, 300, 320, 340, 360, 380, 400, 420, 440, 460, 480, 500, 520, 540, 560, 580, 600 mg may be administered daily. Of course, the skilled artisan will understand that while these dosage ranges provide useful guidelines appropriate adjustments in the dosage depending on the needs of an individual patient factoring in disease, gender, age and other general health conditions will be made at the time of administration to a patient by a trained physician.

In some embodiments of the method, the cell is contacted with the CDDO-compound a second time. In yet other embodiments, the cell may be contacted with the chemotherapeutic agent a second time. In still other aspects of this method, the CDDO-compound and the chemotherapeutic agent can be contacted with the cell at the same time.

One embodiment of the method, further comprising tumor resection in conjunction with the CDDO-compound based combination therapy. The tumor resection may occurs prior to the contacting. Thus, the contacting can comprises treating a resected tumor bed with the CDDO-compound and the chemotherapeutic agent. In other aspects, the tumor resection occurs after the contacting. In still other aspects, the contacting occurs both before and after the tumor resection.

The invention also provides methods of killing a tumor cell comprising contacting the tumor cell with a CDDO-compound and a chemotherapeutic agent, wherein the combination of said CDDO-compound with said chemotherapeutic agent, induces killing of said tumor cell.

The invention also provides methods of inducing apoptosis in a tumor cell comprising contacting said tumor cell with a CDDO-compound and a chemotherapeutic agent, wherein the combination of said CDDO-compound with said chemotherapeutic agent, induces apoptosis of said tumor cell. The CDDO-compound is CDDO or methyl-CDDO. In some embodiments of this method, the chemotherapeutic agent is a retinoid.

Also provided are methods for inducing differentiation in a tumor cell comprising contacting the tumor cell with a CDDO-compound and a chemotherapeutic agent, wherein the combination of the CDDO-compound with the chemotherapeutic agent, induces the differentiation of the tumor cell.

Further provided are methods for treating cancer in a human patient comprising administering a CDDO-compound and a chemotherapeutic agent to the human patient, wherein the combination of the CDDO-compound with the chemotherapeutic agent, is effective to treat the cancer.

The invention also describes methods of potentiating the effect of a chemotherapeutic agent on a tumor cell comprising contacting the tumor cell with a CDDO-compound and the chemotherapeutic agent.

In addition, the invention provides methods of inhibiting growth of a tumor cell comprising contacting the tumor cell with a CDDO-compound and a chemotherapeutic agent.

In all these methods, the CDDO-compound can be CDDO (2-cyano-3, 12-dioxoolen-1,9-dien-28-oic acid) or methyl-CDDO. In some embodiments, the chemotherapeutic agent is a retinoid. In some specific aspects, the retinoids are all-trans-retinoic acid (ATRA), 9-cis-retinoic acid, LG100268, LGD1069 (Targretin, bexarotene), fenretinide [N-(4-hydroxyphenyl)retinamide, 4-HPR], CD437 or any RXR- or RAR-specific retinoic acid. In additional embodiments, other chemotherapeutics described above and elsewhere in the specification may also be used.

In other embodiments, the invention provides methods for the treatment and prevention of graft versus host disease (GVHD) by providing a CDDO-compound either alone or in conjunction with another agent, such as an immunosupressive agent or a chemotherapeutic agent for the treatment of GVHD. In graft versus host disease the donor immune system mounts a response against the host's organs or tissue. As CDDO compounds, either alone or in conjunction with other agents, can induce apoptosis by inhibiting Bcl-2 and have activity in lymphoid tissue, the inventors contemplate that CDDO-compound based therapies can be used to provide therapy for graft versus host diseases.

Thus, the invention provides methods of inducing apoptosis in a lymphoid cell that expresses Bcl-2 comprising contacting said lymphoid cell with a CDDO-compound and an immunosupressive agent. The Bcl-2 may be expressed either endogenously or exogenously. In the case of exogenous Bcl-2 expression the Bcl-2 is expressed by a expression vector that comprises a nucleic acid that encodes Bcl-2 under the control of a promoter active in the lymphoid cell. Methods for achieving exogenous expression of nucleic acids are well known in the art and are described elsewhere in the specification. Such methods are also described in Sambrook and Maniatis (1993), incorporated herein by reference.

In some embodiments, the lymphoid cell is a T-cell. In other embodiments, the lymphoid cell is a cancer cell. In yet other embodiments, the lymphoid cell is located in a human. Although any immunosupressive agent known in the art can be used some non-limitying examples include corticosteroids and/or tacrolimus (SK506).

In some embodiments, the lymphoid cell is further additionally contacted with a chemotherapeutic agent.

The invention also provides methods of treating or preventing graft versus host disease in a subject comprising administering to the subject a CDDO-compound in combination with an immunosupressive agent. In some embodiments, the subject is further treated with a chemotherapeutic agent. The CDDO-compound is CDDO or methyl-CDDO.

In some embodiments, the subject is a human. In other embodiments, the subject has cancer. In yet other embodiments, the subject has received autologus bone marrow transplantation.

In some aspects the CDDO-compound is administered during ex vivo purging. Treatment of bone marrow or blood stem cells with CDDO-compounds, alone or with other agents, eliminates any tumor cells or leukemic cells or malignant cells. In other aspects the CDDO-compound is administered locally, for example, by direct intratumoral injection or by injection into tumor vasculature. In yet other aspects, the CDDO-compound is administered systemically, for example, intravenously, intra-arterially, intra-peritoneally, or orally.

Following longstanding patent law convention, the word "a" and "an", when used in conjunction with the word comprising, mean "one or more" in this specification, including the claims.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 11A. Binding of [3H]-rosiglitazone to PPARγ (cold CDDO as competitor).

FIG. 18A. LG-100268 synergistically enhances CDDO-induces killing in HL-60 cells.

DESCRIPTION OF ILLUSTRATIVE EMBODIMENTS

Figure 1:
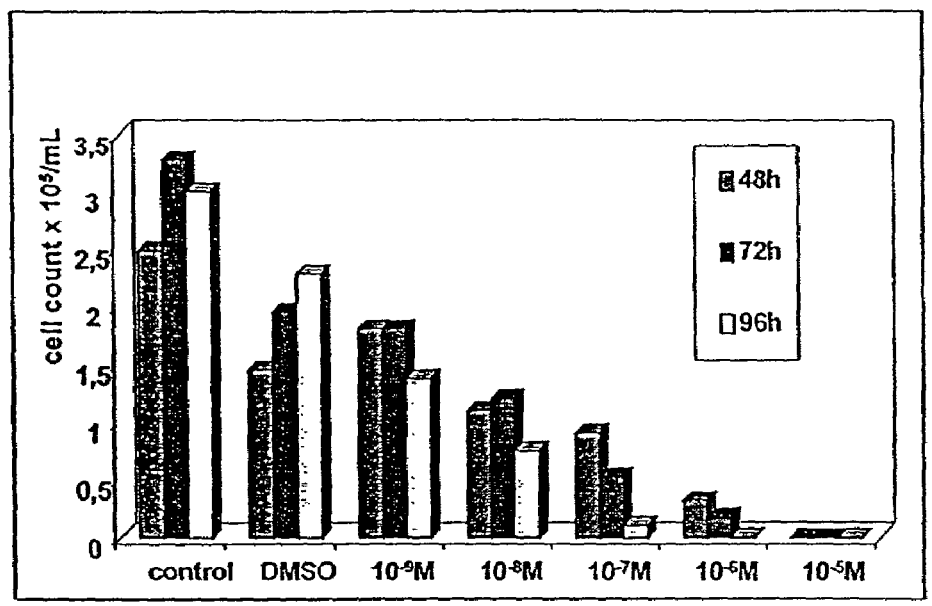
FIG. 1. CDDO decreases cell number in HL-60 cells.

Therapeutic regimens employed in the therapy of hematological malignancies have not proved very effective. For example, the cure rate for acute lymphoblastic leukemia (ALL), is very low and patients often suffer relapses after chemotherapy. In the case of chronic lymphocytic leukemia (CLL), the disease often transforms into a drug-resistant disease.

The present invention provides methods for anticancer therapy that comprise administering triterpenoid CDDO-compounds in combination with other chemotherapeutic agents. The term "CDDO-compounds" used in this specification refers to CDDO and methyl-CDDO (CDDO-Me). Among the two CDDO-compounds, CDDO-Me was found to be more potent.

The present invention demonstrates that CDDO-compounds in combination with a chemotherapeutic compound are very effective in inhibiting tumor cell growth; inducing apoptosis; inducing differentiation; and/or inducing cell death in several leukemic cells and cell lines. In addition, the induction of apoptosis by a combination of the CDDO-compound and a chempotherapeutic agent permits effective treatment using much lower doses of both agents as compared to the dosage of either agent alone.

Some of the chemotherapeutic agents, that are used in combination with the CDDO-compounds, target specific apoptotic pathways. One such class of chemotherapeutics are the retinoids. Therefore, the invention provides the use of retinoids, especially the RXR-specific ligands, as the other chemotherapeutic agents in combination with the CDDO-compounds as highly effective cancer treatments. CDDO-compounds are ligands of PPARγ receptors which form heterodimers with retinoid receptors. Thus, the anticancer properties of the CDDO-compounds are potentiated when combined with retinoids.

In addition, chemotherapeutic agents that may be used in combination with the CDDO-compounds include all standard and commonly used chemotherapeutic agents known in the art. Examples of these are described ahead in the specification and include DNA-damaging agents such as, ara-C, doxorubicin, danorubicin etc.

The invention also contemplates the use of other PPARγ ligands as chemotherapeutic agents. Also contemplated are the use of immunosuppressive agents such as corticosteroids and tacrolimus.

The present invention demonstrates an increase in cancer cell destruction compared to surrounding normal tissue and indicates that CDDO-compounds when combined with chemotherapy, provide a clinically useful tool.

As CDDO-compounds inhibit Bcl-2 and are effective in lymphoid cells, another aspect the invention concerns the treatment of graft versus host disease (GVHD) by providing a CDDO-compound either alone or in conjunction with another agent, such as an immunosupressive agent or a chemotherapeutic agent for the treatment of GVHD.

A. CDDO-compounds

CDDO. CDDO (2-cyano-3,12-dioxoolen-1,9-dien-28-oic acid) is a novel synthetic triterpenoid with potent differentiating, anti-proliferative and anti-inflammatory activity and was synthesized previously by the inventors (Suh et al., 1999). It inhibits proliferation of different tumor cell lines and induces monocytic differentiation of myeloid U937 cells. Recently, CDDO was found to be a specific ligand for PPARγ, while transactivation assays with glucocorticoid, estrogen, progesteron, and retinoid receptors were negative (Suh et al., 1999). The inventors have demonstrated that CDDO exerts strong antiproliferative, and apoptotic effects on leukemic cell lines and primary AML in vitro and also induces monocytic differentiation of leukemic cell lines and some primary AMLs. CDDO also mediated reduction in colony formation in AML progenitors as compared with normal $CD34^+$ cells (Konopleva et al., 1999). This differential effect on normal vs. leukemic progenitor cells is useful for AML therapy. The present invention shows that this effect is profoundly increased by combination of CDDO with retinoids such as all-trans retinoic acid (ATRA) in HL-60 cells. CDDO combined with ATRA also exhibits an enhanced pro-apoptotic effect. In addition to ATRA, other retinoids contemplated as useful include 9-cis retinoic acid, LG100268, LGD1069 (Targretin, bexarotene), fenretinide [N-(4-hydroxyphenyl)retinamide, 4-HPR] and CD437. Furthermore, the invention shows that CDDO-compounds increases ara-C cytotoxicity. The invention also shows that CDDO in combination with other chemotherapeutic agents has potent anticancer effects.

Method of Synthesis of CDDO.

CDDO may be synthesized by the scheme outlined below.

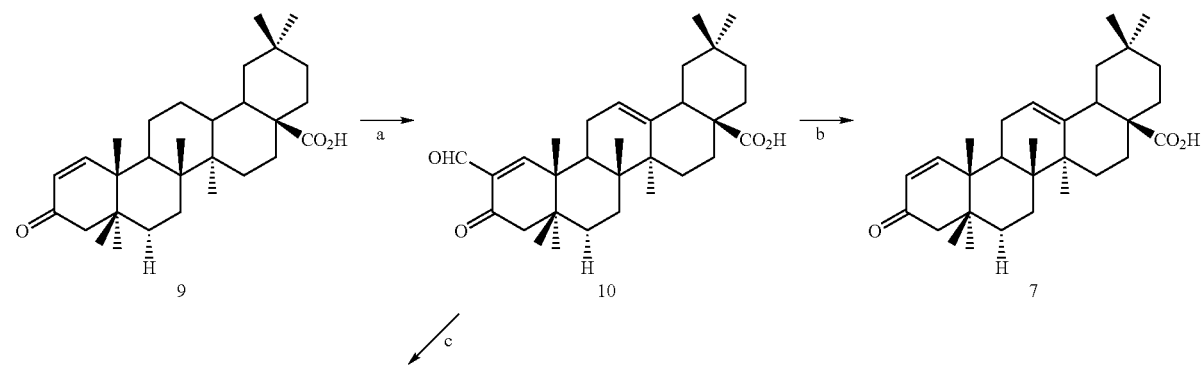

Scheme 1

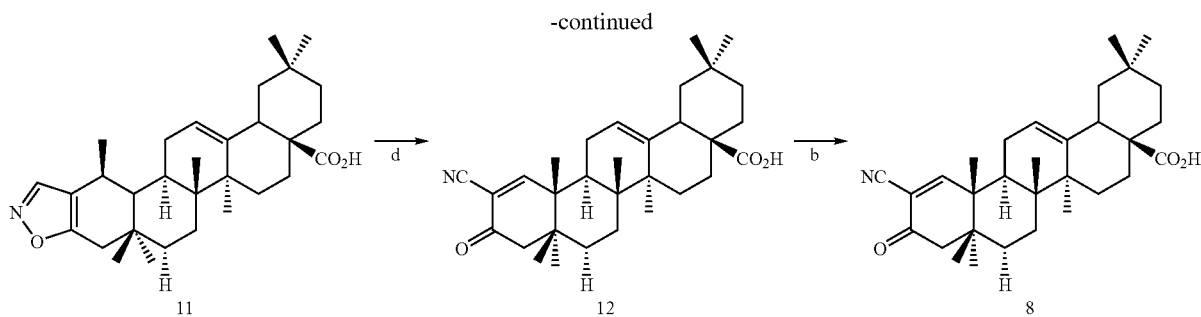

Methyl-CDDO. Methyl-CDDO (CDDO-Me), the C-28 methyl ester of CDDO, also exerts strong antiproliferative and apoptotic effects on leukemic cell lines and in primary AML samples in vitro as well as induces monocytic differentiation of leukemic cell lines and some primary AMLs. Thus, CDDO-Me provides chemotherapy for the treatment of leukemias. The present invention demonstrates that this effect is profoundly increased by combination of CDDO-Me with other chemotherapeutic agents. These include retinoids such as ATRA, 9-cis retinoic acid, , LG100268, LGD1069 (Tarinhibits in vitro angiogenesis. The ability of CDDO-Me in combination with retinoids to induce differentiation in leukemic cells in vitro show that these compounds may have similar in vivo effects. The anti-angiogenic properties of CDDO-Me further increase its potent anti-leukemia activity in combination with retinoids. Furthermore, CDDO-Me was found to be more potent at lower concentrations than CDDO.

Method of Synthesis of CDDO-Me.

CDDO-Me may be synthesized by the scheme outlined below.

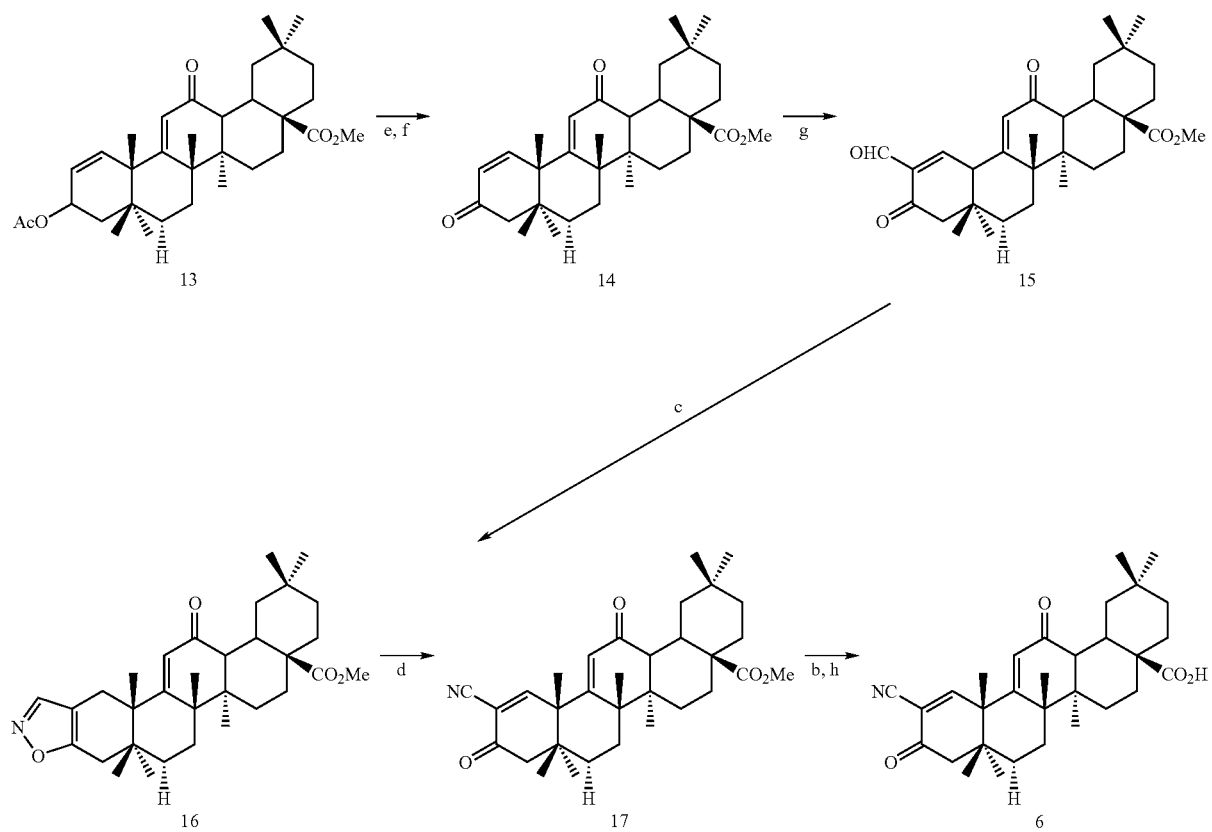

gretin, bexarotene), fenretinide [N-(4-hydroxyphenyl)retinamide, 4-HPR], CD437 and other RXR and RAR-specific ligands. This combination also increases ara-C cytotoxicity, further reduces AML colony formation, inhibits ERK phosphorylation and promotes Bcl-2 dephosphorylation, and The present invention provides combinations of CDDO-compounds and chemotherapeutic agents that are useful as treatments for cancers and hematological malignancies. In one embodiment, the chemotherapeutics are retinoids. As CDDO-compounds are PPARγ ligands and PPARγ is known to be altered in many types of cancers, the inventors contemplate, that ligation of PPARγ in combination with retinoids such as, RXR-specific ligands, provides a mechanistic basis for maximal increase in transcriptional activity of the target genes that control apoptosis and differentiation. The CDDO-compounds and retinoids in combination demonstrate an increased ability to induce differentiation, induce cytotoxicity, induce apoptosis, induce cell killing, reduce colony formation and inhibit the growth of several types of leukemic cells.

B. Retinoids

Retinoids are a group vitamin A derivatives that have potential application in chemoprevention and in therapy of many types of malignancies. They have been used as chemotherapeutics for the treatment and prevention of a variety of cancerous and pre-cancerous conditions, such as melanoma, cervical cancer, some forms of leukemia, oral leukoplakia and basal and squamous cell carcinomas. Retinoids can also modulate programmed cell death (apoptosis) and are therefore important to cancer therapy. They act via interaction with two major classes of nuclear receptors, the retinoid acid receptors (RARs) and the retinoid X receptors (RXRs) that function as dimeric, ligand-dependent transcription factors (Pfahl et al., 1994). The apoptosis controlling protein, Bcl-2, functions as a downstream regulator of retinoid-induced cell growth and differentiation in hematopoietic cells.

All-trans-retinoic acid (ATRA) belongs to the retinoid family of ligands for nuclear receptors. Other retinoid ligands used herein include 9-cis-retinoic acid, LG-100286, Fenretinide [N-(4-hydroxyphenyl)retinamide, 4-HPR], LG1069 (also alternatively known as Targretin, bexarotene) and CD-437 are some other retinoids contemplated. CD437 is a novel retinoid that binds to both RARγ and RARβ retinoids receptors. It is a potent inducer of apoptosis in vitro. No trials in humans have been conducted. In mice, oral administration of 10-30 mg/kg daily for 3 wk or injection of 10 mg/kg of body weight in the tumor caused growth inhibition of melanoma xenografts in vivo (Schadendorf, et al., 1996). However, one of skill in the art will recognize that one may use any other retinoid. Such a retinoid may be naturally occurring or synthetic. The retinoid may further be a ligand of the RXR receptors and/or the RAR receptors.

Retinoids may be administered by any route as described herein and in other parts of this specification. In some specific embodiments, ATRA may be administered at a range of 10-100 mg/m$^2$/day, for example, at 45 mg/m$^2$/day orally daily. A liposomal formulation of ATRA may be administered at 90 mg/m$^2$/day IV. 9-cis-Retinoid acid may be administered at a range of 20-150 mg/m$^2$ twice a day orally. LG100268 in mice models was administered at a dose of 5-10 mg/kg. LGD1069 is contemplated as useful for the topical treatment of cutaneous lesions in patients with cutaneous T-cell lymphoma (CTCL) who have refractory or resistant disease after other therapies. In some embodiments the LGD1069 is administered as capsules of 300-400 mg/m$^2$/day taken orally. In other embodiments, LGD1069 is administered as a gel of about 1% strength for the topical treatment of cutaneous lesions in patients with CTCL (Stage 1A and 1B) who have refractory or resistant disease after other cancer therapies and may be taken two to four times daily. Fenretinide [N-(4-hydroxyphenyl)retinamide, 4-HPR] is contemplated useful at 25-600 mg daily and may be administered continuously in some embodiments. One of skill in the art will understand that while these dosage ranges provide useful guidelines appropriate adjustments in the dosage depending on the needs of an individual patient factoring in disease, gender, age and other general health conditions will be made by the trained physician.

C. PPAR

The peroxisome proliferator-activated receptor (PPAR) is a member of a nuclear receptor family that is involved in apoptosis. This family includes receptors for the steroid, thyroid and retinoid hormones that often serve as transcription factors. The three known human PPAR subtypes, α, γ and δ, show distinct tissue distribution and are associated with selective ligands (Forman et al., 1997; Kliewer et al., 1994; Wilson et al., 1996). PPARγ is expressed at high levels in adipose tissue and in macrophages and can induce cell cycle arrest and differentiation of preadipocyte cells. As these receptors regulate key genes involved in cellular homeostasis and differentiation, they have value as therapeutic targets.

The present inventors show that the CDDO-compounds are PPARγ ligands. Endogenous PPARγ ligands include fatty acid-like compounds such as 15-deoxyΔ$^{12,14}$PGJ2 and linoleic acid (Forman et al., 1995; Kliewer et al., 1995; Nagy et al., 1998). Some examples of PPAR pharmaceutical ligands include the thiazolidinediones (TZDs) such as troglitazone, BRL49653 (rosiglitazone), and pioglitazone, and non-steroidal anti-inflammatory drugs (Lehmann et al., 1997), L-805645, GW347845X. TZDs are used for the treatment of type 2 diabetes because they sensitize tissues to insulin (Lehmann et al., 1995).

PPARγ shares structural similarities with other nuclear-receptor family members, including a central DNA-binding domain and a carboxy-terminal ligand-binding domain (LBD). All nuclear receptors require the transcription activation function (AF-2) domain that is located in the C-terminus of the LBD (Evans, 1988), for the recruitment of the co-activator SRC-1. PPARγ must form a heterodimer with RXR to bind DNA and activate transcription (Nolte et al., 1998). PPAR-RXR heterodimers can be activated by PPAR or RXR ligands (Forman et al., 1997), and RXR-specific ligands markedly induce the binding of SRC-1 to PPARγ-RXR heterodimers (Westin et al., 1998). Assembly of this complex results in a large increase in transcriptional activity. The present inventors contemplate that one could increase the effects of PPARγ ligands by combining them with ligands specific for RXR. For example, the present inventors have shown that combination of CDDO with a RXR-specific ligand, such as ATRA, decreases cell viability and induces terminal differentiation in myeloid leukemic cell lines. In RXR-expressing HL-60 cells CDDO in combination with a RXR ligand induces histone acetylation. Additionally, the inventors tested the effects of the PPARγ ligands listed above alone and in combination with retinoids and found an increased differentiation followed by apoptosis in leukemic cells.

It has also been shown that simultaneous activation of both receptors can yield maximal antidiabetic activation in vivo (Mukherjee et al., 1997). For example, combinations of the PPARγ ligands, 15D-PGJ2 or BRL49563 with RXR-specific ligand LG100268 markedly decreased cell growth and induced monocytic differentiation in HL-60 cells indicating that activation of the PPARγ/RXR heterodimer represents a novel regulatory pathway for HL-60 maturation (Tontonoz et al., 1998). As SRC co-activator proteins possess intrinsic histone acetyltransferase activity, ligand-mediated receptor transactivation may involve targeted histone acetylation of chromatin by recruited coactivators.

Transactivation of PPARγ target genes is a multi-step process that first involves binding of the PPARγ/RXR heterodimer to specific DR1-type response elements in the promoter of a target gene. In the absence of ligand, this heterodimer associates with a complex of co-repressor proteins that silence the promoter by deacetylating histones in the adjacent chromatin. Ligand binding induces a conformational change in the receptor, which dissociates the co-repressor complex, and permits the heterodimer to interact with at least two co-activator complexes, namely p160/CBP and DRIP (also called TRAP or ARC)-FIG. 1. These two complexes acetylate histones (making adjacent chromatin more accessible) and bridge the PPARγ/RXR heterodimer to the basal transcriptional machinery, thus driving transcription of the target gene. This ligand-induced transactivation is dependent on: 1) the different types of co-repressors and co-activators associated with the receptor heterodimer, and 2) the relative affinities of these cofactors for PPARγ and RXR. Indeed, it has already been shown that RXR and PPARγ agonists recruit different co-activators to the heterodimer (Yang et al., 2000).

There is emerging evidence of the involvement of PPAR-signaling in cancer as shown by the following: 1. High expression of PPARγ mRNA and protein has been observed in six colon cancer cell lines (Kitamura et al., 1999). Troglitazone, a selective PPARγ ligand, causes marked cell cycle arrest and enterocyte differentiation markers. In addition, four somatic PPARγ mutations were found among 55 sporadic colon cancers. Each greatly impaired the function of the protein (Sarraf et al., 1999). These data demonstrate that colon cancer in humans is associated with loss-of-function mutations in the PPARγ. 2. Significant PPARγ expression is detected in most human metastatic breast cancers (Mueller et al., 1998). The ligand activation of PPARγ causes a remarkable response in the breast cancer cells with neutral lipid accumulation and changes in gene expression. 3. PPARγ is expressed at high levels in human liposarcoma, and primary liposarcoma cells can be induced to undergo terminal differentiation by treatment with the PPARγ ligand pioglitazone, demonstrating that the differentiation block in these cells can be overcome by maximal activation of the PPARγ pathway (Tontonoz et al., 1997). Remarkably, simultaneous treatment of liposarcoma cells with both PPARγ- and RXR-specific ligands resulted in additive stimulation of differentiation. 4. 15-deoxy$\Delta^{21,14}$PGJ2, a PPARγ ligand, induced caspase-dependent apoptosis in JEG3 choriocarcinoma cells (Keelan et al., 1999). 5. PPARγ2 transcript is expressed in leukemic cells from patients with AML, ALL, and CML, as well as in normal neutrophils and peripheral blood lymphocytes (Greene et al., 1995). In contrast, only full-length 1.85-kb PPARγ1 transcript was detected in a variety of human leukemia cell lines and in primary bone marrow stromal cells. The PPARγ gene is mapped to human chromosome 3p25. 3p deletions are commonly seen in a variety of carcinomas, and the 3p25-p21 deletion is seen infrequently in patients with chronic lymphocytic leukemias, and non-Hodgkin's lymphomas (Johansson et al., 1997). 6. PPARγ is also involved in angiogenesis (Veiga et al., 1999). Ligation of PPARγ exerted anti-angiogenic effects. Thus, the CDDO-compounds described herein, which are PPARγ ligands, provide selective killing of cancer cells that express more PPARγ receptors. Hence, the combination therapies described in this invention are envisioned to be effective in various types of cancers.

D. Therapeutic Regimens

Tumor cell resistance to chemotherapy and radiotherapy agents represents a major problem in clinical oncology. In the context of the present invention, it is contemplated that combination therapy using CDDO-compounds with other chemotherapeutics could be used. The other chemotherapeutics include retinoid compounds described above and in other parts of this specification and include RXR-specific ligands, ATRA, 9-cis-retinoic acid, LG100268, LGD1069 (Targretin, bexarotene), fenretinide [N-(4-hydroxyphenyl)retinamide, 4-HPR], and CD437. In addition other synthetic and naturally occurring retinoids are contemplated as useful. As the CDDO-compounds are PPARγ ligands and the heterodimerization of PPARγ and RXR's enhances gene transcription of apoptotic pathways, other PPARγ ligands such as those described above and in other parts of this specification are also contemplated as useful anticancer therapies in combination with retinoids. Some examples are endogenous PPARγ ligands such as 15-deoxy$\Delta^{12,14}$PGJ2 and linoleic acid and pharmaceutical PPARγ ligands including the thiazolidinediones (TZDs) such as troglitazone, BRL49653 (rosiglitazone), and pioglitazone, L-805645, GW347845X, and non-steroidal anti-inflammatory drugs. In addition, other PPARγ-ligands contemplated as useful in this invention include all naturally occurring ligands as well as synthetically prepared compounds. Yet other chemotherapeutic agents that may be used in combination with the CDDO-compounds to achieve cancer therapy are described later in the specification.

Cancers that can be treated with the present invention include, but are not limited to, hematological malignancies including: blood cancer, myeloid leukemia, monocytic leukemia, myelocytic leukemia, promyelocytic leukemia, myeloblastic leukemia, lymphocytic leukemia, acute myelogenous leukemic, chronic myelogenous leukemic, lymphoblastic leukemia, hairy cell leukemia. Solid cell tumors and cancers that can be treated include those such as tumors of the brain (glioblastomas, medulloblastoma, astrocytoma, oligodendroglioma, ependymomas), lung, liver, spleen, kidney, lymph node, small intestine, pancreas, colon, stomach, breast, endometrium, prostate, testicle, ovary, skin, head and neck, esophagus. Furthermore, the cancer may be a precancer, a metastatic and/or a non-metastatic cancer.

"Effective amount" is defined as an amount of the agent that will decrease, reduce, inhibit or otherwise abrogate the growth of a cancer cell, induce apoptosis, inhibit metastasis, induce differentiation, kill cells or induce cytotoxicity in cells.

The administration of the other chemotherapeutic may precede or follow the therapy using CDDO-compounds by intervals ranging from minutes to days to weeks. In embodiments where the other chemotherapeutic and the CDDO-compound are administered together, one would generally ensure that a significant period of time did not expire between the time of each delivery. In such instances, it is contemplated that one would administer to a patient both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the other chemotherapeutic and the CDDO-compound will be required to achieve complete cancer cure. Various combinations may be employed, where the other chemotherapeutic agent is "A" and the CDDO-compound is "B", as exemplified below:

A/B/A B/A/B B/B/A A/A/B B/A/A A/B/B B/B/B/A

B/B/A/B A/A/B/B A/B/A/B A/B/B/A B/B/A/A B/A/B/A

B/A/A/B B/B/B/A A/A/A/B B/A/A/A A/B/A/A A/A/B/A

A/B/B/B B/A/B/B B/B/A/B

Other combinations also are contemplated. The exact dosages and regimens of each agent can be suitable altered by those of ordinary skill in the art.

In embodiments of the invention that concern graft versus host disease (GVHD) treatment and prevention, the additional use of immunosupressive agents is also contemplated. Thus, 'A' in the above scheme may represent an immunosupressive agent. Furthermore, it is also contemplated that one may use a CDDO-compound, a chemotherapeutic agent as well as an immunosupressive agent in various combinations.

a) Chemotherapeutic Agents

Agents that damage DNA are chemotherapeutics. These can be, for example, agents that directly cross-link DNA, agents that intercalate into DNA, and agents that lead to chromosomal and mitotic aberrations by affecting nucleic acid synthesis. Agents that directly cross-link nucleic acids, specifically DNA, are envisaged and are exemplified by cisplatin, and other DNA alkylating agents. Agents that damage DNA also include compounds that interfere with DNA replication, mitosis, and chromosomal segregation.

Some examples of chemotherapeutic agents include antibiotic chemotherapeutics such as, Doxorubicin, Daunorubicin, Mitomycin (also known as mutamycin and/or mitomycin-C), Actinomycin D (Dactinomycin), Bleomycin, Plicomycin, Plant alkaloids such as Taxol, Vincristine, Vinblastine. Miscellaneous agents such as Cisplatin, VP16, Tumor Necrosis Factor. Alkylating Agents such as, Carmustine, Melphalan (also known as alkeran, L-phenylalanine mustard, phenylalanine mustard, L-PAM, or L-sarcolysin, is a phenylalanine derivative of nitrogen mustard), Cyclophosphamide, Chlorambucil, Busulfan (also known as myleran), Lomustine. And other agents for example, Cisplatin (CDDP), Carboplatin, Procarbazine, Mechlorethamine, Camptothecin, Ifosfamide, Nitrosurea, Etoposide (VP16), Tamoxifen, Raloxifene, Estrogen Receptor Binding Agents, Gemcitabien, Navelbine, Farnesyl-protein transferase inhibitors, Transplatinum, 5-Fluorouracil, and Methotrexate, Temazolomide (an aqueous form of DTIC), Mylotarg, Dolastatin-10, Bryostatin, or any analog or derivative variant of the foregoing.

Retinoids and the PPARγ ligands are also some chemotherapeutic agents contemplated useful in the present invention. Retinoids include all RXR and RAR-specific retinoic acid ligands. For example, ATRA, 9-cis retinoic acid, LG100268, LGD1069 (Targretin, bexarotene), fenretinide [N-(4-hydroxyphenyl)retinamide, 4-HPR] and CD437 are contemplated as useful. CD437 is a novel retinoids that binds to the RARγ and RARβ retinoids receptors. It is a potent inducer of apoptosis in vitro. No trials in humans have been conducted with this chemotherapeutic so far. However, in mice models, oral administration of 10-30 mg/kg daily for 3 wk or injection of 10 mg/kg of body weight in the tumor caused growth inhibition of melanoma xenografts in vivo (Schadendorf D. et al., 1996).

ATRA may be administered at a range of 10-100 mg/m$^2$/day, for example, at 45 mg/m$^2$/day orally daily. A liposomal formulation of ATRA may be administered at 90 mg/m$^2$/day IV. 9-cis-Retinoid acid may be administered at a range of 20-150 mg/m$^2$ twice a day orally. LG100268 in mice models was administered at a dose of 5-10 mg/kg. LGD1069 is contemplated as useful for the topical treatment of cutaneous lesions in patients with cutaneous T-cell lymphoma (CTCL) who have refractory or resistant disease after other therapies. In some embodiments the LGD1069 is administered as capsules of 300-400 mg/m$^2$/day taken orally. In other embodiments, LGD1069 is administered as a gel of about 1% strength for the topical treatment of cutaneous lesions in patients with CTCL (Stage (1A and 1B) who have refractory or resistant disease after other cancer therapies and may be taken two to four times daily. Fenretinide [N-(4-hydroxyphenyl)retinamide, 4-HPR] is contemplated useful at 25-600 mg daily and may be administered continuously in some embodiments.

Endogenous PPARγ ligands such as 15-deoxyΔ$^{12,14}$PGJ2 and linoleic acid and pharmaceutical PPARγ ligands including the thiazolidinediones (TZDs) such as troglitazone, BRL49653 (rosiglitazone) and pioglitazone, L-805645, GW347845X, and non-steroidal anti-inflammatory drugs are also contemplated useful in context of the instant invention.

(i) Antibiotics

Doxorubicin. Doxorubicin hydrochloride, 5,12-Naphthacenedione, (8s-cis)-10-[(3-amino-2,3,6-trideoxy-a-L-lyxo-hexopyranosyl)oxy]-7,8,9,10-tetrahydro-6,8,11-trihydroxy-8-(hydroxyacetyl)-1-methoxy-hydrochloride (hydroxydaunorubicin hydrochloride, Adriamycin) is used in a wide antineoplastic spectrum. It binds to DNA and inhibits nucleic acid synthesis, inhibits mitosis and promotes chromosomal aberrations.

Administered alone, it is the drug of first choice for the treatment of thyroid adenoma and primary hepatocellular carcinoma. It is a component of 31 first-choice combinations for the treatment of ovarian, endometrial and breast tumors, bronchogenic oat-cell carcinoma, non-small cell lung carcinoma, gastric adenocarcinoma, retinoblastoma, neuroblastoma, mycosis fungoides, pancreatic carcinoma, prostatic carcinoma, bladder carcinoma, myeloma, diffuse histiocytic lymphoma, Wilms' tumor, Hodgkin's disease, adrenal tumors, osteogenic sarcoma soft tissue sarcoma, Ewing's sarcoma, rhabdomyosarcoma and acute lymphocytic leukemia. It is an alternative drug for the treatment of islet cell, cervical, testicular and adrenocortical cancers. It is also an immunosuppressant.

Doxorubicin is absorbed poorly and must be administered intravenously. The pharmacokinetics are multicompartmental. Distribution phases have half-lives of 12 minutes and 3.3 hr. The elimination half-life is about 30 hr. Forty to 50% is secreted into the bile. Most of the remainder is metabolized in the liver, partly to an active metabolite (doxorubicinol), but a few percent is excreted into the urine. In the presence of liver impairment, the dose should be reduced.

Appropriate doses are, intravenous, adult, 60 to 75 mg/m$^2$ at 21-day intervals or 25 to 30 mg/m$^2$ on each of 2 or 3 successive days repeated at 3- or 4-wk intervals or 20 mg/m$^2$ once a week. The lowest dose should be used in elderly patients, when there is prior bone-marrow depression caused by prior chemotherapy or neoplastic marrow invasion, or when the drug is combined with other myelopoietic suppressant drugs. The dose should be reduced by 50% if the serum bilirubin lies between 1.2 and 3 mg/dL and by 75% if above 3 mg/dL. The lifetime total dose should not exceed 550 mg/m$^2$ in patients with normal heart function and 400 mg/m$^2$ in persons having received mediastinal irradiation. Alternatively, 30 mg/m$^2$ on each of 3 consecutive days, repeated every 4 wk. Exemplary doses may be 10 mg/m $^2$, 20 mg/m$^2$, 30 mg/m$^2$, 50 mg/m$^2$, 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

Daunorubicin. Daunorubicin hydrochloride, 5,12-Naphthacenedione, (8S-cis)-8-acetyl-10-[(3-amino-2,3,6-trideoxy-a-L-lyxo-hexanopyranosyl)oxy]-7,8,9,10-tetrahydro-6,8,11-trihydroxy-10-methoxy-, hydrochloride; also termed cerubidine and available from Wyeth. Daunorubicin intercalates into DNA, blocks DAN-directed RNA polymerase and inhibits DNA synthesis. It can prevent cell division in doses that do not interfere with nucleic acid synthesis.

In combination with other drugs it is included in the first-choice chemotherapy of acute myelocytic leukemia in adults (for induction of remission), acute lymphocytic leukemia and the acute phase of chronic myelocytic leukemia. Oral absorption is poor, and it must be given intravenously. The half-life of distribution is 45 minutes and of elimination, about 19 hr. The half-life of its active metabolite, daunorubicinol, is about 27 hr. Daunorubicin is metabolized mostly in the liver and also secreted into the bile (ca 40%). Dosage must be reduced in liver or renal insufficiencies.

Suitable doses are (base equivalent), intravenous adult, younger than 60 yr. 45 mg/m$^2$/day (30 mg/m$^2$ for patients older than 60 yr.) for 1, 2 or 3 days every 3 or 4 wk or 0.8 mg/kg/day for 3 to 6 days every 3 or 4 wk; no more than 550 mg/m$^2$ should be given in a lifetime, except only 450 mg/m$^2$ if there has been chest irradiation; children, 25 mg/m$^2$ once a week unless the age is less than 2 yr. or the body surface less than 0.5 m, in which case the weight-based adult schedule is used. It is available in injectable dosage forms (base equivalent) 20 mg (as the base equivalent to 21.4 mg of the hydrochloride). Exemplary doses may be 10 mg/m$^2$, 20 mg/m$^2$, 30 mg/m$^2$, 50 mg/m$^2$, 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

Mitomycin. Mitomycin (also known as mutamycin and/or mitomycin-C) is an antibiotic isolated from the broth of *Streptomyces caespitosus* which has been shown to have antitumor activity. The compound is heat stable, has a high melting point, and is freely soluble in organic solvents.

Mitomycin selectively inhibits the synthesis of deoxyribonucleic acid (DNA). The guanine and cytosine content correlates with the degree of mitomycin-induced cross-linking. At high concentrations of the drug, cellular RNA and protein synthesis are also suppressed.

In humans, mitomycin is rapidly cleared from the serum after intravenous administration. Time required to reduce the serum concentration by 50% after a 30 mg bolus injection is 17 minutes. After injection of 30 mg, 20 mg, or 10 mg I.V., the maximal serum concentrations were 2.4 mg/mL, 1.7 mg/mL, and 0.52 mg/mL, respectively. Clearance is effected primarily by metabolism in the liver, but metabolism occurs in other tissues as well. The rate of clearance is inversely proportional to the maximal serum concentration because, it is thought, of saturation of the degradative pathways.

Approximately 10% of a dose of mitomycin is excreted unchanged in the urine. Since metabolic pathways are saturated at relatively low doses, the percent of a dose excreted in urine increases with increasing dose. In children, excretion of intravenously administered mitomycin is similar.

Actinomycin D. Actinomycin D (Dactinomycin) [50-76-0]; $C_{62}H_{86}N_{12}O_{16}$ (1255.43) is an antineoplastic drug that inhibits DNA-dependent RNA polymerase. It is a component of first-choice combinations for treatment of choriocarcinoma, embryonal rhabdomyosarcoma, testicular tumor and Wilms' tumor. Tumors which fail to respond to systemic treatment sometimes respond to local perfusion. Dactinomycin potentiates radiotherapy. It is a secondary (efferent) immunosuppressive.

Actinomycin D is used in combination with primary surgery, radiotherapy, and other drugs, particularly vincristine and cyclophosphamide. Antineoplastic activity has also been noted in Ewing's tumor, Kaposi's sarcoma, and soft-tissue sarcomas. Dactinomycin can be effective in women with advanced cases of choriocarcinoma. It also produces consistent responses in combination with chlorambucil and methotrexate in patients with metastatic testicular carcinomas. A response may sometimes be observed in patients with Hodgkin's disease and non-Hodgkin's lymphomas. Dactinomycin has also been used to inhibit immunological responses, particularly the rejection of renal transplants.

Half of the dose is excreted intact into the bile and 10% into the urine; the half-life is about 36 hr. The drug does not pass the blood-brain barrier. Actinomycin D is supplied as a lyophilized powder (0/5 mg in each vial). The usual daily dose is 10 to 15 mg/kg; this is given intravenously for 5 days; if no manifestations of toxicity are encountered, additional courses may be given at intervals of 3 to 4 weeks. Daily injections of 100 to 400 mg have been given to children for 10 to 14 days; in other regimens, 3 to 6 mg/kg, for a total of 125 mg/kg, and weekly maintenance doses of 7.5 mg/kg have been used. Although it is safer to administer the drug into the tubing of an intravenous infusion, direct intravenous injections have been given, with the precaution of discarding the needle used to withdraw the drug from the vial in order to avoid subcutaneous reaction. Exemplary doses may be 100 mg/m, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

Bleomycin. Bleomycin is a mixture of cytotoxic glycopeptide antibiotics isolated from a strain of *Streptomyces verticillus*. It is freely soluble in water. Although the exact mechanism of action of bleomycin is unknown, available evidence would seem to indicate that the main mode of action is the inhibition of DNA synthesis with some evidence of lesser inhibition of RNA and protein synthesis.

In mice, high concentrations of bleomycin are found in the skin, lungs, kidneys, peritoneum, and lymphatics. Tumor cells of the skin and lungs have been found to have high concentrations of bleomycin in contrast to the low concentrations found in hematopoietic tissue. The low concentrations of bleomycin found in bone marrow may be related to high levels of bleomycin degradative enzymes found in that tissue.

In patients with a creatinine clearance of >35 mL per minute, the serum or plasma terminal elimination half-life of bleomycin is approximately 115 minutes. In patients with a creatinine clearance of <35 mL per minute, the plasma or serum terminal elimination half-life increases exponentially as the creatinine clearance decreases. In humans, 60% to 70% of an administered dose is recovered in the urine as active bleomycin.

Bleomycin should be considered a palliative treatment. It has been shown to be useful in the management of the following neoplasms either as a single agent or in proven combinations with other approved chemotherapeutic agents in squamous cell carcinoma such as head and neck (including mouth, tongue, tonsil, nasopharynx, oropharynx, sinus, palate, lip, buccal mucosa, gingiva, epiglottis, larynx), skin, penis, cervix, and vulva. It has also been used in the treatment of lymphomas and testicular carcinoma.

Because of the possibility of an anaphylactoid reaction, lymphoma patients should be treated with two units or less for the first two doses. If no acute reaction occurs, then the regular dosage schedule may be followed.

Improvement of Hodgkin's Disease and testicular tumors is prompt and noted within 2 weeks. If no improvement is seen by this time, improvement is unlikely. Squamous cell cancers respond more slowly, sometimes requiring as long as 3 weeks before any improvement is noted.

Bleomycin may be given by the intramuscular, intravenous, or subcutaneous routes.

(ii) Miscellaneous Agents

Cisplatin. Cisplatin has been widely used to treat cancers such as metastatic testicular or ovarian carcinoma, advanced bladder cancer, head or neck cancer, cervical cancer, lung cancer or other tumors. Cisplatin can be used alone or in combination with other agents, with efficacious doses used in clinical applications of 15-20 mg/m$^2$ for 5 days every three weeks for a total of three courses. Exemplary doses may be 0.50 mg/m$^2$, 1.0 mg/m$^2$, 1.50 mg/m$^2$, 1.75 mg/m$^2$, 2.0 mg/m$^2$, 3.0 mg/m$^2$, 4.0 mg/m$^2$, 5.0 mg/m$^2$, 10 mg//m$^2$. Of course, all of these dosages are exemplary, and any dosage in-between these points is also expected to be of use in the invention.

Cisplatin is not absorbed orally and must therefore be delivered via injection intravenously, subcutaneously, intratumorally or intraperitoneally.

Cisplatin may also be used in combination with emodin or emodin-like compounds in the treatment of non-small cell lung carcinoma. Combination of cisplatin and emodin and or emodin-like compounds may also be used for the treatment of any neu-mediated cancers.

VP16. VP16 is also know as etoposide and is used primarily for treatment of testicular tumors, in combination with bleomycin and cisplatin, and in combination with cisplatin for small-cell carcinoma of the lung. It is also active against non-Hodgkin's lymphomas, acute nonlymphocytic leukemia, carcinoma of the breast, and Kaposi's sarcoma associated with acquired immunodeficiency syndrome (AIDS).

VP16 is available as a solution (20 mg/ml) for intravenous administration and as 50-mg, liquid-filled capsules for oral use. For small-cell carcinoma of the lung, the intravenous dose (in combination therapy) is can be as much as 100 mg/m$^2$ or as little as 2 mg/m$^2$, routinely 35 mg/m$^2$, daily for 4 days, to 50 mg/m$^2$, daily for 5 days have also been used. When given orally, the dose should be doubled. Hence the doses for small cell lung carcinoma may be as high as 200-250 mg/m$^2$. The intravenous dose for testicular cancer (in combination therapy) is 50 to 100 mg/m$^2$ daily for 5 days, or 100 mg/m$^2$ on alternate days, for three doses. Cycles of therapy are usually repeated every 3 to 4 weeks. The drug should be administered slowly during a 30- to 60-minute infusion in order to avoid hypotension and bronchospasm, which are probably due to the solvents used in the formulation.

Tumor Necrosis Factor. Tumor Necrosis Factor [TNF; Cachectin] is a glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. Some infectious agents cause tumor regression through the stimulation of TNF production. TNF can be quite toxic when used alone in effective doses, so that the optimal regimens probably will use it in lower doses in combination with other drugs. Its immunosuppressive actions are potentiated by gamma-interferon, so that the combination potentially is dangerous. A hybrid of TNF and interferon-α also has been found to possess anti-cancer activity.

(iii) Plant Alkaloids

Taxol. Taxol is an experimental antimitotic agent, isolated from the bark of the ash tree, *Taxus brevifolia*. It binds to tubulin (at a site distinct from that used by the vinca alkaloids) and promotes the assembly of microtubules. Taxol is currently being evaluated clinically; it has activity against malignant melanoma and carcinoma of the ovary. Maximal doses are 30 mg/m$^2$ per day for 5 days or 210 to 250 mg/m$^2$ given once every 3 weeks. Of course, all of these dosages are exemplary, and any dosage in-between these points is also expected to be of use in the invention.

Vincristine. Vincristine blocks mitosis and produces metaphase arrest. It seems likely that most of the biological activities of this drug can be explained by its ability to bind specifically to tubulin and to block the ability of protein to polymerize into microtubules. Through disruption of the microtubules of the mitotic apparatus, cell division is arrested in metaphase. The inability to segregate chromosomes correctly during mitosis presumably leads to cell death.

The relatively low toxicity of vincristine for normal marrow cells and epithelial cells make this agent unusual among anti-neoplastic drugs, and it is often included in combination with other myelosuppressive agents.

Unpredictable absorption has been reported after oral administration of vinblastine or vincristine. At the usual clinical doses the peak concentration of each drug in plasma is approximately 0.4 mM.

Vinblastine and vincristine bind to plasma proteins. They are extensively concentrated in platelets and to a lesser extent in leukocytes and erythrocytes.

Vincristine has a multiphasic pattern of clearance from the plasma; the terminal half-life is about 24 hours. The drug is metabolized in the liver, but no biologically active derivatives have been identified. Doses should be reduced in patients with hepatic dysfunction. At least a 50% reduction in dosage is indicated if the concentration of bilirubin in plasma is greater than 3 mg/dl (about 50 mM).

Vincristine sulfate is available as a solution (1 mg/ml) for intravenous injection. Vincristine used together with corticosteroids is presently the treatment of choice to induce remissions in childhood leukemia; the optimal dosages for these drugs appear to be vincristine, intravenously, 2 mg/m$^2$ of body-surface area, weekly, and prednisolone, orally, 40 mg/m$^2$, daily. Adult patients with Hodgkin's disease or non-Hodgkin's lymphomas usually receive vincristine as a part of a complex protocol. When used in the MOPP regimen, the recommended dose of vincristine is 1.4 mg/m$^2$. High doses of vincristine seem to be tolerated better by children with leukemia than by adults, who may experience sever neurological toxicity. Administration of the drug more frequently than every 7 days or at higher doses seems to increase the toxic manifestations without proportional improvement in the response rate. Precautions should also be used to avoid extravasation during intravenous administration of vincristine. Vincristine (and vinblastine) can be infused into the arterial blood supply of tumors in doses several times larger than those that can be administered intravenously with comparable toxicity.

Vincristine has been effective in Hodgkin's disease and other lymphomas. Although it appears to be somewhat less beneficial than vinblastine when used alone in Hodgkin's disease, when used with mechlorethamine, prednisolone, and procarbazine (the so-called MOPP regimen), it is the preferred treatment for the advanced stages (III and IV) of this disease. In non-Hodgkin's lymphomas, vincristine is an important agent, particularly when used with cyclophosphamide, bleomycin, doxorubicin, and prednisolone. Vincristine is more useful than vinblastine in lymphocytic leukemia. Beneficial response have been reported in patients with a variety of other neoplasms, particularly Wilms' tumor, neuroblastoma, brain tumors, rhabdomyosarcoma, and carcinomas of the breast, bladder, and the male and female reproductive systems.

Doses of vincristine for use will be determined by the clinician according to the individual patients need. 0.01 to 0.03 mg/kg or 0.4 to 1.4 mg/m$^2$ can be administered or 1.5 to 2 mg/m$^2$ can also be administered. Alternatively 0.02 mg/m$^2$, 0.05 mg/m$^2$, 0.06 mg/m$^2$, 0.07 mg/m$^2$, 0.08 mg/m$^2$, 0.1 mg/m$^2$, 0.12 mg/m$^2$, 0.14 mg/m$^2$, 0.15 mg/m$^2$, 0.2 mg/m$^2$, 0.25 mg/m$^2$ can be given as a constant intravenous infusion. Of course, all of these dosages are exemplary, and any dosage in-between these points is also expected to be of use in the invention.

Vinblastine. When cells are incubated with vinblastine, dissolution of the microtubules occurs. Unpredictable absorption has been reported after oral administration of vinblastine or vincristine. At the usual clinical doses the peak concentration of each drug in plasma is approximately 0.4 mM. Vinblastine and vincristine bind to plasma proteins. They are extensively concentrated in platelets and to a lesser extent in leukocytes and erythrocytes.

After intravenous injection, vinblastine has a multiphasic pattern of clearance from the plasma; after distribution, drug disappears from plasma with half-lives of approximately 1 and 20 hours.

Vinblastine is metabolized in the liver to biologically activate derivative desacetylvinblastine. Approximately 15% of an administered dose is detected intact in the urine, and about 10% is recovered in the feces after biliary excretion. Doses should be reduced in patients with hepatic dysfunction. At least a 50% reduction in dosage is indicated if the concentration of bilirubin in plasma is greater than 3 mg/dl (about 50 mM).

Vinblastine sulfate is available in preparations for injection. The drug is given intravenously; special precautions must be taken against subcutaneous extravasation, since this may cause painful irritation and ulceration. The drug should not be injected into an extremity with impaired circulation. After a single dose of 0.3 mg/kg of body weight, myelosuppression reaches its maximum in 7 to 10 days. If a moderate level of leukopenia (approximately 3000 cells/mm$^3$) is not attained, the weekly dose may be increased gradually by increments of 0.05 mg/kg of body weight. In regimens designed to cure testicular cancer, vinblastine is used in doses of 0.3 mg/kg every 3 weeks irrespective of blood cell counts or toxicity.

The most important clinical use of vinblastine is with bleomycin and cisplatin in the curative therapy of metastatic testicular tumors. Beneficial responses have been reported in various lymphomas, particularly Hodgkin's disease, where significant improvement may be noted in 50 to 90% of cases. The effectiveness of vinblastine in a high proportion of lymphomas is not diminished when the disease is refractory to alkylating agents. It is also active in Kaposi's sarcoma, neuroblastoma, and Letterer-Siwe disease (histiocytosis X), as well as in carcinoma of the breast and choriocarcinoma in women.

Doses of vinblastine for use will be determined by the clinician according to the individual patients need. 0.1 to 0.3 mg/kg can be administered or 1.5 to 2 mg/m$^2$ can also be administered. Alternatively, 0.1 mg/m$^2$, 0.12 mg/m$^2$, 0.14 mg/m$^2$, 0.15 mg/m$^2$, 0.2 mg/m$^2$, 0.25 mg/m$^2$, 0.5 mg/m$^2$, 1.0 mg/m$^2$, 1.2 mg/m$^2$, 1.4 mg/m$^2$, 1.5 mg/m$^2$, 2.0 mg/m$^2$, 2.5 mg/m$^2$, 5.0 mg/m$^2$, 6 mg/m$^2$, 8 mg/m$^2$, 9 mg/m$^2$, 10 mg/m$^2$, 20 mg/m$^2$, can be given. Of course, all of these dosages are exemplary, and any dosage in-between these points is also expected to be of use in the invention.

(iv) Alkylating Agents

Carmustine. Carmustine (sterile carmustine) is one of the nitrosoureas used in the treatment of certain neoplastic diseases. It is 1,3bis (2-chloroethyl)-1-nitrosourea. It is lyophilized pale yellow flakes or congealed mass with a molecular weight of 214.06. It is highly soluble in alcohol and lipids, and poorly soluble in water. Carmustine is administered by intravenous infusion after reconstitution as recommended. Sterile carmustine is commonly available in 100 mg single dose vials of lyophilized material.

Although it is generally agreed that carmustine alkylates DNA and RNA, it is not cross resistant with other alkylators. As with other nitrosoureas, it may also inhibit several key enzymatic processes by carbamoylation of amino acids in proteins.

Carmustine is indicated as palliative therapy as a single agent or in established combination therapy with other approved chemotherapeutic agents in brain tumors such as glioblastoma, brainstem glioma, medullobladyoma, astrocytoma, ependymoma, and metastatic brain tumors. Also it has been used in combination with prednisolone to treat multiple myeloma. Carmustine has proved useful, in the treatment of Hodgkin's Disease and in non-Hodgkin's lymphomas, as secondary therapy in combination with other approved drugs in patients who relapse while being treated with primary therapy, or who fail to respond to primary therapy.

The recommended dose of carmustine as a single agent in previously untreated patients is 150 to 200 mg/m$^2$ intravenously every 6 weeks. This may be given as a single dose or divided into daily injections such as 75 to 100 mg/m$^2$ on 2 successive days. When carmustine is used in combination with other myelosuppressive drugs or in patients in whom bone marrow reserve is depleted, the doses should be adjusted accordingly. Doses subsequent to the initial dose should be adjusted according to the hematologic response of the patient to the preceding dose. It is of course understood that other doses may be used in the present invention for example 10 mg/m$^2$, 20 mg/m$^2$, 30 mg/m$^2$ 40 mg/m$^2$ 50 mg/m$^2$ 60 mg/m$^2$ 70 mg/m$^2$ 80 mg/m$^2$ 90 mg/m$^2$ 100 mg/m$^2$. The skilled artisan is directed to, "Remington's Pharmaceutical Sciences" 15th Edition, chapter 61. Some variation in dosage will necessarily occur depending on the condition of the subject being treated. The person responsible for administration will, in any event, determine the appropriate dose for the individual subject Melphalan. Melphalan also known as alkeran, L-phenylalanine mustard, phenylalanine mustard, L-PAM, or L-sarcolysin, is a phenylalanine derivative of nitrogen mustard. Melphalan is a bifunctional alkylating agent which is active against selective human neoplastic diseases. It is known chemically as 4-[bis(2-chloroethyl)amino]-L-phenylalanine.

Melphalan is the active L-isomer of the compound and was first synthesized in 1953 by Bergel and Stock; the D-isomer, known as medphalan, is less active against certain animal tumors, and the dose needed to produce effects on chromosomes is larger than that required with the L-isomer. The racemic (DL-) form is known as merphalan or sarcolysin. Melphalan is insoluble in water and has a pKa$_1$ of ~2.1. Melphalan is available in tablet form for oral administration and has been used to treat multiple myeloma.

Available evidence suggests that about one third to one half of the patients with multiple myeloma show a favorable response to oral administration of the drug.

Melphalan has been used in the treatment of epithelial ovarian carcinoma. One commonly employed regimen for the treatment of ovarian carcinoma has been to administer melphalan at a dose of 0.2 mg/kg daily for five days as a single course. Courses are repeated every four to five weeks depending upon hematologic tolerance (Smith and Rutledge, 1975; Young et al., 1978). Alternatively the dose of melphalan used could be as low as 0.05 mg/kg/day or as high as 3 mg/kg/day or any dose in between these doses or above these doses. Some variation in dosage will necessarily occur depending on the condition of the subject being treated. The person responsible for administration will, in any event, determine the appropriate dose for the individual subject.

Cyclophosphamide. Cyclophosphamide is 2H-1,3,2-Oxazaphosphorin-2-amine, N,N-bis(2-chloroethyl)tetrahydro-, 2-oxide, monohydrate; termed Cytoxan available from Mead Johnson; and Neosar available from Adria. Cyclophosphamide is prepared by condensing 3-amino-1-propanol with N,N-bis(2-chlorethyl) phosphoramidic dichloride [$(ClCH_2CH_2)_2N$—$POCl_2$] in dioxane solution under the catalytic influence of triethylamine. The condensation is double, involving both the hydroxyl and the amino groups, thus effecting the cyclization.

Unlike other β-chloroethylamino alkylators, it does not cyclize readily to the active ethyleneimonium form until activated by hepatic enzymes. Thus, the substance is stable in the gastrointestinal tract, tolerated well and effective by the oral and parental routes and does not cause local vesication, necrosis, phlebitis or even pain.

Suitable doses for adults include, orally, 1 to 5 mg/kg/day (usually in combination), depending upon gastrointestinal tolerance; or 1 to 2 mg/kg/day; intravenously, initially 40 to 50 mg/kg in divided doses over a period of 2 to 5 days or 10 to 15 mg/kg every 7 to 10 days or 3 to 5 mg/kg twice a week or 1.5 to 3 mg/kg/day. A dose 250 mg/kg/day may be administered as an antineoplastic. Because of gastrointestinal adverse effects, the intravenous route is preferred for loading. During maintenance, a leukocyte count of 3000 to 4000/mm$^3$ usually is desired. The drug also sometimes is administered intramuscularly, by infiltration or into body cavities. It is available in dosage forms for injection of 100, 200 and 500 mg, and tablets of 25 and 50 mg the skilled artisan is referred to "Remington's Pharmaceutical Sciences" 15th Edition, chapter 61, incorporate herein as a reference, for details on doses for administration.

Chlorambucil. Chlorambucil (also known as leukeran) was first synthesized by Everett et al. (1953). It is a bifunctional alkylating agent of the nitrogen mustard type that has been found active against selected human neoplastic diseases. Chlorambucil is known chemically as 4-[bis(2-chlorethyl) amino] benzenebutanoic acid.

Chlorambucil is available in tablet form for oral administration. It is rapidly and completely absorbed from the gastrointestinal tract. After single oral doses of 0.6-1.2 mg/kg, peak plasma chlorambucil levels are reached within one hour and the terminal half-life of the parent drug is estimated at 1.5 hours. 0.1 to 0.2 mg/kg/day or 3 to 6 mg/m$^2$/day or alternatively 0.4 mg/kg may be used for antineoplastic treatment. Treatment regimes are well know to those of skill in the art and can be found in the "Physicians Desk Reference" and in "Remingtons Pharmaceutical Sciences" referenced herein.

Chlorambucil is indicated in the treatment of chronic lymphatic (lymphocytic) leukemia, malignant lymphomas including lymphosarcoma, giant follicular lymphoma and Hodgkin's disease. It is not curative in any of these disorders but may produce clinically useful palliation.

Busulfan. Busulfan (also known as myleran) is a bifunctional alkylating agent. Busulfan is known chemically as 1,4-butanediol dimethanesulfonate.

Busulfan is not a structural analog of the nitrogen mustards. Busulfan is available in tablet form for oral administration. Each scored tablet contains 2 mg busulfan and the inactive ingredients magnesium stearate and sodium chloride.

Busulfan is indicated for the palliative treatment of chronic myelogenous (myeloid, myelocytic, granulocytic) leukemia. Although not curative, busulfan reduces the total granulocyte mass, relieves symptoms of the disease, and improves the clinical state of the patient. Approximately 90% of adults with previously untreated chronic myelogenous leukemia will obtain hematologic remission with regression or stabilization of organomegaly following the use of busulfan. It has been shown to be superior to splenic irradiation with respect to survival times and maintenance of hemoglobin levels, and to be equivalent to irradiation at controlling splenomegaly.

Lomustine. Lomustine is one of the nitrosoureas used in the treatment of certain neoplastic diseases. It is 1-(2-chloroethyl)-3-cyclohexyl-1 nitrosourea. It is a yellow powder with the empirical formula of $C_9H_{16}ClN_3O_2$ and a molecular weight of 233.71. Lomustine is soluble in 10% ethanol (0.05 mg per mL) and in absolute alcohol (70 mg per mL). Lomustine is relatively insoluble in water (<0.05 mg per mL). It is relatively unionized at a physiological pH. Inactive ingredients in lomustine capsules are: magnesium stearate and mannitol.

Although it is generally agreed that lomustine alkylates DNA and RNA, it is not cross resistant with other alkylators. As with other nitrosoureas, it may also inhibit several key enzymatic processes by carbamoylation of amino acids in proteins.

Lomustine may be given orally. Following oral administration of radioactive lomustine at doses ranging from 30 mg/m$^2$ to 100 mg/m$^2$, about half of the radioactivity given was excreted in the form of degradation products within 24 hours.

The serum half-life of the metabolites ranges from 16 hours to 2 days. Tissue levels are comparable to plasma levels at 15 minutes after intravenous administration.

Lomustine has been shown to be useful as a single agent in addition to other treatment modalities, or in established combination therapy with other approved chemotherapeutic agents in both primary and metastatic brain tumors, in patients who have already received appropriate surgical and/or radiotherapeutic procedures. It has also proved effective in secondary therapy against Hodgkin's Disease in combination with other approved drugs in patients who relapse while being treated with primary therapy, or who fail to respond to primary therapy.

The recommended dose of lomustine in adults and children as a single agent in previously untreated patients is 130 mg/m$^2$ as a single oral dose every 6 weeks. In individuals with compromised bone marrow function, the dose should be reduced to 100 mg/m$^2$ every 6 weeks. When lomustine is used in combination with other myelosuppressive drugs, the doses should be adjusted accordingly. It is understood that other doses may be used for example, 20 mg/m$^2$, 30 mg/m$^2$, 40 mg/m$^2$, 50 mg/m$^2$, 60 mg/m$^2$, 70 mg/m$^2$, 80 mg/m$^2$, 90 mg/m$^2$, 100 mg/m$^2$, 120 mg/m$^2$ or any doses between these figures as determined by the clinician to be necessary for the individual being treated.

E. Adjunct Cancer Therapies

In order to increase the effectiveness of the combination therapy with the CDDO-compounds as described in the present invention, it may be desirable to combine these compositions with yet other agents effective in the treatment of cancer such as but not limited to those described below.

a) Radiotherapeutic Agents

Radiotherapeutic agents and factors include radiation and waves that induce DNA damage for example, γ-irradiation, X-rays, UV-irradiation, microwaves, electronic emissions, radioisotopes, and the like. Therapy may be achieved by irradiating the localized tumor site with the above described forms of radiations. It is most likely that all of these factors effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

b) Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

c) Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. Immunotherapy could be used as part of a combined therapy, in conjunction with the CDDO-compounds-based therapy.

The general approach for combined therapy is discussed below. In one aspect the immunotherapy can be used to target a tumor cell. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. Alternate immune stimulating molecules also exist including: cytokines such as IL-2, IL-4, IL-12, GM-CSF, gamma-IFN, chemokines such as MIP-1, MCP-1, IL-8 and growth factors such as FLT3 ligand. Combining immune stimulating molecules, either as proteins or using gene delivery in combination with the CDDO-compound based combination therapy of this invention will enhance anti-tumor effects.

(i) Passive Immunotherapy

A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

(ii) Active Immunotherapy

In active immunotherapy, an antigenic peptide, polypeptide or protein, or an autologous or allogenic tumor cell composition or "vaccine" is administered, generally with a distinct bacterial adjuvant (Ravindranath & Morton, 1991; Morton & Ravindranath, 1996; Morton et al., 1992; Mitchell et al., 1990; Mitchell et al., 1993).

(iii) Adoptive Immunotherapy

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). To achieve this, one would administer to an animal, or human patient, an immunologically effective amount of activated lymphocytes in combination with an adjuvant-incorporated antigenic peptide composition as described herein. The activated lymphocytes will most preferably be the patient's own cells that were earlier isolated from a blood or tumor sample and activated (or "expanded") in vitro.

d) Gene Therapy

In yet another embodiment, gene therapy in conjunction with the combination therapy using the CDDO-compounds described in the invention are contemplated. A variety of proteins are encompassed within the invention, some of which are described below. Table 1 lists various genes that may be targeted for gene therapy of some form in combination with the present invention.

TABLE 1

| Gene | Source | Human Disease | Function |
|---|---|---|---|
| Growth Factors | | | |
| HST/KS | Transfection | | FGF family member |
| INT-2 | MMTV promoter Insertion | | FGF family member |
| INTI/WNTI | MMTV promoter Insertion | | Factor-like |
| SIS | Simian sarcoma virus | | PDGF B |

TABLE 1-continued

| Gene | Source | Human Disease | Function |
|---|---|---|---|
| Receptor Tyrosine Kinases | | | |
| ERBB/HER | Avian erythroblastosis virus; ALV promoter insertion; amplified human tumors | Amplified, deleted squamous cell cancer; glioblastoma | EGF/TGF-α/ Amphiregulin/ Hetacellulin receptor |
| ERBB-2/NEU/HER-2 | Transfected from rat Glioblastomas | Amplified breast, ovarian, gastric cancers | Regulated by NDF/ Heregulin and EGF-Related factors |
| FMS | SM feline sarcoma virus | | CSF-1 receptor |
| KIT | HZ feline sarcoma virus | | MGF/Steel receptor Hematopoicis |
| TRK | Transfection from human colon cancer | | NGF (nerve growth Factor) receptor |
| MET | Transfection from human osteosarcoma | | Scatter factor/HGF Receptor |
| RET | Translocations and point mutations | Sporadic thyroid cancer; familial medullary thyroid cancer; multiple endocrine neoplasias 2A and 2B | Orphan receptor Tyr Kinase |
| ROS | URII avian sarcoma Virus | | Orphan receptor Tyr Kinase |
| PDGF receptor | Translocation | Chronic Myelomonocytic Leukemia | TEL(ETS-like transcription factor)/ PDGF receptor gene Fusion |
| TGF-βreceptor | | Colon carcinoma mismatch mutation target | |
| NONRECEPTOR TYROSINE KINASES | | | |
| ABL | Abelson Mul. V | Chronic myelogenous leukemia translocation with BCR | Interact with RB, RNA polymerase, CRK, CBL |
| FPS/FES | Avian Fujinami SV;GA FeSV | | |
| LCK | Mul.V (murine leukemia virus) promoter insertion | | Src family; T cell signaling; interacts CD4/CD8 T cells |
| SRC | Avian Rous sarcoma Virus | | Membrane-associated Tyr kinase with signaling function; activated by receptor kinases |
| YES | Avian Y73 virus | | Src family; signaling |
| SER/THR PROTEIN KINASES | | | |
| AKT | AKT8 murine retrovirus | | Regulated by PI(3)K?; regulate 70-kd S6 k? |
| MOS | Maloney murine SV | | GVBD; cystostatic factor; MAP kinase kinase |
| PIM-1 | Promoter insertion Mouse | | |
| RAF/MIL | 3611 murine SV; MH2 avian SV | | Signaling in RAS Pathway |
| MISCELLANEOUS CELL SURFACE[1] | | | |
| APC | Tumor suppressor | Colon cancer | Interacts with catenins |
| DCC | Tumor suppressor | Colon cancer | CAM domains |
| E-cadherin | Candidate tumor Suppressor | Breast cancer | Extracellular homotypic binding; intracellular interacts with catenins |
| PTC/NBCCS | Tumor suppressor and Drosophilia homology | Nevoid basal cell cancer syndrome (Gorline syndrome) | 12 transmembrane domain; signals through Gli homogue CI to antagonize hedgehog pathway |
| TAN-1 Notch homologue | Translocation | T-ALL | Signaling? |
| MISCELLANEOUS SIGNALING | | | |
| BCL-2 | Translocation | B-cell lymphoma | Apoptosis |
| CBL | Mu Cas NS-1 V | | Tyrosine-Phosphorylated RING finger interact Abl |

TABLE 1-continued

| Gene | Source | Human Disease | Function |
|---|---|---|---|
| CRK | CT1010 ASV | | Adapted SH2/SH3 interact Abl |
| DPC4 | Tumor suppressor | Pancreatic cancer | TGF-β-related signaling Pathway |
| MAS | Transfection and Tumorigenicity | | Possible angiotensin Receptor |
| NCK | | | Adaptor SH2/SH3 |
| GUANINE NUCLEOTIDE EXCHANGERS AND BINDING PROTEINS | | | |
| BCR | | Translocated with ABL in CML | Exchanger; protein Kinase |
| DBL | Transfection | | Exchanger |
| GSP | | | |
| NF-1 | Hereditary tumor Suppressor | Tumor suppressor neurofibromatosis | RAS GAP |
| OST | Transfection | | Exchanger |
| Harvey-Kirsten, N-RAS | HaRat SV; Ki RaSV; Balb-MoMuSV; Transfection | Point mutations in many human tumors | Signal cascade |
| VAV | Transfection | | S112/S113; exchanger |
| NUCLEAR PROTEINS AND TRANSCRIPTION FACTORS | | | |
| BRCA1 | Heritable suppressor | Mammary cancer/ovarian cancer | Localization unsettled |
| BRCA2 | Heritable suppressor | Mammary cancer | Function unknown |
| ERBA | Avian erythroblastosis Virus | | thyroid hormone receptor (transcription) |
| ETS | Avian E26 virus | | DNA binding |
| EVII | MuLV promotor Insertion | AML | Transcription factor |
| FOS | FBI/FBR murine osteosarcoma viruses | | 1 transcription factor with c-JUN |
| GLI | Amplified glioma | Glioma | Zinc finger; cubitus interruptus homologue is in hedgehog signaling pathway; inhibitory link PTC and hedgehog |
| HMGI/LIM | Translocation t(3;12) t(12;15) | Lipoma | Gene fusions high mobility group HMGI-C (XT-hook) and transcription factor LIM or acidic domain |
| JUN | ASV-17 | | Transcription factor AP-1 with FOS |
| MLL/VHRK+ELI/MEN | Translocation/fusion ELL with MLL Trithorax-like gene | Acute myeloid leukemia | Gene fusion of DNA-binding and methyl transferase MLL with ELI RNA pol II elongation factor |
| MYB | Avian myeloblastosis Virus | | DNA binding |
| MYC | Avian MC29; Translocation B-cell Lymphomas; promoter Insertion avian leukosis Virus | Burkitt's lymphoma | DNA binding with MAX partner; cyclin regulation; interact RB?; regulate apoptosis? |
| N-MYC | Amplified | Neuroblastoma | |
| L-MYC | | Lung cancer | |
| REL | Avian Retriculoendotheliosis Virus | | NF-κB family transcription factor |
| SKI | Avian SKV770 Retrovirus | | Transcription factor |
| VHL | Heritable suppressor | Von Hippel-Landau syndrome | Negative regulator or elongin; transcriptional elongation complex |
| WT-1 | | Wilm's tumor | Transcription factor |
| CELL CYCLE/DNA DAMAGE RESPONSE[10-21] | | | |
| ATM | Hereditary disorder | Ataxia-telangiectasia | Protein/lipid kinase homology; DNA damage response upstream in P53 pathway |
| BCL-2 | Translocation | Follicular lymphoma | Apoptosis |

TABLE 1-continued

| Gene | Source | Human Disease | Function |
|---|---|---|---|
| FACC | Point mutation | Fanconi's anemia group C (predisposition leukemia | |
| MDA-7 | Fragile site 3p14.2 | Lung carcinoma | Histidine triad-related diadenosine 5',3''''-tetraphosphate asymmetric hydrolase |
| hMLI/MutL | | HNPCC | Mismatch repair; MutL Homologue |
| hMSH2/MutS | | HNPCC | Mismatch repair; MutS Homologue |
| hPMS1 | | HNPCC | Mismatch repair; MutL Homologue |
| hPMS2 | | HNPCC | Mismatch repair; MutL Homologue |
| INK4/MTS1 | Adjacent INK-4B at 9p21; CDK complexes | Candidate MTS1 suppressor and MLM melanoma gene | p16 CDK inhibitor |
| INK4B/MTS2 | | Candidate suppressor | p15 CDK inhibitor |
| MDM-2 | Amplified | Sarcoma | Negative regulator p53 |
| p53 | Association with SV40 T antigen | Mutated > 50% human tumors, including hereditary Li-Fraumeni syndrome | Transcription factor; checkpoint control; apoptosis |
| PRAD1/BCL1 | Translocation with Parathyroid hormone or IgG | Parathyroid adenoma; B-CLL | Cyclin D |
| RB | Hereditary Retinoblastoma; Association with many DNA virus tumor Antigens | Retinoblastoma; osteosarcoma; breast cancer; other sporadic cancers | Interact cyclin/cdk; regulate E2F transcription factor |
| XPA | | xerodema pigmentosum; skin cancer predisposition | Excision repair; photo-product recognition; zinc finger | e) Other Agents

It is contemplated that other agents may be used in combination with the present invention to improve the therapeutic efficacy of treatment. One form of therapy for use in conjunction with chemotherapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention. The use of hormones may be employed in the treatment of certain cancers such as breast, prostate, ovarian, or cervical cancer to lower the level or block the effects of certain hormones such as testosterone or estrogen and this often reduces the risk of metastases.

F. Vectors that Express Bcl-2

Within certain embodiments, expression vectors are employed to exogenously express a Bcl-2 polypeptide product in cells, especially lymphoid cells. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

(i) Regulatory Elements

Throughout this application, the term "expression construct" is meant to include any type of genetic construct containing a nucleic acid coding for a gene product in which part or all of the nucleic acid encoding sequence is capable of being transcribed and translated into a polypeptide product. An "expression cassette" is defined as a nucleic acid encoding a gene product under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In certain embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 2 and 3 list several regulatory elements that may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 2 and Table 3). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 2

| Promoter and/or Enhancer | |
|---|---|
| Promoter/Enhancer | References |
| Immunoglobulin Heavy Chain | Banerji et al., 1983; Gilles et al., 1983; Grosschedl et al, 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986, Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |

TABLE 2-continued

| Promoter and/or Enhancer | |
|---|---|
| Promoter/Enhancer | References |
| Neural Cell Adhesion Molecule (NCAM) | Hirsh et al., 1990 |
| α$_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

| Inducible Elements | | |
|---|---|---|
| Element | Inducer | References |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| CRP | IL-6, IL-1 | Ku & Mortensen, 1993 |
| SAA | IL-6, IL-1 | Jiang et al., 1995 |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |

TABLE 3-continued

Inducible Elements

| Element | Inducer | References |
| --- | --- | --- |
| Proliferin | Phorbol Ester-TPA | Mordacq et al., 1989 |
| Tumor Necrosis Factor | TPA | Hensel et al., 1989 |
| Thyroid Stimulating Hormone αGene | Thyroid Hormone | Chatterjee et al., 1989 |

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

(ii) Selectable Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(iii) Polyadenylation Signals

In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

(iv) Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Thus, in the present invention a Bcl-2 from any cell may be expressed in a lymphoid cell that normally does not express Bcl-2. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (1989) and Ausubel et al. (1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

(v) Delivery of Expression Vectors

There are a number of ways in which expression vectors may be introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

Adenovirus. One of the methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell innoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{12}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus & Horwitz, 1992; Graham and Prevec, 1991). Recently, animal studies suggested that recombinant adenovirus could be used for gene therapy (Stratford-Perricaudet & Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

Retrovirus. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Adeno-Associated Viruses. Adeno-associated virus (AAV) is an attractive virus for delivering foreign genes to mammalian subjects (Ridgeway, 1988; Baichwal and Sugden, 1986; Hermonat and Muzycska, 1984). AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription. The sequence of AAV is provided by U.S. Pat. No. 5,252,479 (entire text of which is specifically incorporated herein by reference).

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of the AAV vector of the present invention can be obtained by restriction endonuclease digestion of AAV or a plasmid such as p201, which contains a modified AAV genome (Samulski et al., 1987). Alternatively, the terminal repeats may be obtained by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

Other Viruses. Other viral vectors may be employed as expression constructs in the present invention. Vectors derived from viruses such as vaccinia virus (Ridgeway, 1988; Baichwal and Sugden, 1986; Coupar et al., 1988) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

Non-Viral Methods. Several non-viral methods for the transfer of expression constructs into mammalian cells also are contemplated by the present invention. These include DEAE-dextran (Gopal, 1985), electroporation (Tur-Kaspa et al., 1986; Potter et al., 1984), direct microinjection (Harland and Weintraub, 1985), lipofectamine-DNA complexes, cell sonication (Fechheimer et al., 1987), and receptor-mediated transfection (Wu and Wu, 1987; Wu and Wu, 1988).

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Liposomes. In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are Lipofectamine®-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0 273 085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes. For example, epidermal growth factor (EGF) may be used as the receptor for mediated delivery of a nucleic acid into cells that exhibit upregulation of EGF receptor. Mannose can be used to target the mannose receptor on liver cells.

G. Pharmaceutical Formulations and Delivery

In a preferred embodiment of the present invention, a method of treatment for a cancer by administering to a cancer cell CDDO-compound and a chemotherapeutic agent, wherein the combination of the CDDO-compound with the chemotherapeutic agent is effective in inducing cytotoxicity in said cell An effective amount of the pharmaceutical composition, generally, is defined as that amount sufficient to detectably and repeatedly to ameliorate, reduce, minimize or limit the extent of the disease or its symptoms. More rigorous definitions may apply, including elimination, eradication or cure of disease.

The routes of administration will vary, naturally, with the location and nature of the lesion, and include, e.g., intradermal, transdermal, parenteral, intravenous, intra-arterial, intramuscular, intranasal, subcutaneous, percutaneous, intratracheal, intraperitoneal, intratumoral, perfusion, lavage, direct injection, ex vivo bone marrow or blood cell purging, and oral administration and formulation. Intratumoral injection, or injection into the tumor vasculature is specifically contemplated for discrete, solid, accessible tumors. Local, regional or systemic administration also may be appropriate. In the case of surgical intervention, the present invention may be used before surgery, at the time of surgery, and/or thereafter, to treat residual or metastatic disease. For example, a resected tumor bed may be injected or perfused with a formulation comprising the combination of the CDDO-compound and other chemotherapeutic therapy of this invention. The perfusion may be continued post-resection, for example, by leaving a catheter implanted at the site of the surgery. Periodic post-surgical treatment also is envisioned. Ex vivo purging is an important method of administration that is contemplated.

Continuous administration also may be applied where appropriate, for example, where a tumor is excised and the tumor bed is treated to eliminate residual, microscopic disease. Delivery may be via syringe or catherization. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs. It is further contemplated that limb perfusion may be used to administer therapeutic compositions of the present invention, particularly in the treatment of melanomas and sarcomas.

Treatment regimens may vary as well, and often depend on tumor type, tumor location, disease progression, and health and age of the patient. Obviously, certain types of tumors will require more aggressive treatment, while at the same time, certain patients cannot tolerate more taxing protocols. The clinician will be best suited to make such decisions based on the known efficacy and toxicity (if any) of the therapeutic formulations.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vaccuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

H. Clinical Trials

This section is concerned with the development of human treatment protocols for anticancer therapy using the CDDO-compounds in combination with other chemotherapeutic agents and/or immunosuppressive agents.

The various elements of conducting a clinical trial, including patient treatment and monitoring, will be known to those of skill in the art in light of the present disclosure. The following information is being presented as a general guideline for use in establishing the CDDO-compound based combination therapies described herein alone or in combinations with other adjunct treatments used routinely in cancer therapy in clinical trials.

Candidates for the phase 1 clinical trial will be patients on which all conventional therapies have failed. Approximately 100 patients will be treated initially. Their age will range from 16 to 90 (median 65) years. Patients will be treated, and samples obtained, without bias to sex, race, or ethnic group. For this patient population of approximately 41% will be women, 6% will be black, 13% Hispanic, and 3% other minorities. These estimates are based on consecutive cases seen at MD Anderson Cancer Center over the last 5 years.

Optimally the patient will exhibit adequate bone marrow function (defined as peripheral absolute granulocyte count of >2,000/mm$^3$ and platelet count of 100,000/mm$^3$, adequate liver function (bilirubin 1.5 mg/dl) and adequate renal function (creatinine 1.5 mg/dl).

Research samples will be obtained from peripheral blood or marrow under existing IRB approved projects and protocols. Some of the research material will be obtained from specimens taken as part of patient care.

The subacute and chronic toxicity studies, pharmacokinetics and tissue distribution studies (described in the section entitled Examples) provide the critical information necessary to generate and have approved an Investigational New Drug (IND) for the CDDO-compound-chemotherapeutic agent combination therapy described in this invention for clinical studies in leukemia and other cancer patients.

The combination treatments described above will be administered to the patients regionally or systemically on a tentative weekly basis. A typical treatment course may comprise about six doses delivered over a 7 to 21 day period. Upon election by the clinician the regimen may be continued with six doses every three weeks or on a less frequent (monthly, bimonthly, quarterly etc.) basis. Of course, these are only exemplary times for treatment, and the skilled practitioner will readily recognize that many other time-courses are possible.

The modes of administration may be local administration, including, by intratumoral injection and/or by injection into tumor vasculature, intratracheal, endoscopic, subcutaneos, and/or percutaneous. The mode of administration may be systemic, including, intravenous, intra-arterial, intra-peritoneal and/or oral administration.

In one embodiment, CDDO and retinoids will be administered. In other embodiments, CDDO-Me and retinoids will be administered.

CDDO will be administered at dosages in the range of 5-30 mg/kg intravenously or 5-100 mg/kg orally. CDDO-Me will be administered in the range of 5-100 mg/kg intravenously or 5-100 mg/kg orally for 3-30 days. The retinoid may be all-trans-retinoic acid (ATRA), 9-cis-retinoic acid, LG100268, LGD1069 (Targretin, bexarotene), fenretinide [N-(4-hydroxyphenyl)retinamide, 4-HPR], CD437 or any RXR- or RAR-specific retinoic acid. The retinoids may be administered orally, intravenously, by topical application or by other routes. In some embodiments the retinoids are liposomal formulations. For example, a liposomal formulation of ATRA is administered a range of 10-100 mg/m$^2$/day intravenously. Thus, one may administer to a patient 10, 20, 25, 30, 35, 40, 45, 50, 55, 60, 65, 70, 75, 80, 85, 90, 95, or 100 mg/m$^2$/day of a liposomal formulation of ATRA. Non-liposomal ATRA may be administered orally in the range of 10-100 mg/m$^2$/day. Thus, one may administer to a patient 10, 20, 25, 30, 35, 40, 45, 50, 55, 60, 65, 70, 75, 80, 85, 90, 95, or 100 mg/m$^2$/day of ATRA orally. 9-cis-Retinoid acid may be administered in the range of 20-150 mg/m$^2$ twice a day orally. Thus, one may administer 20, 25, 30, 35, 40, 45, 50, 55, 60, 65, 70, 75, 80, 85, 90, 95, 100, 105, 110, 115, 120, 125, 130, 135, 140, 145, or 150 mg/m$^2$ of 9-cis-retinoid. LG100268 is be effective in a dose range of 5-50 mg/kg. Thus, 5, 10, 15, 20, 25, 30, 35, 40, 45, to 50 mg/kg of LG100268 may be administered to a patient. LGD1069 (Targretin, bexarotene) capsules are contemplated for the topical treatment of cutaneous lesions in patients with cutaneous T-cell lymphoma (CTCL) who have refractory or resistant disease after other therapies. The dose ranges of these capsules is 300-400 mg/m$^2$/day orally. LGD1069 gel at 1% may also be used for the topical treatment of cutaneous lesions in patients with CTCL (Stage (1A and 1B) who have refractory or resistant disease after other therapies; two to four times daily. Fenretinide [N-(4-hydroxyphenyl)retinamide, 4-HPR] is contemplated useful at 25-600 mg daily and the administration in some embodiments may be continuous. Of course, the skilled artisan will understand that while these dosage ranges, provide useful guidelines appropriate adjustments in the dosage depending on the needs of an individual patient factoring in disease, gender, age and other general health conditions will be made at the time of administration to a patient by a trained physician. The same is true for means of admintration, routes of administration as well.

In yet other embodiments, CDDO-compounds and other chemotherapeutic drugs such as Doxorubicin, Mylotarg, Dolastatin-10, Bryostatin or any other chemotherapeutic drug used in cancer therapy will be administered to patients in need thereof. Some exemplary doses and routes of various chemotherapeutics are listed here: Taxol is usually administered by IV at one dose of 130-250 mg/m$^2$ every 3 weeks, Vincristine is usually administered by IV at one dose of 1-1.4 mg/m$^2$ every week, Vinblastine is usually given by IV at one dose of 6 mg/m$^2$ every week, or at a dose of 2 mg/m$^2$ as a continuous infusion for 5 days every 3 weeks, VP-16 (etoposide) is usually administered by IV at 75-100 mg/m$^2$ every day for 5 days, or orally at a dose of 200 mg/m$^2$ for 2 days every week, Actinomycin D is usually administered by IV at one dose of 0.6 mg/m$^2$ every day for 5 days, Doxorubicin is typically administered by IV at one dose of 75 mg/m$^2$ every 3 weeks, or at a dose of 20 mg/m$^2$ every week, Daunorubicin is usually administered by IV at a dose of 30 mg/m$^2$ for 3 days every 3 weeks, liposomal Daunorubicin 40-100 mg/m$^2$ every day for 3 days, Idarubicin is usually administered by IV at a dose of 13 mg/m$^2$ every day for 3 days, Mitomycin-C is usually administered by IV at a dose of 10 mg/m$^2$ every day for 3 days, and is repeated every 3 weeks, Actinomycin D IV 0.3-06 mg/m$^2$ every day for 5 days, Bleomycin can be administered by IV, IM, or SC at one dose of 2-15 mg/m$^2$ every week, Methrotrexate may be administered by IV or IM at a dose of 25 mg/m$^2$ twice weekly, it may also be administered in a high dose of >500 mg/m$^2$ every 3 weeks in conjunction with IV leucovorin at a dose of 15 mg/m$^2$ every 6 hours for 7 doses, Cisplatin is typically administered IV 20-40 mg/m$^2$ every day for 5 days, or IV 50-100 mg/m$^2$ every 3-4 weeks, Taxol IV 130-250 mg/m$^2$ every 3 weeks, or 750 mg/m$^2$ every 3 weeks, 5-Fluorouracil can be administered by IV at a dose of 500 mg/m$^2$ every week or for 5 days every 4 weeks, it can also be administered by IV at a dose of 800-1200 mg/m$^2$ every 3-4 weeks. Another administration method is intraarterial (IA) at a dose of 800-1200 mg/m$^2$ every day for 14-21 days. 5-Fluorouracil can also be administered IV at a dose of 375-600 mg/m$^2$ once every week for 6 weeks in conjunction with IV leucovorin at a dose of 500 mg/m$^2$ once every week for 6 weeks. Cytarabine can be administered by IV at a dose of 100 mg/m$^2$ every 12 hours for 5-10 days or by continuous infusion. Hydroxyurea can be administered by IV at a dose of 1000-1500 mg/m$^2$ every day for 5 days or orally at a dose of 1000 mg/m$^2$ every day. Fludarabine can be administered by IV at a dose of 25 mg/m$^2$ every day for 5 days. Cyclophosphamide IV 400 mg/m$^2$ bolus every day for 5 days; Orally 100-300 mg every day for 14 days. Carmusitin (BCNU) 200-225 mg/m$^2$ once every 6 weeks. Melphalan IV 8 mg/m$^2$ every day for 5 days; orally 4 mg/m$^2$ daily. Chlorambucil orally 1-3 mg/m$^2$ daily. Busulfan orally 2-6 mg/m$^2$ daily. Lomustine (CCNU) orally 100-150 mg/m$^2$ once every 6 weeks. TRAIL is another biotherapeutic agent that may be used in conjunction with the CDDO-compounds presented herein. TRAIL is a member of tumor necrosis factor family of cytokines. Trials in humans are underway, so the exact MTD is not known at this point. In mice, daily injections of 200-1000 μg of TRAIL (14 days) significantly increased survival of tumor-bearing mice (see Walczak et al., 1999). Combination of 250-500 μg of TRAIL synergistically enhanced effect of chemotherapy in mice bearing human colon carcinoma tumors (Gliniak et al., 1999). Thus, the inventors contemplate using Dolastatin-10 IV 300-2000 μg/m$^2$ every 3 weeks. Bryostatin IV 12.5-50 μg/m$^2$ every 2 weeks. Liposomal Annamycin IV 100-350 mg/m$^2$ every day for 3 days. Mylotarg IV 4.5-9 mg/m$^2$ every 4 weeks. The present inventors also contemplate using chemotherapeutics that are differentiating agents such as Sodium Phenylacetate (NAPA) at a dose of 200-600 mg/kg/day IV continuous infusion for 14 days and/or Sodium Butyrate (NAPB)-500-2000 mg/kg/day for 7 days IV continuous infusion, SAHA or other histone deacetylase inhibitors.

A description of dosage ranges and routes of administration for other chemotherapeutics is also presented in the section on cancer therapies. It will be understood that the exact dose, frequency and route of administration of the combination therapies of this invention will be determined by one of skill in the art taking into account the age, sex, type of cancer, and other health factors of the individual patient.

To monitor disease course and evaluate the cancer cell killing it is contemplated that the patients should be examined for appropriate tests every month. To assess the effectiveness of the drug, the physician will determine parameters to be monitored depending on the type of cancer/tumor and will involve methods to monitor reduction in tumor mass by for example computer tomography (CT) scans, detection of the presense of the PSA (prostrate specific antigen) in prostrate cancer, HCG in germ tumor and the like. Tests that will be used to monitor the progress of the patients and the effectiveness of the treatments include: physical exam, X-ray, blood work, bone marrow work and other clinical laboratory methodologies. The doses given in the phase 1 study will be escalated as is done in standard phase 1 clinical phase trials, i.e., doses will be escalated until maximal tolerable ranges are reached.

Clinical responses may be defined by acceptable measure. For example, a complete response may be defined by complete disappearance of the leukemia or cancer cells, whereas a partial response may be defined by a 50% reduction of leukemia or cancer cells.

The typical course of treatment will vary depending upon the individual patient and disease being treated in ways known to those of skill in the art. For example, a patient with AML might be treated in four week cycles, although longer duration may be used if no adverse effects are observed with the patient, and shorter terms of treatment may result if the patient does not tolerate the treatment as hoped. This treatment may be repeated for 6-24 months.

I. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Reagents. Stock solutions of CDDO and/or CDDO-Me at 10 mM in DMSO were stored at −20° C. Working solutions were prepared in DMSO and added directly to culture medium. ATRA was purchased from Sigma Chemical Co. (St. Louis, Mo.) and kept in 100% ethanol solution at −20° C. RXR-specific ligand LG-100268 was kindly provided by Dr. Richard Heyman. Caspase-3 inhibitor Z-DEVD-fmk and bongkrekic acid (BA) were obtained from Calbiochem (La Jolla, Calif.). Cyclosporin A (CyA) was purchased from Sandoz. Fas-signaling antibody CH11 and Fas-blocking antibody ZB4 were obtained from Immunotech (Miami, Fla.).

Cell lines. HL-60, KG-1, U937, and Jurkat cell lines were obtained from the American Type Culture Collection (Rockville, Md.). NB4 cells were kindly provided by Dr. M. Lanotte. HL-60-doxorubicin-resistant cells (HL-60-DOX) were also used. U937/Bcl-2 and its appropriate vector controls (U937/pCEP) were provided by Dr. S. Grant. U937 cells were transfected with WT, S70A, or S70E cDNA containing cytomegalovirus plasmids by electroporation (200 V, 975 μF capacitance) and selected and maintained in the medium plus 500 μg/mL G418 (Gibco BRL, Gaithersburg, Md.)

Subjects. Samples of bone marrow or peripheral blood were obtained for in vitro studies from patients with newly diagnosed or recurrent AML with high (>70%) blast count and from patients with myeloid transformation of chronic myeloid leukemia (CML). Informed consent was obtained following institutional guidelines. Mononuclear cells were separated by Ficoll-Hypaque (Sigma Chemical Co) density-gradient centrifugation.

Suspension culture of leukemic cells. Leukemic cell lines were cultured at a density of $3.0 \times 10^5$ cells/mL, and AML mononuclear cells at $5 \times 10^5$ cells/mL in the presence or absence of indicated concentrations of CDDO-Me. Appropriate amounts of DMSO (final concentration <0.05%) was included as a control. For cytotoxicity studies, 1 μM ara-C was added to the cultures. After 24-72 hours, viable cells were counted with the Trypan blue-dye exclusion method using a hematocytometer.

Cell kinetic and DNA fragmentation studies. The cell cycle kinetics was determined by staining cells with acridine orange for cellular DNA and RNA content followed by flow cytometeric analysis as described. Samples were measured in a FACScan flow cytometer (Becton Dickinson, San Jose, Calif.) using the 488-nm line of a 15-nm argon laser and filter settings for green (530 nm) (DNA) and red (585 nm) (RNA) fluorescence. Ten thousand events were stored in list mode for analysis. The percentage of cells in the "sub $G_1$ peak" defined the proportion of apoptotic cells in the tested populations. Cell debris was defined as events in the lowest 10% range of fluorescence, and these results were eliminated from analysis. Cell-cycle kinetics was analyzed using ModFit software (Verity Software House, Inc., Topsham, Me.).

AML blast colony assay. A previously described method was used to measure AML blast colony formation. Briefly, $1 \times 10^5$ T-cell-depleted, nonadherent, low-density bone marrow cells were plated in 0.8% methylcellulose in Iscove's modified Dulbecco's medium (IMDM; Gibco Laboratories, Grand Island, N.Y.) supplemented with 10% fetal bovine serum and 15 ng/mL recombinant human granulocyte-macrophage colony-stimulating factor (hGM-CSF). CDDO or CDDO-Me was added at the initiation of cultures at concentrations ranging from 0.05 to 0.5 µg/mL. AML blast colonies were evaluated under a microscope on day 7 of culture in duplicate dishes.

CFU-Granulocyte-Erythroid-Macrophage-Megakaryocyte (CFU-GEMM) Assay. In three experiments, $2 \times 10^5$ CD34$^+$cells isolated from normal bone marrow (n=1) or G-CSF-stimulated peripheral blood (n=2) were plated in 0.8% methylcellulose with IMDM, 1 U/mL human erythropoietin (Terry Fox Laboratories, Vancouver, Canada), and 50 ng/mL recombinant hGM-CSF. CDDO-Me was added at the initiation of cultures at concentrations ranging from 0.05 to 0.5 µg/mL. All cultures were evaluated after 14 days for the number of burst forming unit-erythroid (BFU-E) colonies, defined as aggregate of more than 500 hemoglobinized cells or three or more erythroid subcolonies and CFU-GM colonies, defined as a cluster of 40 or more granulocytes, monocyte-macrophages or both.

Western blot analysis. An equal amount of protein lysate was placed on 12% SDS-PAGE for 2 hours at 100 volts, followed by transfer of the protein to a Nytran membrane (S&S, Heween, N.H.) and immunoblotting. Polyclonal rabbit antibodies to Bcl-2, Bcl-X$_L$, and Bax were kindly provided by Dr. J. C. Reed. Antibodies against PARP was obtained from PharMingen (San Diego, Calif.), DFF-45 from Oncogene (Cambridge, Mass.), XIAP from Transduction Laboratories (Lexington, Ky.), caspase-3 from PharMingen, phospho-specific anti-pERK1/2 antibodies from Calbiochem (San Diego, Calif.). A specific antibody recognizing only the p20-processed caspase-3 band was provided by Idun Pharmaceutical, Inc. (La Jolla, Calif.).

Cell fractionation and Bax immunolocalization studies. The subcellular fractionation of cells was performed by a previously described method. Briefly, cells were swollen in ice-cold hypotonic Hepes buffer (10 mM Hepes at pH 7.4/5 mM MgCl$_2$/40 mM KCl/1 mM PMSF/10 µg/mL aprotinin/10 µg/mL leupeptin) for 30 minutes, aspirated repeatedly through a 25-gauge needle (25 strokes), and centrifuged at 200×g to pellet the nuclei. The resulting supernatant was then centrifuged at 10,000×g to pellet the heavy-membrane (HM) fraction containing the mitochondria. The HM supernatant was centrifuged at 150,000×g to pellet the plasma membranes, and the supernatant represented the cytosol (Cyt). Subcellular fractions were subjected to denaturing electrophoresis in a 12% acrylamide/0.1% SDS gel and transferred to nitrocellulose for Bax western blotting.

Northern blot analysis. The Bax probe was obtained by cloning the polymerase chain reaction (PCR) products of amplified cDNA. The sequence was compared with Genbank data to ensure that the correct cDNA was cloned. Twenty micrograms of total RNA was denatured and run overnight on a 1% formamide agarose gel at 30 volts. After staining in ethidium bromide, RNA was transferred to a Nitran filter and left overnight in 10× sodium chloride/sodium citrate (SSC), followed by drying at 80° C. Hybridization was carried out at 42° C. for 20 hours, and the filters were washed under highly stringent conditions. Signals were analyzed with a Betascope 603 (Betagen, Waltham, Mass.).

Metabolic labeling, immunoprecipitation, and immunoblot analysis. Cells were labeled with [$^{32}$P]orthophosphoric acid and then treated with 0.1 µM CDDO-Me or CDDO, after which Bcl-2 was analyzed by immunoprecipitation, as previously described Samples were electrophoresed in a 12% acrylamide/0.1% SDS gel, transferred to nitrocellulose, and exposed to Hyperfilm (Amersham Pharmacia Biotech, UK) at −80° C. The same blot was used for western blot analysis with anti-Bcl-2 antisera.

In vitro ERK assay. The effect of CDDO or CDDO-Me was determined using an in vitro MAPK kinase assay kit from Upstate Biotechnology (Lake Placid, N.Y.) and ERK1/2 antibody from Santa Cruz Biotechnology (Santa Cruz, Calif.). For each sample, ERK 1/2 was immunoprecipitated from $2 \times 10^7$ K562 or $1 \times 10^7$ HL60 cells using a specific anti-ERK 1/2 antibody and Protein A agarose (Life Technologies, Rockville, Md.). The ERK-containing agarose pellet was resuspended in Assay Buffer containing an inhibitor cocktail (PKC inhibitor peptide, PKA inhibitor peptide, and Compound R24571) to block possible contaminating non-ERK kinases. Where appropriate, varying concentrations (0.1, 1, and 10 µM) of CDDO or CDDO-Me was added. Dephosphorylated myelin basic protein (MBP; 25 µg) was used as substrate. Phosphorylation of MBP was observed by using an anti-phospho-MBP antibody. As a negative control, a lysate containing inactive ERK (obtained from K562 cells treated for 4 hrs in vivo with 10 µM of MEK inhibitor PD58059) was used in the assay. The amount of ERK2 immunoprecipitated from each sample was determined by using anti-ERK2 antibody.

For K562 cells, a control was performed to determine that CDDO or CDDO-Me could at least inhibit ERK upstream, if not directly. K562 cells were treated in vivo for 4 hrs with 1 µM CDDO-Me and lysate from these cells was used in the in vitro kinase assay.

Immunophenotyping. The PE-conjugated anti-CD11b, FITC-conjugated anti-CD14 monoclonal antibody (mAb) (Becton Dickinson) and PE-conjugated anti-CD95 mAb (PharMingen) were used at a 1/10 dilution. The percentage of positive cells was calculated by subtracting the percentage of cells with a fluorescence intensity greater than the set marker using the isotype control (background) from the percentage of cells with a fluorescence intensity greater than the same marker using the specific antibody.

Annexin V staining. Cells were washed in phosphate-buffered saline (PBS) and resuspended in 100 µl of binding buffer containing Annexin V (Roche Diagnostic Corporation, Indianapolis, Ind.). Cells were analyzed by flow cytometry after the addition of propidium iodide (PI). Annexin V binds to those cells that express phosphatidylserine on the outer layer of the cell membrane, and PI stains the cellular DNA of those cells with a compromised cell membrane. This allows for live cells (unstained with either fluorochrome) to be discriminated from apoptotic cells (stained only with annexin V) and necrotic cells (stained with both annexin and PI).

Cytofluorometric analysis of the $\Delta\Psi_m$. To evaluate the $\Delta\Psi_m$, cells were incubated with the cationic lipophilic dye chlorophenyl-X-rosamine (CMXRos; 150 nM; Molecular Probes, Inc., Eugene, Oreg.). CMXRos is incorporated into mitochondria driven by the $\Delta\Psi_m$ and reacts with thiol residues to form covalent thiol ester bonds. CMXRos fluorescence was recorded by flow cytometry in the FL3 channel. Background values of the apoptosis of control cells cultured without the CDDO-Me or in DMSO-solvent control (<10% CMXRos-low) were subtracted from the values obtained under the experimental conditions.

In a series of experiments, cells were pretreated for 1 hour with 50 µM CyA or 50 µM BA prior to the addition of CDDO-Me. These agents prevent a reduction in $\Delta\Psi_m$ induced by various agents that open mitochondrial permeability transition pores.

Detection of active caspases. The cell-permeable fluorogenic substrate Phi-Phi-Lux-G1D2 was administered to monitor caspase activity according to the manufacturer's recommendations (OncoImmunin, Inc, Kensington, Md.). Briefly, $10^6$ cells were resuspended in 5 µL of substrate solution and incubated for 1 hour at 37° C. in the dark. After incubation, cells were washed, and the fluorescence emission was determined using the FL-1 channel of a Becton Dickinson FACScan flow cytometer.

Statistics. Results are expressed as means±SEM. Levels of significance were evaluated by a two-tailed paired Student's t test, and P<0.05 was considered significant.

Example 2

Anticancer Properties of CDDO-compounds and Combination Therapies Thereof

Two CDDO-compounds, 2-Cyano-3,12-Dioxoolean-1,9-Dien-28-Oic Acid (CDDO) and its C-28 methyl ester, (CDDO-Me) induce differentiation, inhibit cell growth and induce apoptosis in leukemia cell lines and in primary samples from patients with AML.

Described herein are the mechanisms and efficacy of these CDDO-compounds activities in AML which allows the use of these CDDO-compounds as drugs for the treatment of hematological malignancies. Growth-inhibitory effects of CDDO and CDDO-Me on primary AML in clonogenic assay systems including the NOD/Scid model of AML are described. The contributions of the mitochondrial (Bcl-2-regulated) and death receptor (Fas/Fas-L) pathways for the induction of apoptosis by CDDO and CDDO-Me are described. A decrease in Bcl-2 expression is demonstrated.

The inventors also show that CDDO and CDDO-Me are novel ligands for PPARγ which is highly expressed in AML. Also demonstrated is a synergism between CDDO-compounds and retinoids. As PPARγ forms functional heterodimers with RXR, optimal combination of CDDO-compounds and retinoids for induction of apoptosis in AML are provided. Finally, pharmacokinetic, tissue distribution and toxicity studies of CDDO-compounds in mice for preclinical development of this combination therapy are described.

Figure 2:
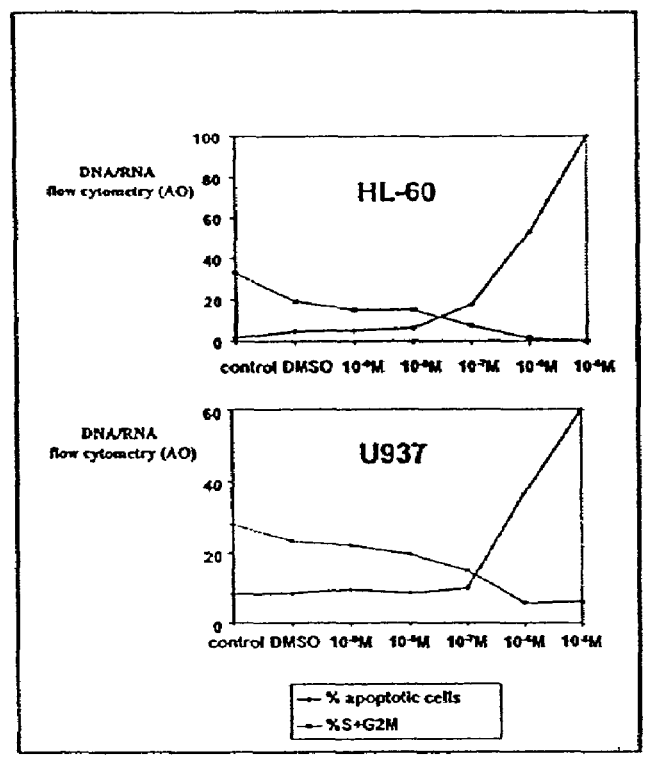
FIG. 2. CDDO inhibits proliferation and induces apoptosis.

CDDO-compounds Decrease Viability and Induce Apoptosis in Leukemic Cell Lines:

CDDO. The effect of CDDO on the survival of HL-60 and U937 leukemia cell lines is depicted in FIG. 1. A time-and dose-dependent decrease of HL-60 cells: at 48 hours, $10^{-8}$ M, at 72 and 96 hours, $10^{-9}$ M of CDDO reduced cell numbers by 50%. Viability of U937 cells was inhibited at $10^{-7}$ to $10^{-8}$ at 48 hours. DNA fragmentation was measured to confirm that the cell death induced by CDDO was due to apoptosis on a sub $G_1$ cell population by DNA/RNA flow cytometry (FIG. 2). The percentage of proliferating cells were analyzed by FCM. A significant decrease was noted at $10^{-7}$ M, as compared to DMSO at 48, 72 and 96 hours in HL-60 cells. In U937 cells, the proliferating (S+$G_2$M) fraction decreased at $10^{-7}$ M (14.9% compared with 23.3% in DMSO-controls) and at $10^{-6}$ M (5.6%) (FIG. 2).

As HL-60 cells do not have functional p53 (p53-'null') the cytotoxic effect of CDDO is p53-independent. Also, HL-60-Dox cells with high expression of the MDR-1 gene were sensitive to CDDO-induced killing, and blocking MDR-1 by the specific inhibitor PSC-833 did not affect CDDO cytotoxicity. Hence, MDR-1 does not seem to affect CDDO killing.

Figure 3:
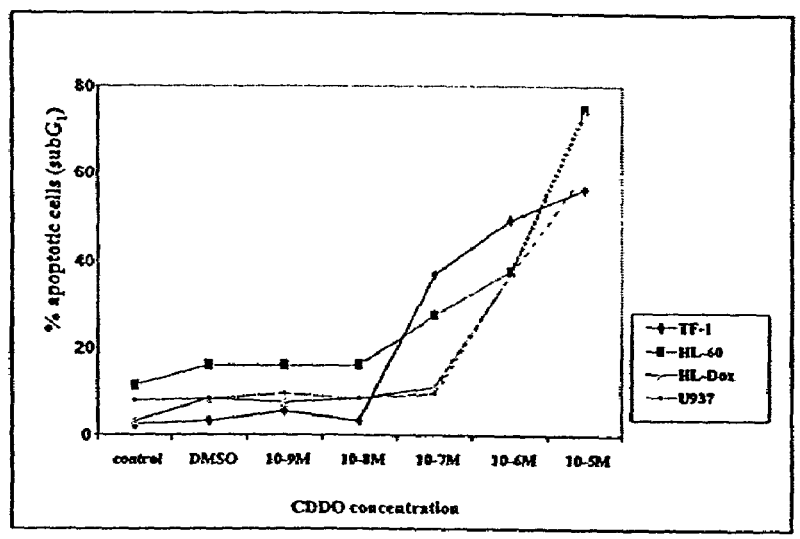
FIG. 3. CDDO induces apoptosis in myeloid cell lines.
Figure 4:
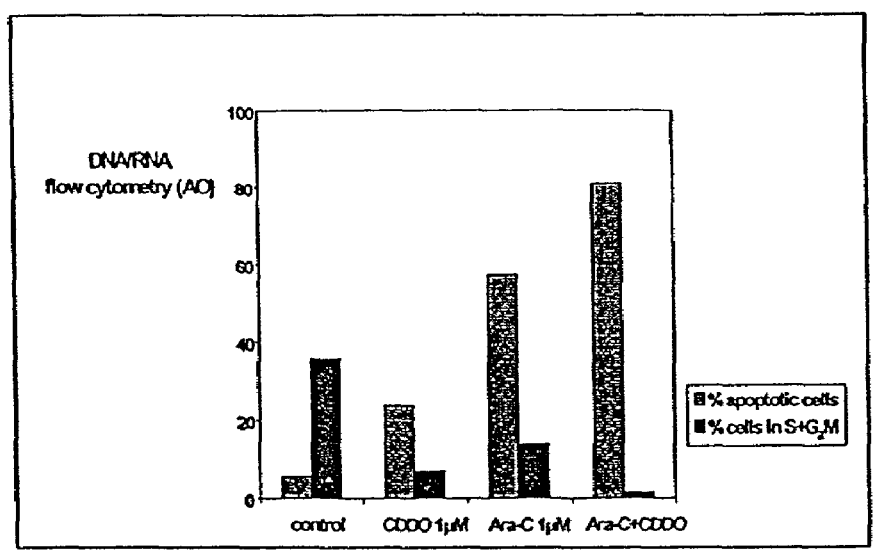
FIG. 4. CDDO enhances ara-C cytotoxicity in HL60-DOX cells.

The effect of CDDO on the viability of a variety of other leukemia cell lines is shown in FIG. 3. Exposure to $10^{-8}$ M to $10^{-5}$ M CDDO induced apoptosis in HL-60-Dox and TF-1 cells. CDDO treatment also enhanced ara-C-induced killing of leukemic cells as shown in HL-60-DOX cells (FIG. 4).

CDDO induces of differentiation in U937 leukemic cells (Suh et al., 1999). Thus, induction of monocytic differentiation in HL-60 cells was determined morphologically and by the induction of CD14 expression (see FIG. 16).

CDDO induced apoptosis without inducing differentiation in several leukemic cell lines and in primary AML, however CDDO induced apoptosis in HL-60 cells following induction of differentiation. Thus, CDDO can affect both apoptosis and differentiation in different cellular targets.

Figure 20:
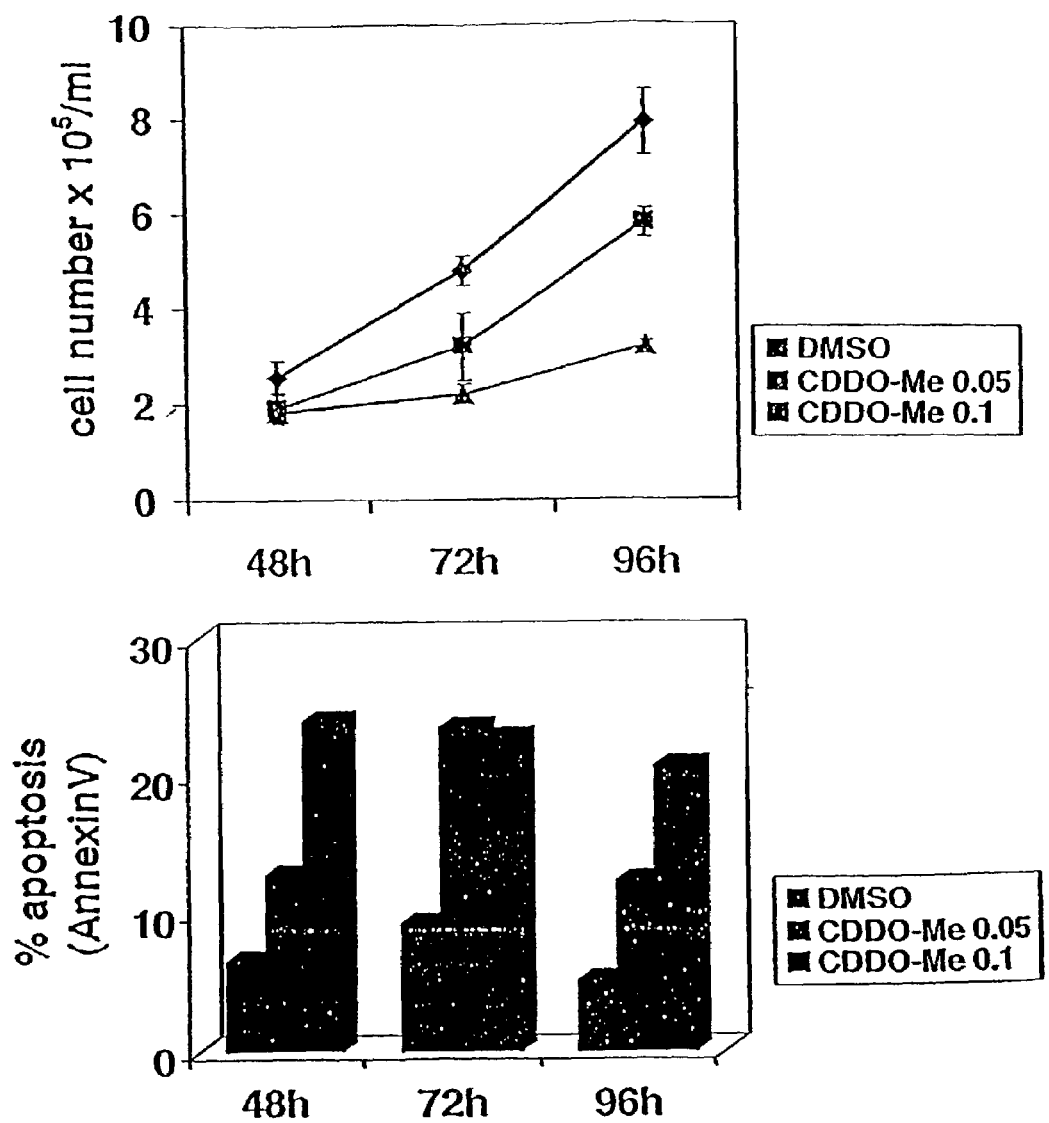
FIG. 20A.
FIG. 20B. CDDO-Me inhibits cell growth and induces apoptosis in HL-60 cells.

CDDO-Me. CDDO-Me is consistently more active than CDDO, with $IC_{50}$ of 0.4, 0.4 and 0.27 μM in the leukemic cell lines HL-60, KG-1 and NB4. Profound cytotoxic effect in Daudi lymphoid leukemic cells, were seen and 0.3 μM CDDO-Me decreased the cell number to 22.5% of DMSO-controls at 48 hrs. Mechanism of growth inhibition was analyzed on cell cycle and apoptosis in HL-60 cells. As demonstrated in FIG. 20A, CDDO-Me inhibited cell growth at 0.05 and 0.1 μM in a dose- and time-dependent fashion. At 0.5 μM essentially no viable cells were recovered at 48 hrs. Cell cycle measurements revealed no significant differences in cell cycle distribution. To study the effect of CDDO-Me on apoptosis, HL-60 cells were stained with FITC-labeled annexin V (Vermes et al., 1995). Cells were simultaneously stained with PI and analyzed by flow cytometry: a dose-dependent increase in annexin V binding in CDDO-Me-treated cells (FIG. 20B) were seen. Thus, induction of apoptosis is the primary mechanism of CDDO-Me-induced growth arrest. Again as with CDDO, the cytotoxic effect of CDDO-Me is p53-independent. Also, HL-60-Dox cells with high expression of the MDR-1 gene were sensitive to CDDO-Me-induced killing, and blocking MDR-1 by the specific inhibitor PSC-833 did not affect CDDO-Me cytotoxicity. Hence, CDDO-Me is p53 and MDR-1 independent.

CDDO-Me is a more potent inducer of granulo-monocytic differentiation in HL-60 cells as compared with CDDO: at 0.1 μM of CDDO-Me 86.6% of cells were CD11b+, while 1 μM of CDDO is needed to exert similar effect. In different leukemic cell lines and in primary AML, CDDO-Me induced apoptosis without marked differentiation, whereas in HL-60 cells apoptosis was observed primarily in differentiated cells. Thus, CDDO-Me affects both apoptosis and differentiation in different leukemic cell populations.

Figure 5:
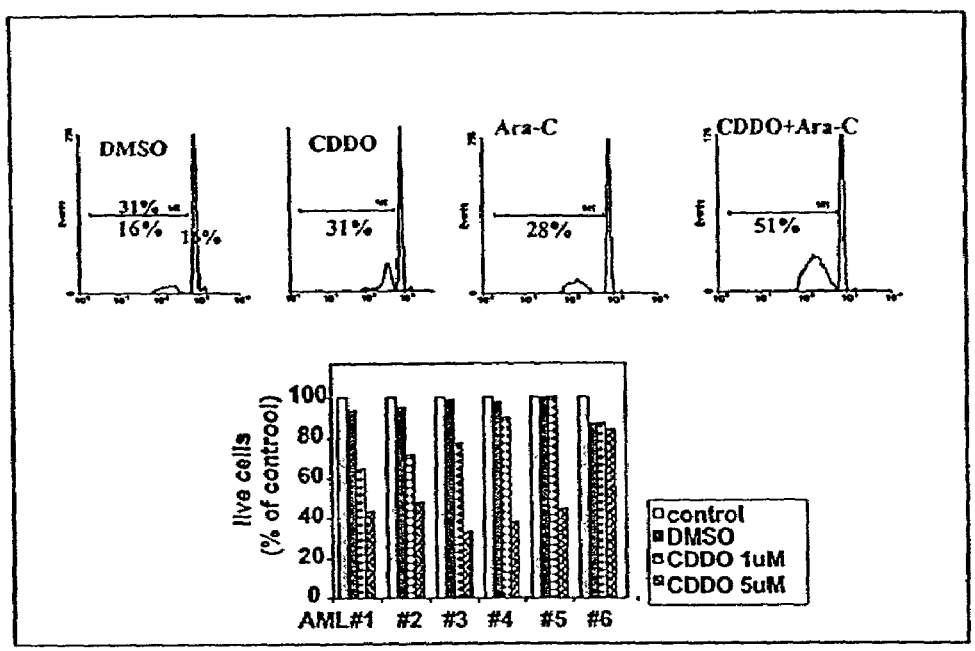
FIG. 5. CDDO alone and in combination with ara-C induces apoptosis in primary AML cells.
Figure 6:
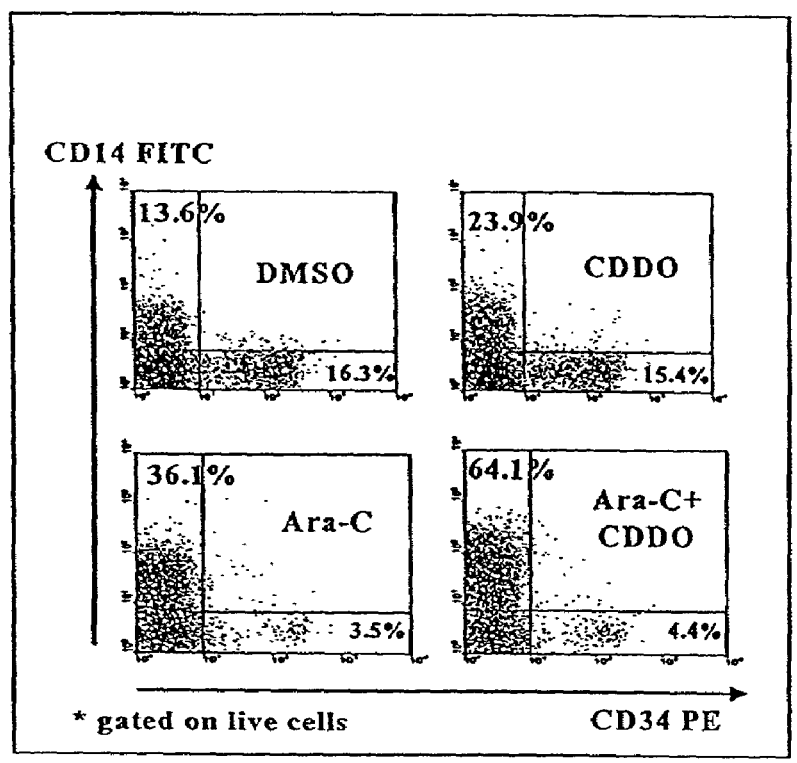
FIG. 6. CDDO combined with ara-C induces differentiation in primary AML cells.

CDDO-compounds Decrease Viability and Induce Apoptosis in Primary AML Cells in Suspension Cultures and in Clonogenic Assays:

CDDO. In primary AML, CDDO and CDDO-Me induced apoptotic cell death in a dose-dependent fashion as determined by sub$G_1$ flow cytometry. 1 μM CDDO induced apoptosis in 3 of 6 AML samples in vitro, and 5 μM induced apoptosis in 5 of 6 samples (FIG. 5). CDDO increased ara-C-induced apoptosis in AML samples (DMSO control, 27.7±3.7%; CDDO 1 μM, 41.2±4.4%; ara-C 1 μM 41.6±4.6%; CDDO+ara-C, 53±4.6%, n=23). The paired mean difference±SEM was 13.5%±2.8%. Monocytic differentiation was induced in 3/11 AML, as evidenced by down-regulation of CD34 expression and induction of the monocytic differentiation marker CD14. This effect was more pronounced in ara-C/CDDO combinations (FIG. 6).

Figure 7:
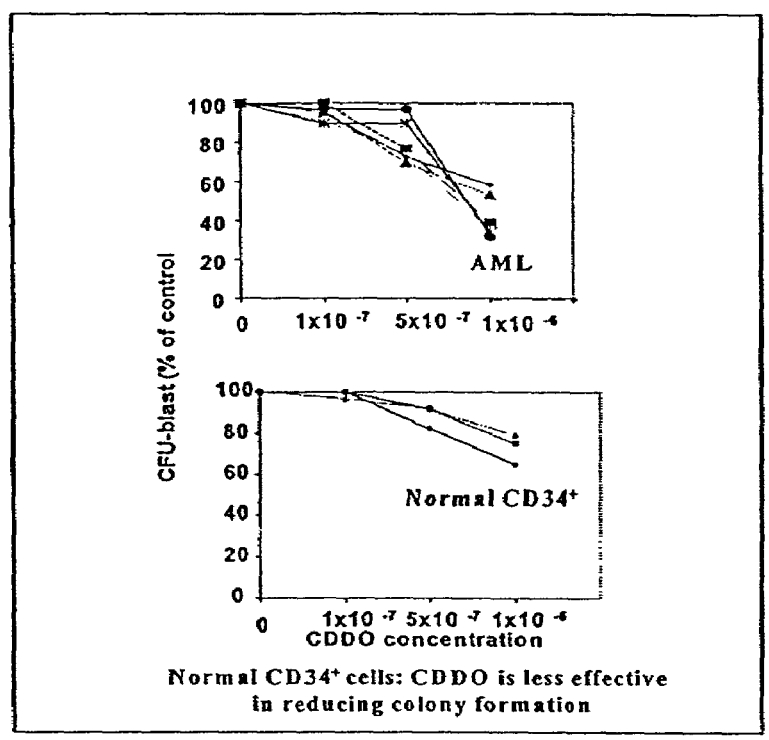
FIG. 7. CDDO decreases colony formation of AML blasts.

The effect of CDDO on clonogenic AML cells were tested. Colony formation of AML progenitors (n=6) was significantly reduced at 1 μM CDDO (58±4.6%). 0.5 μM CDDO resulted in inhibition of >50% colonies in one CML-BC sample tested. MACS-separated normal CD34+ cells were used as controls, CFU-GM of normal CD34+ cells were inhibited only by 26.8±4.3% at this concentration (n=3) [p=0.004] (FIG. 7).

Thus, CDDO decreases viability and induces apoptosis in myeloid leukemic cell lines and primary AML samples. CDDO also induces differentiation in HL-60 cells and in primary AML. CDDO also reduces colony formation of AML progenitors, but did not inhibit normal CFU-GM cells.

Figure 21:
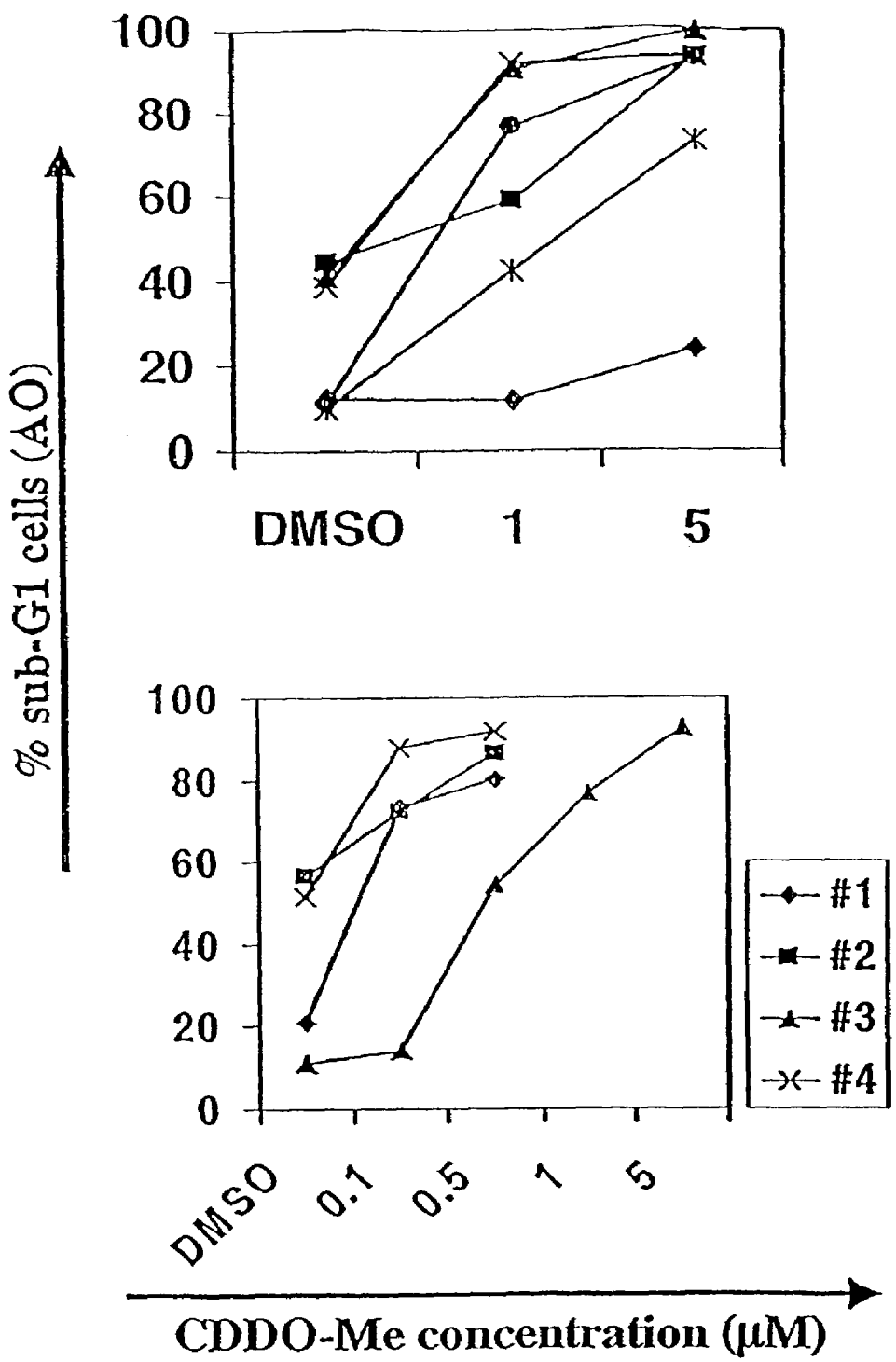
FIG. 21A.
FIG. 21B. CDDO-Me induces apoptosis in primary AML samples.
Figure 22:
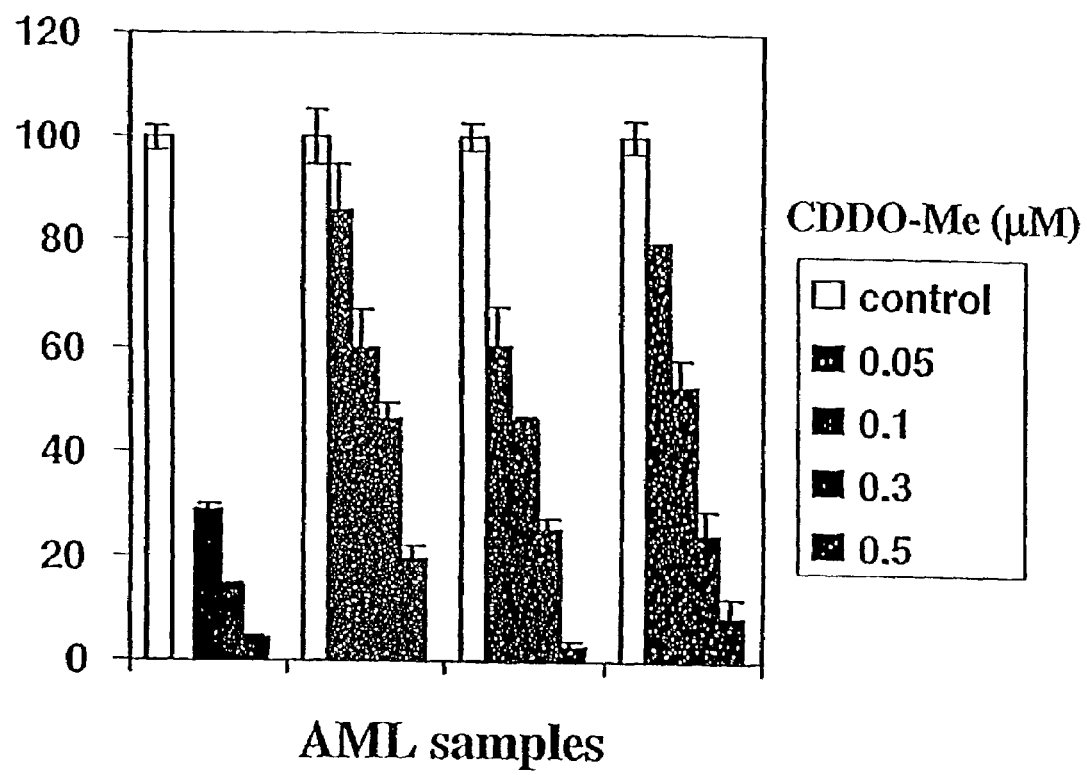
FIG. 22. CDDO-Me inhibits AML clonogenic progenitor growth.

CDDO-Me. In primary AML, CDDO-Me induced apoptotic cell death in a dose-dependent fashion as determined by DNA flow cytometry (subG$_1$): at 1 µM CDDO-Me, apoptosis was induced in 5 of 6 AML samples in vitro, and 5 µM induced apoptosis in 6 of 6 samples. More than 90% apoptotic cells were detected in 4/6 samples following exposure to 5 µM of CDDO-Me (FIG. 21A). At lower concentrations, CDDO-Me induced a dose-dependent increase in the percentage of the apoptotic cells in 4/4 samples tested (FIG. 21B). The paired mean difference between the CDDO-Me 0.1 µM and DMSO control is 26.9%±10.8% (CDDO-Me-DMSO, mean±SEM), and the paired mean difference between the CDDO-Me 0.5 µM and DMSO is 43.2%±5.2%. CDDO-Me also enhanced ara-C-induced cell killing (DMSO control, 24.9±7.4% CDDO-Me 1 µM, 50.5±15%; ara-C 1 µM 39.8±8.2%; CDDO-Me±ara-C, 65.4±10.2%, n=6). Monocytic differentiation was induced in 2/5 AML, as demonstrated by induction of the monocytic differentiation marker CD14. CDDO-Me also induced apoptosis in CML-blast crisis samples in vitro (in 3 of 4 samples at 1 µM, in 4 of 4 at 5 µM), enhanced ara-C-induced cell death and induced differentiation in 1 of 4 samples tested. Effects of CDDO-Me were also tested on clonogenic AML cells. Colony formation of AML progenitors was significantly inhibited in a dose-dependent fashion, with 46.7%±6.6% surviving colonies at 0.1 µM of CDDO-Me, 27.5%±6.8% for the CDDO-Me 0.3 µM, and 8.8%±3.8% for the CDDO-Me 0.5 µM (FIG. 22). 0.1 µM CDDO-Me also inhibited>50% colonies in one CML-BC sample tested. In contrast, 79±5.6% and 63.4±1.1% CFU-GM generated from normal CD34* cells were detected after 0.1 and 0.5 µM of CDDO-Me treatment (n=3).

Thus, CDDO-Me decreases viability and induces apoptosis in myeloid leukemic cell lines and in primary AML samples. CDDO-Me also induces differentiation in HL-60 cells and in primary AML. CDDO-Me also significantly reduced colony formation of AML progenitors.

CDDO-compounds Induce Changes in the Apoptotic Machinery:

The molecular mechanisms underlying CDDO-compound induced cell death were observed by staining HL-60-Dox cells with annexin V, which binds phosphatidylserine with high affinity. Translocation of phosphatidylserine to the cell surface is considered one of the earliest events in apoptosis and can be analyzed by staining with FITC-labeled annexin V (Vermes et al., 1995). Cells were simultaneously stained with PI and analyzed by flow cytometry.

Figure 8:
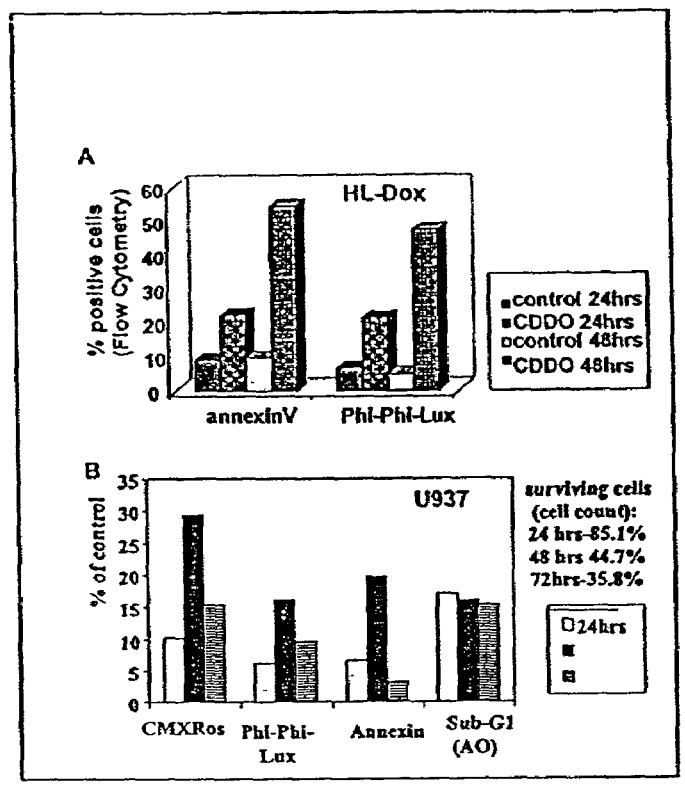
FIG. 8. CDDO induces decreases in mitochondrial potential (CMXRos). Annexin V-positivity and Caspase Cleavage.

CDDO. A time-dependent increase in annexin V binding in CDDO treated cells at 24 and 48 hours was observed (FIG. 8A). To test the effect of CDDO on the cleavage of caspase-3 the fluorogenic substrate of caspase-3 Phi-Phi-Lux (PI) was used. Cells were simultaneously stained with PI and analyzed by flow cytometry. As shown in FIG. 8A, CDDO-compounds induced Phi-Phi-Lux-positivity that paralleled changes in the plasma membrane. Similar results were obtained in U937 cells, where increases in annexin-V and Phi-Phi-Lux positivity were seen 48 hrs after treatment with 1 µM CDDO. Early (24 hrs) changes in mitochondrial membrane potential preceded caspase activation and peaked at 48 hrs (FIG. 8B).

To study the molecular mechanisms underlying CDDO-induced cell death, time-dependent apoptotic changes in D9 leukemic cells were analyzed. Translocation of phosphatidylserine to the cell surface is considered an early event in apoptosis and can be analyzed by staining with FITC-labeled annexin V. A time-dependent increase in annexin V binding in CDDO-treated cells at 5 and 24 hours was observed. To test the effect of CDDO on the cleavage of caspase-3, the fluorogenic inhibitor that binds to activated caspase-3 (Caspatag, Intergen), was utilized. CDDO induced Caspatag positivity that paralleled changes in the plasma membrane. Relatively early (3 and 5 hrs) changes in mitochondrial membrane potential were observed (measured by CMXRos). These data demonstrate that CDDO induces apoptotic cell death through the mitochondrial pathway.

The effect of CDDO on the processing of different caspases was also analyzed. In AML-2 cells, CDDO induced a dose-response decrease in pro-caspase-3, with appearance of cleaved caspase-3 product at 1 µM of CDDO at 24 hrs. CDDO (2, 5 and 10 µM) also induced decrease in unprocessed caspase-8 and -9. This activation of caspases correlated with a marked decrease in cell viability.

To characterize the correlation between PPARγ and caspase activation, caspase-3 levels in D9 cells transfected with wt-PPARγ were analyzed. Six different single cell-derived clones were treated with 3 µM CDDO or vehicle controls for 5 hrs. Caspase-3 cleavage was analyzed by Western blot. A decrease in pro-caspase-3 with appearance of the cleaved product was readily observed in all clones. The degree of cleavage was higher in PPARγ-transfected than in vector control cells that express endogenous PPARγ. Analysis of DNA fragmentation revealed endonucleolytic DNA cleavage in CDDO-treated cells that was predominantly seen in PPARγ-transfected cells. These changes correlated with plasma membrane changes: vector control=47.0% annexin V-positive cells; wt-PPARγ-transfected cells=73.3±1.1% annexin V (+), n=6. Cell number did not change in vector control cells, while it decreased by 48.8±12.4% in CDDO-treated PPARγ-transfectants. PPARγ-transfected cells were also more sensitive to PPARγ-ligand 15d-PGJ2 (41.0% vs 16.0% annexin (+) cells at 3 µM). These results demonstrate that caspase activation by CDDO depends on the expression levels of PPARγ.

In addition, a time-dependent increase in annexin V binding in CDDO treated cells at 24 and 48 hours was observed (FIG. 8A). To test the effect of CDDO on the cleavage of caspase-3 the fluorogenic substrate of caspase-3 Phi-Phi-Lux (PI) was used. Cells were simultaneously stained with PI and analyzed by flow cytometry. As shown in FIG. 8A, CDDO-compounds induced Phi-Phi-Lux-positivity that paralleled changes in the plasma membrane. Similar results were obtained in U937 cells, where increases in annexin-V and Phi-Phi-Lux positivity were seen 48 hrs after treatment with 1 µM CDDO. Early (24 hrs) changes in mitochondrial membrane potential preceded caspase activation and peaked at 48 hrs (FIG. 8B).

Mechanisms of CDDO-induced apoptosis in leukemia cell lines and in primary AML samples were also determined. The involvement of the death receptor/Fas pathway was studied in NB4 cells. Treatment with 0.5 µM CDDO induced cell surface Fas/CD95 expression at 48 hours (MFI 34.8 vs 24.8 in DMSO-treated cells and 26 in untreated control). At this concentration, 22.3% of cells were annexin V positive compared with 11.4% in DMSO-controls. At 1 µM, 56.3% of cells were apoptotic. Similarly, 1 µM CDDO induced Fas expression in 7/12 AML CD34+ cells (MFI, 22.3±3.5 in DMSO-controls, 40±4.3 in CDDO-treated CD34+ cells, p<0.01). However, CDDO did not induce Fas expression in p53-negative HL-60 and HL-60-Dox cells (Owen-Schaub et al., 1994), suggesting involvement of the different mechanisms of the apoptotic cell death in these cells.

The involvement of the mitochondrial apoptotic pathway in CDDO mediated apoptosis was analyzed in U937 cells. A >40% decrease in Bcl-2 protein was observed at 72 hrs of 1

μM of CDDO treatment as determined by quantitative flow cytometry. Decreased Bcl-2 expression was also demonstrated by Western blot analysis in CDDO-treated HL-60, KG-1 and NB4 cells. CDDO also significantly decreased Bcl-2 expression level in CD34+ cells in 9 of 18 primary AML samples tested (p=0.01).

Figure 9:
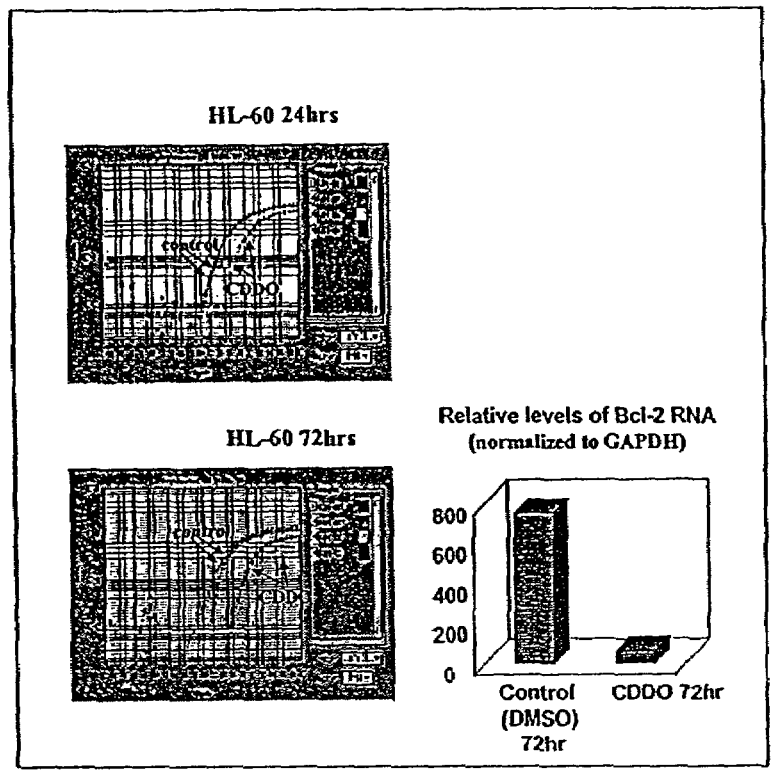
FIG. 9. CDDO decreases Bcl-2 m-RNA in HL-60 cells.

The effect of CDDO on the Bcl-2 mRNA expression was analyzed utilizing quantitative TaqMan PCR. In HL-60 cells, Bcl-2 mRNA decreased at 24 hrs and decreased further (>than 10-fold) at 72 hours; in NB4 cells, a small decrease of Bcl-2 mRNA (2-fold) was observed only at 72 hrs (FIG. 9). These results were confirmed in two independent experiments.

Figure 10:
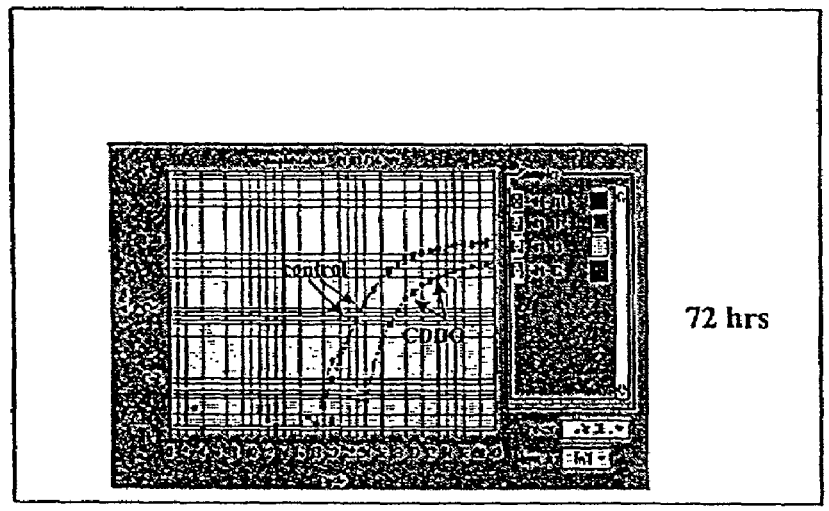
FIG. 10. CDDO decreases XIAP m-RNA in HL-60 cells.

The expression of the other anti-and pro-apoptotic proteins following CDDO exposure were also analyzed. No differences were observed in the expression of the pro-apoptotic proteins Bax and Bcl-$X_s$. However, the protein levels of the inhibitor-of-apoptotic protein XIAP decreased in KG-1 and NB-4 cells. A decrease in XIAP mRNA levels at 48 and 72 hrs was also demonstrated (FIG. 10).

The inventors also tested if overexpression of the anti-apoptotic protein Bcl-2 protected leukemic cells from CDDO-induced cytotoxicity. For these experiments U937 cells transduced with Bcl-2 were used with empty-vector containing counterparts as controls. Bcl-2 overexpression (3-fold) did not protect cells from CDDO-killing.

The differential expression of a large number of genes involved in apoptosis, proliferation and signal transduction were analyzed utilizing the Atlas Cancer c-DNA array from Clontech (Palo Alto, Calif.). Leukemic U937 cells were treated with CDDO for 24 hrs (1 μM) to study changes in gene expression levels prior to the induction of differentiation and/or apoptosis. The downregulation of 17 genes (over two-fold) was seen, some of these genes were MAPKK5, STAT5A and B, DNA topoisomerase 2, VEGFR1 and VEGF. 7 genes were upregulated including JNK2 and death receptor DR5, a receptor for TRAIL.

Thus, it is demonstrated that CDDO downregulates anti-apoptotic Bcl-2 and XIAP mRNA and protein expression level and induces Fas expression in leukemic cell lines and in the majority of primary AML samples. The cDNA array data provides a means for the identification of genes contributing to the anti-leukemic effects of CDDO.

Figure 33:
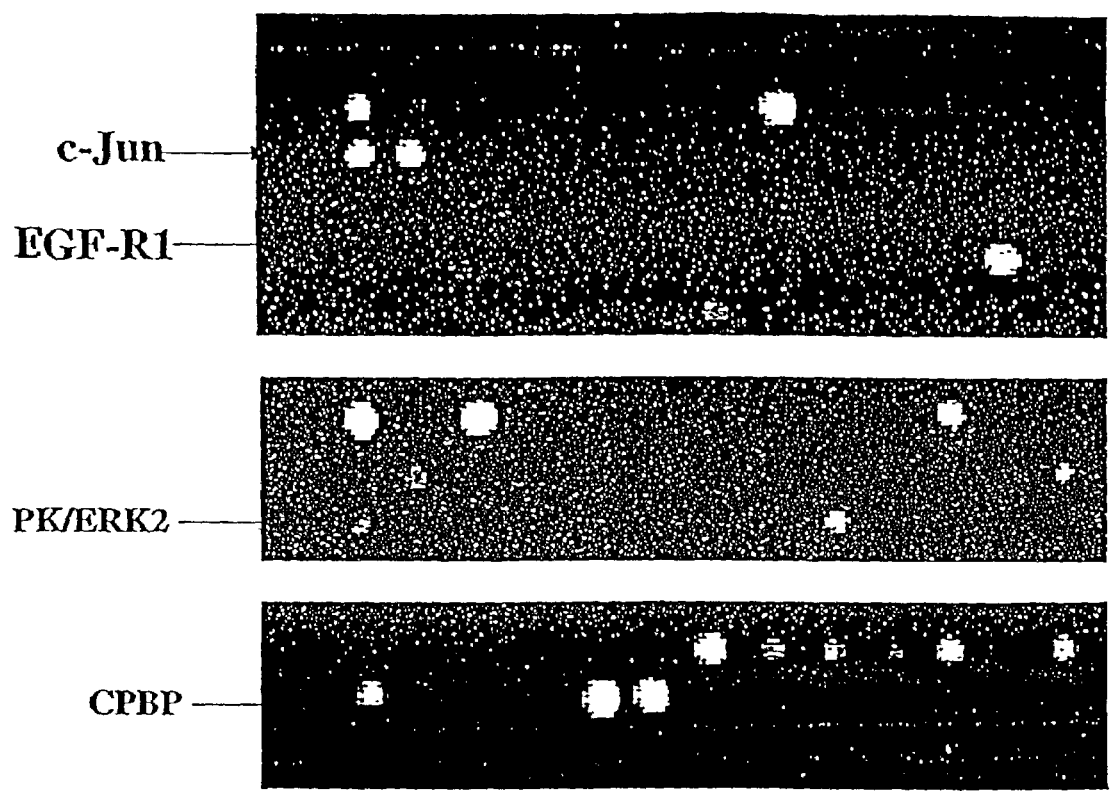
FIG. 33. cDNA array: CDDO-Me decreases VEGFR1 expression in U937 cells.

Differential expression of a large number of genes involved in apoptosis, proliferation and signal transduction was also performed for CDDO-Me. Leukemic U937 cells were treated with 1 μM of CDDO-Me for 1 hour with the aim of inducing changes in gene expression levels prior to the induction of differentiation or apoptosis. In preliminary studies, the inventors observed over two-fold downregulation of 23 genes: these include MAPK/ERK2, endothelin2, MLH1. Remarkably, decreased expression of VEGFR1, that potentially mediate pro-angiogenic properties of the leukemic cells, was observed (FIG. 33). Twenty-two genes were upregulated including c-jun, TNF-R1 and CPBP, zinc finger protein involved in transcriptional control. The cDNA array data require conformation but may indicate what changes in gene expression contribute to the observed anti-leukemic effects of CDDO-Me.

Figure 11:
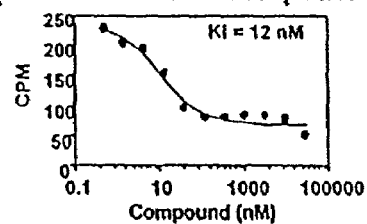
FIG. 11A. & FIG. 11B.
FIG. 11B. CDDO transactivates PPARγ.
Figure 11:
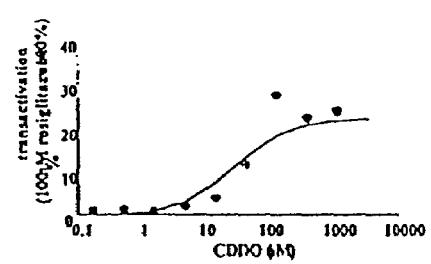

PPARγ, a member of a family of nuclear receptors, induces differentiation and growth arrest in preadipocyte cells and can mediate inflammatory processes. The PPARγ ligands 15d-PGJ2 at 3 μM and BRL49653 at 5 μM induce monocytic differentiation of HL-60 cells but exerted no killing at this concentration (Tontonoz et al., 1998). The ability of CDDO-compounds to directly interact with PPARγ was assessed by a scintillation proximity assay (SPA) (Nichols et al., 1998) using $^3$H-rosiglitazone as the ligand and bacterially expressed PPARγ LBD. As shown in FIG. 11A, non-radioactive CDDO competed efficiently with [$^3$H]-rosiglitazone for binding to the PPARγ LBD ($K_i$=12 nM) (Wang et al., 2000). In a similar assay, rosiglitazone was shown to compete for bound $^3$H-CDDO, with $K_i$ values of 50 nM.

To determine if bound CDDO transactivates PPARγ, a Gal4-PPARγ chimeric protein was used to drive the expression of luciferase linked to the DNA binding sequence of GAL4 (FIG. 11B) (Wang et al., 2000). CDDO transactivates GAL4-PPARγ in a dose-dependent manner. In contrast, CDDO did not transactivate the PPARα receptor. These data demonstrate that CDDO can interact directly and specifically with PPARγ LBD at sub-micromolar concentrations and thus establishes CDDO as a novel PPARγ ligand. All known pharmacological PPARγ ligands had anti-proliferative and differentiating effects only when used at higher (3 or 5 μM) concentrations.

Figure 12:
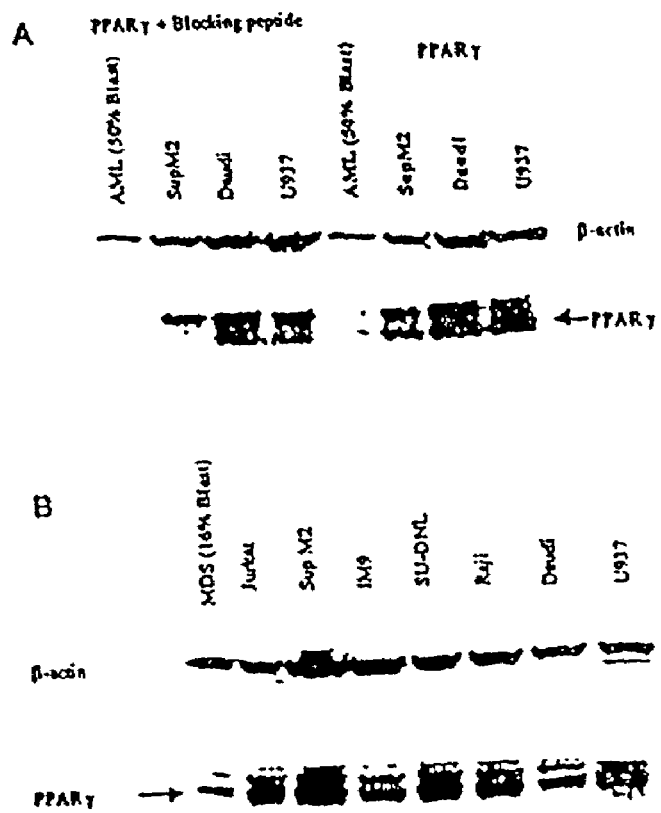
FIG. 12A. & FIG. 12B. PPARγ protein expression (western blot).
Figure 13:
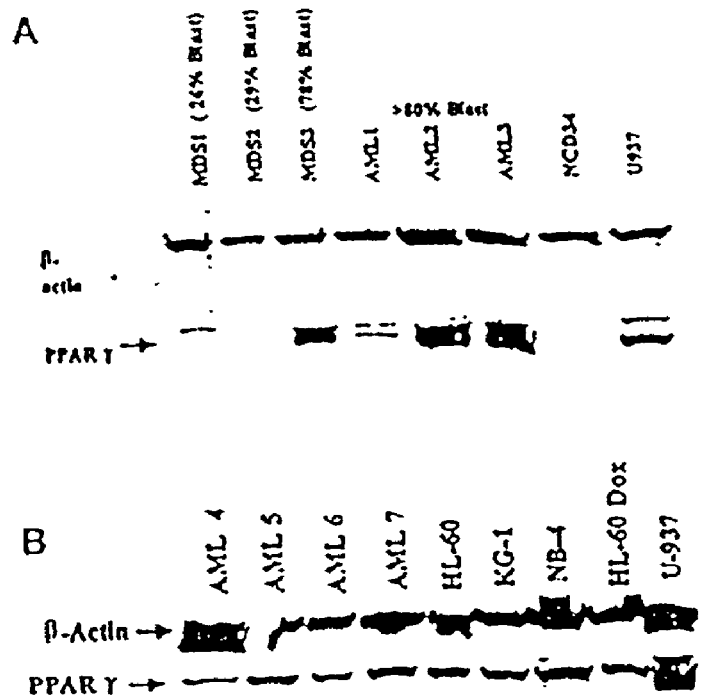
FIG. 13A. & FIG. 13B. PPARγ is expressed in myeloid cell lines and primary AML samples.

Western Blot Analysis. The expression of PPARγ in leukemic cell lines and primary AML/MDS samples was analyzed by western blot. The specificity was confirmed using a monoclonal antibody to PPARγ (Santa Cruz Biotechnology, Inc.) or an antibody pre-adsorbed with a blocking peptide for competition studies. The monoclonal antibody reacted with both, PPARγ1 and PPARγ2 isoforms. Disappearance of the specific band after pre-adsorbtion with blocking peptide confirmed the correct position of the PPARγ band (FIG. 12A). The PPARγ protein was expressed in 6 myeloid and 6 lymphoid cell lines tested (FIG. 12B, FIG. 13B). PPARγ was also detected in 9/11 primary AML samples with high (>50%) blast count, low expression was noted in 2 of 4 samples from patients with advanced MDS (RAEB) (FIG. 13). PPARγ was not expressed in 2 samples of normal magnetic-separated CD34$^+$ cells (FIG. 13). Thus, PPARγ is highly expressed in leukemic blasts.

Sensitivity to CDDO-induced apoptosis correlated with levels of PPARγ: in U937 cells expressing 3-fold higher PPARγ levels than HL-60 cells, 1 μM CDDO induced 69.4% apoptotic sub-$G_1$ cells at 48 hrs compared with 34.8% in HL-60. In contrast, 73.6% Daudi cells which have lowest detectable PPARγ expression were alive at this concentration of CDDO. However, at higher (2 μM) CDDO concentrations both cell lines were killed equally (30.2 and 25.3% viable cells) perhaps as the result of maximal receptor stimulation.

To test if the cytotoxic effect of CDDO is mediated by PPARγ receptor, growth of Daudi cells (which have lowest detectable PPARγ expression) following CDDO treatment was examined. In U937 cells only 44.7% of the cells remained viable after 48 hrs of CDDO (1 μM) treatment. In contrast, 73.6% Daudi cells were alive at this concentration of CDDO. However, at higher (2 μM) CDDO concentrations both cell lines were killed equally (30.2 and 25.3% viable cells) perhaps as the result of maximal receptor stimulation.

To characterize the correlation between PPARγ and caspase activation, caspase-3 levels in D9 cells transfected with wt-PPARγ were analyzed. Six different single cell-derived clones were treated with 3 μM CDDO or vehicle controls for 5 hrs. Caspase-3 cleavage was analyzed by Western blot. A decrease in pro-caspase-3 with appearance of the cleaved product was readily observed in all clones. The degree of cleavage was higher in PPARγ-transfected than in vector control cells that express endogenous PPARγ. Analysis of DNA fragmentation revealed endonucleolytic DNA cleavage in CDDO-treated cells that was predominantly seen in PPARγ-transfected cells. These changes correlated with plasma membrane changes: vector control=47.0% annexin V-positive cells; wt-PPARγ-transfected cells=73.3±1.1% annexin V (+), n=6. Cell number did not change in vector control cells, while it decreased by 48.8±12.4% in CDDO-treated PPARγ-transfectants. PPARγ-transfected cells were also more sensitive to PPARγ-ligand 15d-PGJ2 (41.0% vs 16.0% annexin (+) cells at 3 μM). These results demonstrate that caspase activation by CDDO depends on the expression levels of PPARγ.

It has recently been demonstrated that PPARγ ligands recruit the DRIP205 co-activator to PPARγ (Yang et al., 2000). DRIP205 is a key subunit of the DRIP multisubunit coactivator complex that anchores the other 14 subunits to the nuclear receptor LBD. DRIP205 was identified from U937 leukemic cells (Rachez et al., 2000). DRIP205 expression was found to be low in parental D9 and in vector-transfected cells, while it was higher in selected sub-clones transfected with wt-PPARγ and was further induced by PPARγ ligand 15d-PGJ2.

To test the efficacy of CDDO compared to other PPARγ ligands, the effect of PPARγ ligands such as 15d-PGJ2 (Cayman Chemical Company), BRL49653 (Smith Kline Beecham), L-805645 (Merck), GW347845X (Glaxo Welcome) were compared to that of CDDO: 5 μM of 15d-PGJ2 was required for 50% inhibition of HL-60 cells; other ligands including roziglitazone (BRL49653) exerted similar effects only at high (25-50 μM) concentrations. This decrease in cell viability was mediated by induction of apoptosis, as determined by annexin V staining. Of importance, RXR-specific ligand LG100268 enhanced growth-inhibitory effects of PPARγ ligands.

In HL-60 cells, all PPARγ ligands induced CD11b expression in a dose-dependent fashion, but significantly higher concentrations were required to achieve effects similar to CDDO (Table 4):

ligand and DNA binding, but exhibits reduced transactivation due to impaired coactivator (CBP and SRC-1) recruitment.

wt-hPPARγ and the DN-PPARγ mutant constructs were sequenced prior to transfection to verify the correct sequence. Plasmid DNA was purified using the QIAprep spin miniprep kit (Qiagen). Stable transfection of the leukemic cells was performed using the calcium-phosphate method. Cells were split the day before transfection. On the day of transfection, $7.5×10^6$ cells were harvested by centrifugation and seeded in 5 ml of growth medium supplemented with serum and antibiotics. 0.5 ml of calcium-phosphate-DNA (5 μg) precipitate mixture was added to cells and incubated overnight. The next day medium containing complexes was removed, cells were washed in PBS and resuspended in 5 ml of fresh medium. G418 was added at 48 hrs post-transfection; G418 concentrations were selected for each cell line based on the preliminary dose-response curve. After 4 days cells were passaged at 1:5 into the G418-containing selective medium. Medium was replaced on day 3-4, and cells were plated at 100 μl/well in a 96-well plate. The cultures were re-fed every 3-4 days with addition of fresh medium containing G418. When cultures reached 50% confluence, cells growing in the individual wells (clones) were collected, transferred into a 24-well plate and screened for the expression of the transgene utilizing 2 methods: 1) Dot-blot analysis of protein by direct deposition of the sample (protein lysate) on the membrane followed by western blot with anti-PPARγ antibody. 2) Western blot analysis of the clones selected by dot-blot analysis, using anti-PPARγ and anti-FLAG antibodies.

Twenty clones were tested for pcDNA3, wt- and DN transfectants; the 2 best clones were selected for further cloning. To obtain single-cell clones, cells were diluted to 0.8 cells/well (i.e., plating 100 μl/well of 8 cells/ml dilution) and plated

TABLE 4

Expression of CD11b in HL-60 cells treated with PPARγ ligands for 7 days:

| Control (DMSO) | CDDO | | 15d-PGJ2 | | GW347845X | | L-805645 | | BRL49653 | |
|---|---|---|---|---|---|---|---|---|---|---|
| | μM | CD11b % | M | CD11b % | μM | CD11b % | μM | CD11b % | μM | CD11b % |
| 24.9 | 0.1 | 45.0 | 1 | 34.1 | 10 | 28.3 | 10 | 38.6 | 10 | 38.9 |
| | 0.3 | 75.9 | 3 | 49.4 | 25 | 44.8 | 25 | 42.9 | 25 | 48.5 |
| | 0.5 | 83.1 | 5 | 83.9 | | | | | | |
| | | | 10 | 88.9 | | | | | | |

In primary AML samples, exposure to PPARγ ligands 15d-PGJ2 (5 μM), BRL49653 (25 μM), L-805645 (25 μM), GW347845X (25 μM) induced 27.7%, 7%, 21% and 27.8% annexin-V-positive cells, respectively at 72 hrs; this effect was enhanced by combination with the RXR-specific ligand LG-10268. These data demonstrate the ability of PPARγ ligands to induce apoptosis and differentiation and also provide evidence that CDDO has higher activity in leukemic cells than all other PPARγ ligands.

Genetic Analysis. To further characterize the correlation between hPPARγ and antileukemic activity, HL-60, CDM-1, U937, KG-1 and KBM-3 cells were transfected with an empty expression vector (pcDNA3), FLAG-tagged wt-PPARγ or FLAG-tagged L466A/E469A dominant-negative (DN) PPARγ mutant together with a selectable marker (neo). In the DN-PPARγ mutant highly conserved hydrophobic and charged residues ($Leu^{466}$ and $Glu^{469}$) in helix 12 of the ligand-binding domain were mutated to alanine. It retains in a 96-well plate; this dilution provides 36% of wells with 1 cell/well by Poisson statistics. As controls, 10 wells were plated with 100 μl/well of 80 cells/ml dilution (i.e., 8 cells/well).

After sub-cloning the analysis of protein expression was repeated for the selected subclones (dot-blot followed by Western blot analysis), and the presence of transgene was confirmed by RT-PCR for neomycin (neomycin ORF: bases 2151-2945 in pcDNA3). Oligonucleotide primers (F, forward; R, reverse) used were as follows: F 5'-CAAGATGGAT-TGCACGCAGG-3' and R 5'-GAGCAAGGTGAGATGA-CAGG-3'. Amplified products (325 bp) were separated by gel electrophoresis.

HL-60, CDM-1, KG-1, KBM-3 and D9 cells were transfected with wt-, DN-PPARγ and vector control (pcDNA3). CDM-1 and KG-1 cells do not express endogenous PPARγ, while HL-60, D9 and KBM-3 express variable levels of the protein. For HL-60 cells, 120/176 wells were positive for wt-PPARγ, 141/178 for DN-PPARγ and 202/384 for pcDNA;

for CDM-1 cells, 130/171 wells were positive for wt-PPARγ, 132/178 for DN-PPARγ and 123/180 for pcDNA. 20 clones each (wt-, DN-PPARγ and pcDNA) were tested by dot-blot and verified by Western blot analysis. Two selected clones/ each were further subcloned; analysis of subclones is currently in progress using dot-blot, Western blot and RT-PCR.

The sensitivity of leukemic cells that overexpress PPARγ to CDDO-induced killing was tested. Vector control (pcDNA) or wt-PPARγ-transfected D9 cells (2 different clones) were treated 0.2 µM of CDDO for 48 hrs. Cell viability was assessed by cell count after Trypan blue exclusion, and apoptosis determined by PS/annexin V/Propidium Iodide (PI) flow cytometry. Leukemic cells transfected with PPARγ expressed 2.8-3.7-fold higher amounts of protein compared with vector controls. As expected, forced expression of PPARγ significantly enhanced the sensitivity of leukemic cells to CDDO killing. High expression of PPARγ in transfected cells was confirmed by immunohistochemistry analysis demonstrating high levels of nuclear PPARγ in both transfected clones. Importantly, CDDO increased PPARγ expression in both, vector control and transfected cells. This experiment provides additional evidence for CDDO being an effective PPARγ ligand and also provides an explanation for activity of the compound in cells with low baseline PPARγ levels. No significant differences in Bcl-2 and Bax expression were noted in PPARγ- or vector-transfected cells. These data also indicate that PPARγ expression determines the sensitivity of leukemic cells to CDDO-induced apoptosis. Of note, similar results (>50% higher sensitivity compared to vector-control cells) were observed in all six single cell-derived subclones tested.

Figure 23:
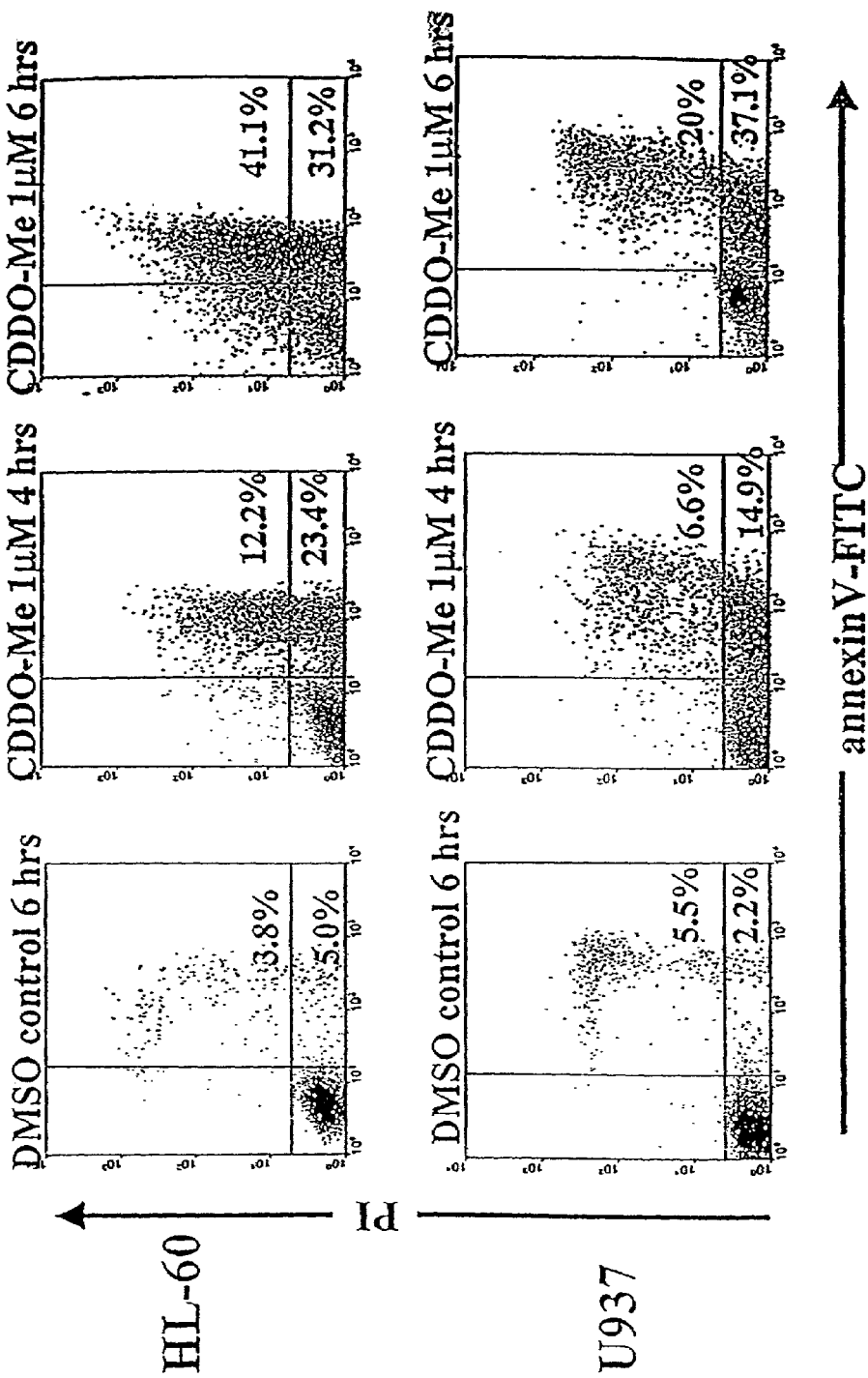
FIG. 23. CDDO-Me induces Annexin V positivity in leukemic cells.
Figure 24:
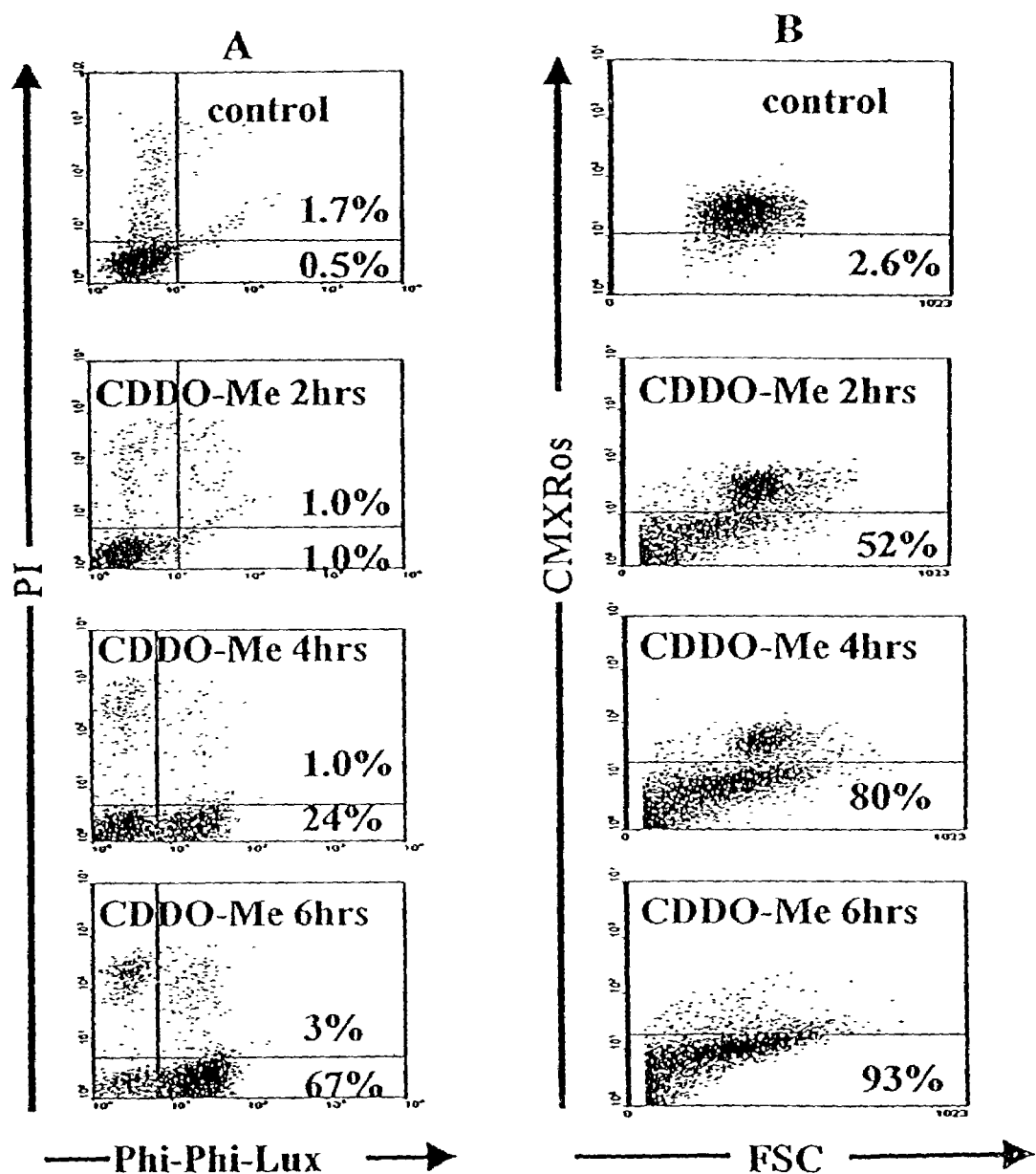
FIG. 24. CDDO-Me induces caspase activation and decreases mitochondrial potential in U937 cells.
Figure 25:
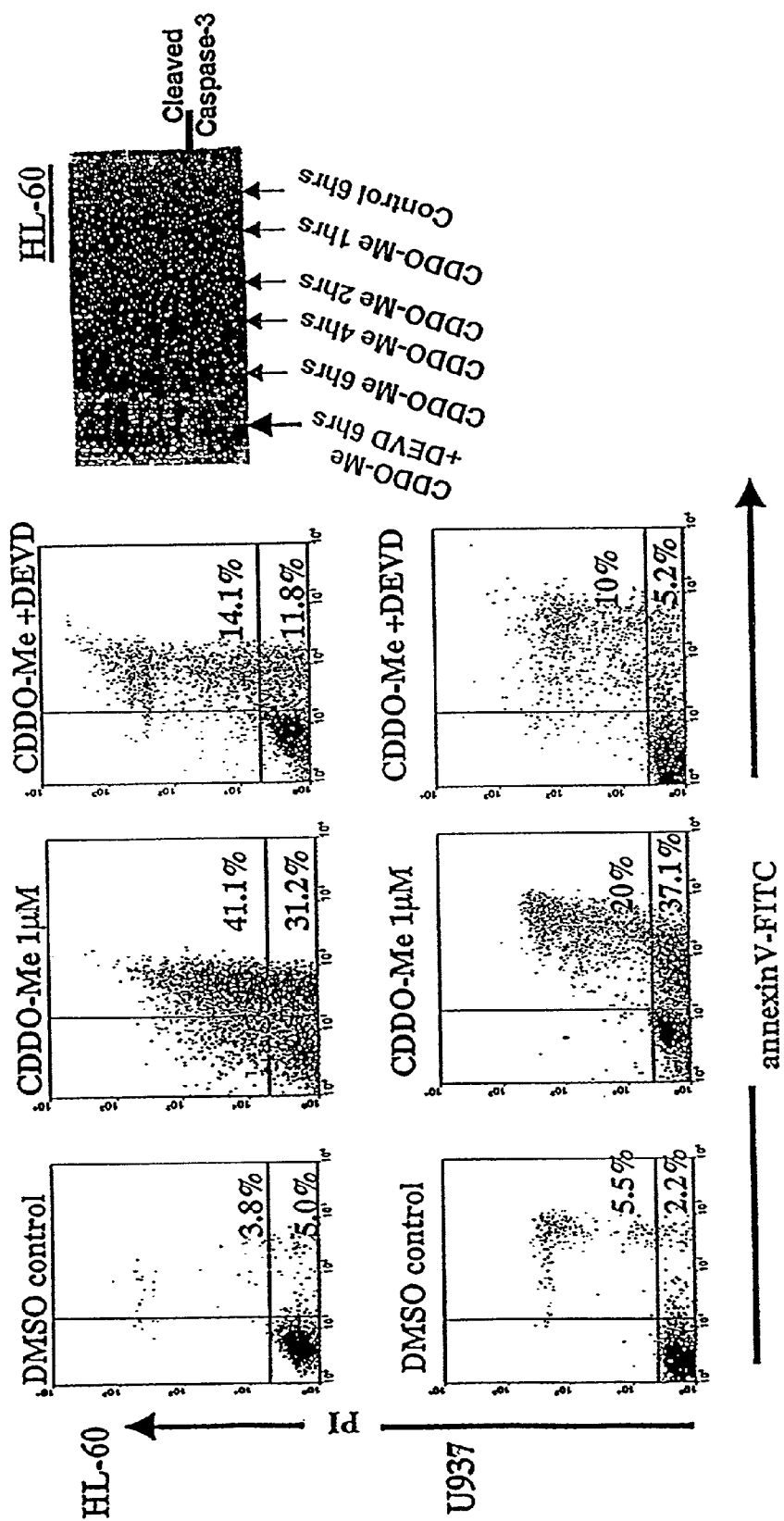
FIG. 25A.
FIG. 25B. Caspase-3 inhibitor DEVD blocks CDDO-Me induced annexin V positivity and caspase-3 cleavage.

CDDO-Me. The annexin/PI fluorimetric assay demonstrated a time-dependent increase in annexin V binding in CDDO-Me-treated cells (FIG. 23). Caspase-3 has been shown to play a pivotal role in the execution of programmed cell death induced by different stimuli (Ibrado et al., 1996; Ohta et al., 1997; Schlegel et al., 1996). Effects of CDDO-Me on the cleavage of caspase-3 were analyzed utilizing the fluorogenic substrate of caspase-3 Phi-Phi-Lux. As demonstrated in FIG. 24A, treatment of U937 cells with 1 µM CDDO-Me for 6 hours resulted in 67% of Phi-Phi-Lux positive/PI negative cells, indicating caspase cleavage. Activation of caspase-3 resulted in the appearance of the 17-kD proteolytic product of caspase-3 and complete disappearance of uncleaved 32-kD caspase-3 after 6 hours by Western blot analysis. Importantly, pre-treatment of U937 and HL-60 cells with 25 µM of caspase-3 inhibitor Z-DEVD-fmk for 1 hour significantly reduced annexin V-positivity (FIG. 25) and specifically diminished cleavage of Phi-Phi-Lux (from 15.1% to 2.7%). Western blot analysis using specific antibody for cleaved caspase-3 also demonstrated disappearance of the band (FIG. 25). These data confirm the key role of caspase-3 activation in the CDDO-Me-induced apoptosis.

Figure 26:
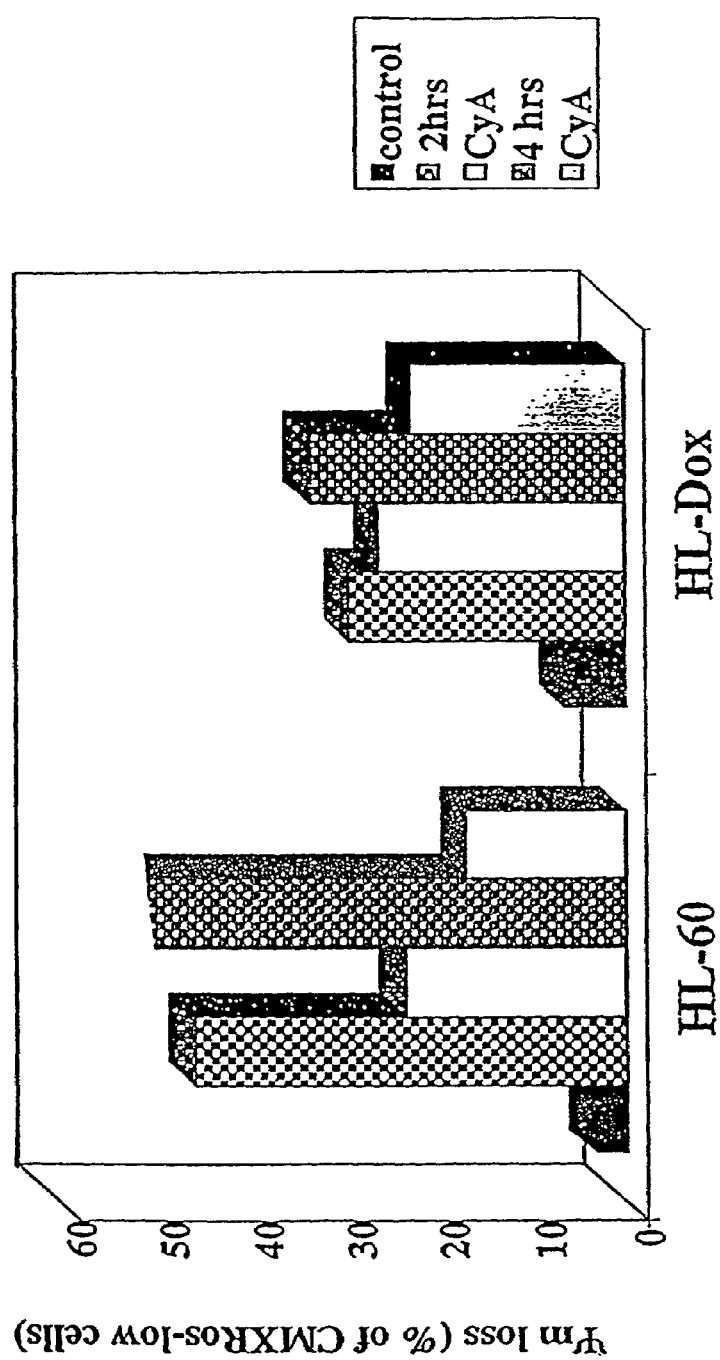
FIG. 26. CyA partially inhibits CDDO-Me-induced loss of mitochondrial potential.

An early mitochondrial disruption has been observed in a number of different models of apoptosis. Changes in the cellular content of the cationic lipophilic fluorochrome CMXRos were determined by FACS analysis to measure loss of the mitochondrial membrane potential ($\Delta\Psi$) (Macho et al., 1996). U937 cells exhibited a time-dependent decrease in $\Delta\Psi$ (FIG. 24B). Similarly, exposure of HL-60 to CDDO-Me (1 µM) for 2 and 4 hrs increased the number of cells with low JC-1 (57 and 60%) or CMXRos staining (46 and 57%), both assays measuring the decrease in $\Delta\Psi$. CDDO-Me-induced changes in the mitochondrial membrane potential of the cells preceded caspase activation and changes in the composition of the plasma membrane. In order to validate the role of the dissipation of $\Delta\Psi$ in CDDO-treated cells the pharmacological inhibitors of permeability transition cyclosporin A (CyA) (Nicolli et al., 1996) (10 µM, Sandoz) and bongkrekic acid (BA) (Marchetti et al., 1996) (Calbiochem, Calif.) were used. Addition of CyA partially inhibited CDDO-Me-triggered $\Delta\Psi$ loss, providing further evidence for effects of CDDO-Me on $\Delta\Psi$ (FIG. 26). The same effect was observed using BA (52% in CDDO-Me treated HL-60 cells, 23% when cells were pre-treated with BA). Notably, pretreatment with caspase inhibitor Z-DEVD-fmk also prevented appearance of cells with decreased $\Delta\Psi$ (40% in CDDO-Me-treated cells compared with 4% after DEVD pretreatment) in U937 cells suggesting the existence of caspase/mitochondria amplification loop. Collectively, these data demonstrate that CDDO-Me induces apoptotic cell death through activation of caspases and effects on the cellular mitochondrial potential.

Figure 27:
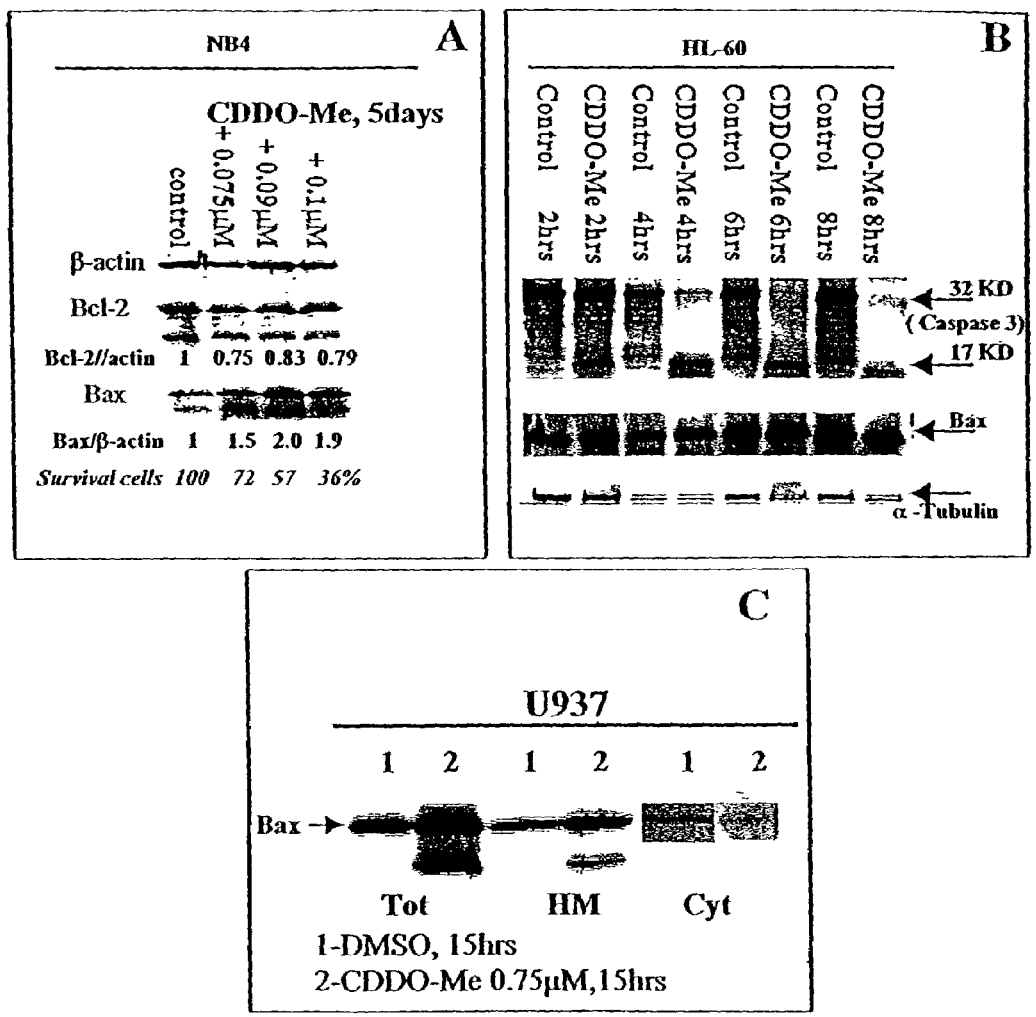
FIG. 27A, FIG. 27B and FIG. 27C. CDDO-Me induces Bax expression and caspase-3 cleavage.

The inventors then examined if CDDO-Me induced cell death by modulating the mitochondrial or the death receptor pathways of apoptosis. Thus, effect of CDDO-Me on Bcl-2 protein expression were studies. Prolonged (5 days) treatment with low concentrations of CDDO-Me (0.05 and 0.075 µM) did not significantly affect Bcl-2 expression levels in HL-60 and NB4 cells despite substantial cell killing, pointing to alternative mechanisms of induction of apoptosis by CDDO-Me (FIG. 27A). Bax functions as a promoter of cell death and its upregulation has been associated with enhanced apoptosis (Bargou et al., 1995; Yin et al., 1997). Treatment of HL-60 cells with CDDO-Me resulted in increased levels of Bax protein starting at 2 hrs with simultaneous cleavage of caspase-3 as determined by Western blot analyses (FIG. 27B). Bax levels were also induced when HL-60 and NB4 cells were treated for 5 days as described above (FIG. 27A). Bcl-2 and Bax are known to form heterodimers (Sato et al., 1994), and the ratio of anti-apoptotic versus proapoptotic dimers or the amount of free Bax are thought to be important in determining resistance of cells to apoptosis. In immunoprecipitation studies the inventors observed increased levels of Bcl-2 bound to Bax after 24 hrs of CDDO-Me indicating elimination of Bcl-2 anti-apoptotic function through binding to Bax. Effects of CDDO-Me on mRNA Bax levels were tested. As determined by Northern blot analysis, CDDO-Me treatment induced Bax mRNA in both HL-60 and U937 cells (FIG. 27C), hence CDDO-Me may affect transcriptional regulation of Bax.

Figure 28:
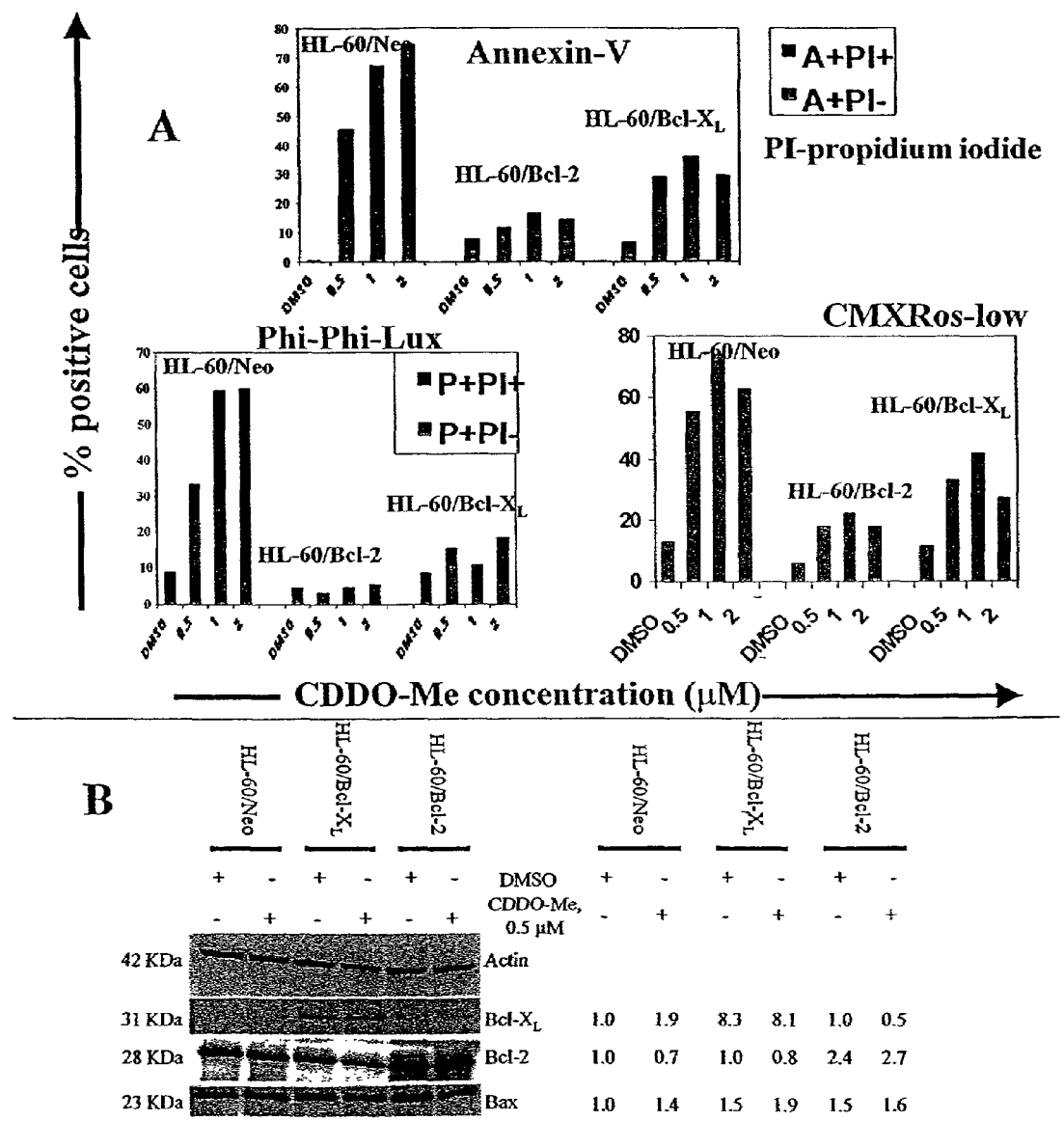
FIG. 28A and FIG. 28B. Overexpression of Bcl-2 and Bcl-Xl inhibits CDDO-Me induced apoptosis in HL-60 cells.
Figure 29:
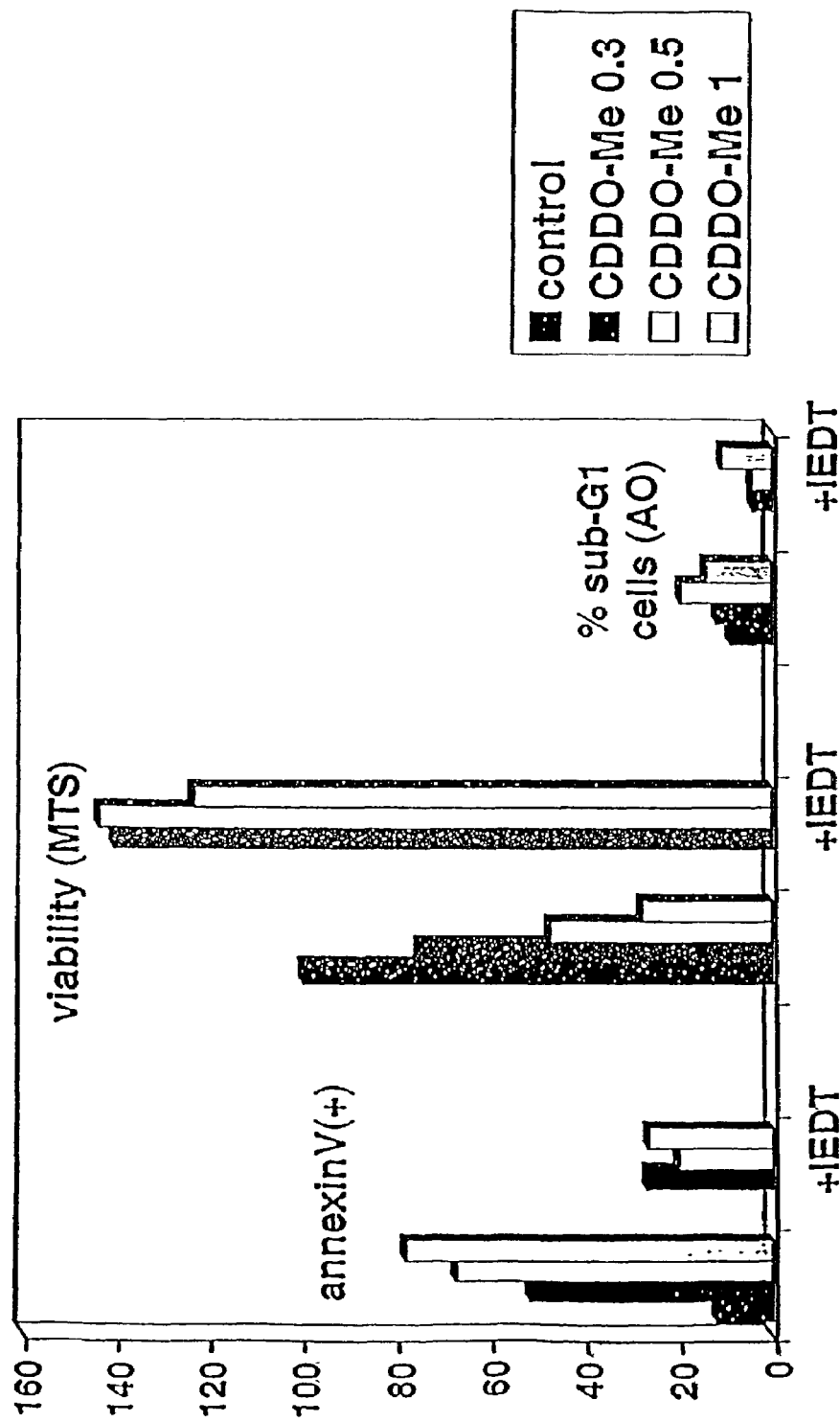
FIG. 29. Caspase-8 inhibitor IEDT prevents CDDO-Me induced apoptosis in NB4 cells.

To study if the overexpression of Bcl-2 can protect leukemic cells from CDDO-Me-induced cytotoxicity the inventors used U937 cells transduced with Bcl-2 (Vrana et al., 1999) and their empty-vector containing counterparts. Bcl-2 overexpression (3-fold) did not protect cells from CDDO-Me-killing. However, HL-60 cells overexpressing Bcl-2 exerted almost complete protection from CDDO-Me killing as determined by annexin V-positivity, Phi-Phi-Lux and CMXRos staining. HL-60/Bcl-$X_L$ cells were also partially protected from CDDO-Me cytotoxicity (FIG. 28A). While Bax protein levels increased in parental HL-60 and in HL-60/Bcl-$X_L$ cells, no difference in Bax levels were observed in HL-60/ Bcl-2 cells following treatment. In contrast, in p53-negative HL-60 and HL-60-Dox cells Fas was only not induced but IETD-FMK could also not prevent CDDO-Me-induced cell death, indicating involvement of different mechanisms of apoptotic cell death in these cells (Owen-Schaub et al., 1994). Anti-Fas blocking antibody ZB4 did not prevent CDDO-Me-induced killing in NB4 cells favoring direct activation of caspase-8. Thus, induction of the FasL/Fas/caspase-8 pathway is not essential in the execution of CDDO-Me-induced cell death. Post-translational modifications of Bcl-2 are involved in the regulation of apoptosis by CDDO-Me. Thus, Bcl-2 phosphorylation is inhibited by CDDO-Me.

The effect of CDDO-Me on Bcl-2 phosphorylation was further investigated by performing metabolic labeling studies with $^{32}$P-orthophosphoric acid. Following treatment with 0.1 µM of CDDO-Me (a concentration that induces apoptosis), Bcl-2 phosphorylation was virtually abrogated. To further investigate mechanisms of inhibition of Bcl-2 phosphorylation that could play a role in CDDO-Me-induced cell death, the inventors selected U937 cells that were stably transfected with a serine 70→alanine, Bcl-2 mutant (S70A). Previous studies demonstrated that the S70A mutant that is unable to be phosphorylated, was also incapable of protecting cells from chemotherapy-induced apoptosis. The U937/S70A Bcl-2 cells were found to be quite sensitive to CDDO-Me (60% decrease in viability following 0.1 µM of CDDO-Me). In contrast, a Ser→Glu mutant of Bcl-2, S70E, which may mimic a phosphate charge and was shown to be able to potently suppress apoptosis, was found to be much more resistant to CDDO-Me-induced apoptosis as compared to wild-type Bcl-2 (75% viable cells after 0.1 µM of CDDO-Me as compared to 30% for U937/wt). These data indicate that the phosphorylation status of Bcl-2 contributes to cell sensitivity to CDDO-Me-induced killing. Of note, U937/wt and the S70E and S70A Bcl-2 transfectants express roughly equivalent levels of Bcl2 protein as determined by densitometry, suggesting that the observed differential effects are not related to differences in Bcl-2 expression.

Since PKC-α and the MAP kinases ERK1 (p44) and ERK2 (p42) have been identified as physiologic Bcl-2 kinases, studies were performed to assess their activation status. Western blot analysis of subcellular fractions of U937 cells revealed that little, if any, PKC-α was co-localized with Bcl-2 in the mitochondrial membranes of U937 cells, suggesting that mitochondrial PKC is not a likely target of CDDO-Me. However, both ERK1 and ERK2 were prominently detected in the mitochondrial membranes. Furthermore, although treatment of cells with 1 µM CDDO-Me for 3 hours had no effect on the total ERK1/2 protein levels, CDDO-Me blocked the activation of ERK1/2, as shown by inhibition of ERK1/2 phosphorylation. Treatment of K562 cells with 1 µM of CDDO-Me in vivo abrogated ERK kinase activity similar to specific MEK inhibitor PD58059. No effect on Akt activity was seen. These findings indicate that CDDO-Me induces apoptosis by inhibition of ERK1/2 and Bcl-2 phosphorylation.

To determine specific effects of CDDO-Me on ERK activity the inventors used an in vitro MAPK kinase assay kit. ERK was immunoprecipitated from K562 cells since these cells contain the Bcr-Abl kinase and activated ERK present in these cells under basal conditions. CDDO-Me inhibited MBP phosphorylation in a dose-dependent manner. Similar effects were observed in HL-60 cells. These data indicate that there may be a direct effect of the compound on ERK kinase activity.

CDDO-Compounds and Retinoids Synergistically Decrease Viability and Induce Differentiation in Leukemic Cell Lines:

Combinations of CDDO-compounds and retionic acids were tested for anti-cancer therapy.

Figure 14:
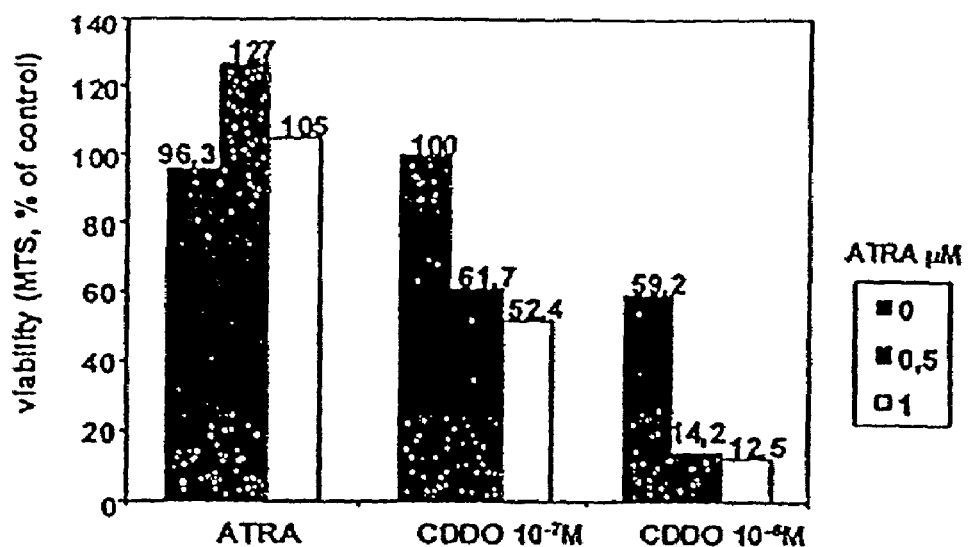
FIG. 14. ATRA enhances CDDO-induced growth inhibition of HL60 cells (72 hrs).

CDDO. HL-60 cells in the exponential growth phase were treated with 0.1 and 1 µM of CDDO-compounds alone or in combination with 0.5 or 1 µM of all-trans-retionic-acid (ATRA). Cell viability was measured after 48 hrs using the Cell Titer 96 AQ Non-Radioactive Cell Proliferation Assay (Promega, Madison, Wis.). Combination of CDDO with ATRA significantly decreased the viability of HL-60 cells (FIG. 14).

Figure 15:
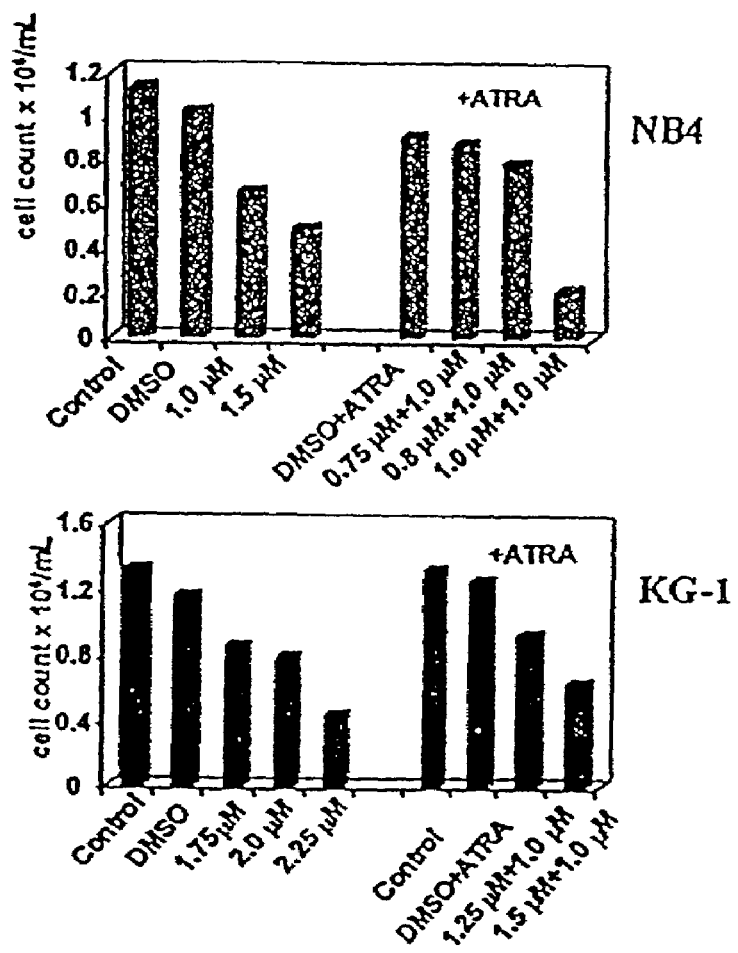
FIG. 15. ATRA (1 μM) enhances CDDO-induced cytotoxicity in leukemic cell lines.

Effect of CDDO/ATRA combinations were also tested in different leukemic cell lines. Leukemic cells cultured at 0.5× 10$^6$ cells/ml were treated with CDDO in indicated concentrations, alone or in combination with ATRA (FIG. 15). Combination of both agents decreased viable cell numbers in all cell lines tested by amounts that exceeded the effects seen by CDDO or ATRA alone.

Figure 16:
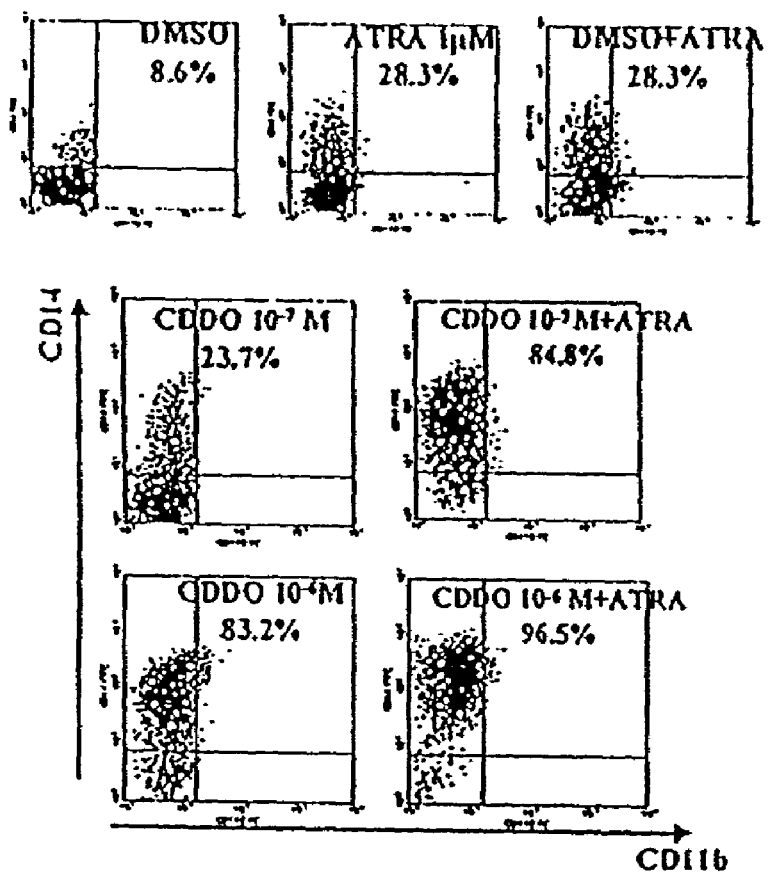
FIG. 16. ATRA enhances CDDO-induced differentiation of HL60 cells (72 hrs).

Enhancement in cellular differentiation using combinations of CDDO with ATRA were tested. HL-60 cells were cultured with different concentrations of CDDO (0.01, 0.1 and 1 µM) for 72 hrs, alone or in combination with 1 µM ATRA. Cell differentiation was analyzed by flow cytometry (CD14/CD11b staining). CDDO exhibited profound synergism with ATRA in induction of monocytic differentiation as demonstrated by CD14 induction (FIG. 16). These experiments were repeated 3 times and yielded essentially identical results.

Figure 17:
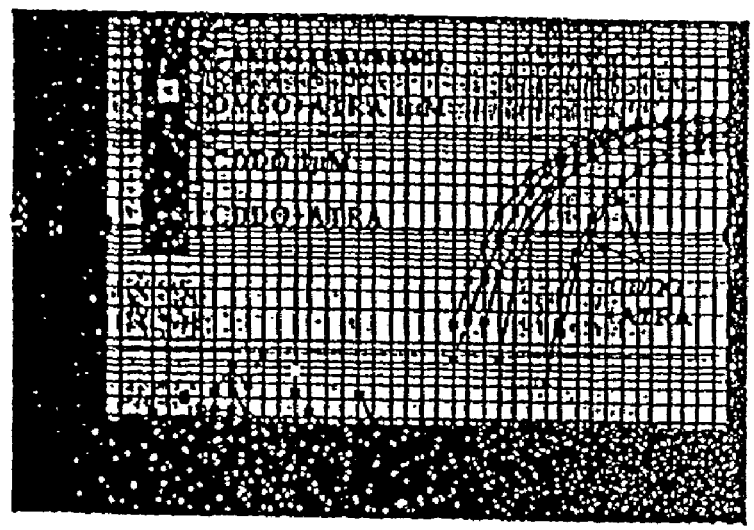
FIG. 17. CDDO combined with ATRA decreases Bcl-2 mRNA in U937 cells (24 hrs).

The present inventors have previously demonstrated that ATRA downregulates Bcl-2 mRNA and protein. Therefore, decreases in Bcl-2 mRNA and protein levels were analyzed in cells treated with combinations of CDDO and ATRA. Combined treatment of U937 cells with CDDO and ATRA induce significant decrease in Bcl-2 mRNA at 24 hours (FIG. 17). These data were confirmed by quantitative flow cytometry demonstrating decrease of Bcl-2 protein at 72 hours.

PPARγ and RXR are known to function as heterodimers. Therefore, the inventors contemplate combination treatments with CDDO-compounds and RXR-specific ligands and/or PPARγ ligands. The RXR-specific ligand LG-100268 (Ligand Pharmaceuticals) used at 1 and 10 nM significantly enhanced differentiation and cell killing in HL-60 cells (FIG. 18A, Table 5). This induction of differentiation and cell killing was more pronounced compared with ATRA when used at low concentrations (Table 5).

TABLE 5

RXR-specific ligand LG-100268 enhances CDDO-induced monocytic differentiation in HL-60 cells.

| CDDO µM | CDDO + ATRA | | | CDDO + LG100268 | | |
|---|---|---|---|---|---|---|
| | 0 | 0.5 | 1 | 0 µM | 0.5 µM | 1 µM |
| No ligand | 8.5 | 36.7 | 80.4 | 8.5 | 36.7 | 80.4 |
| 1 nM | 4 | 59 | 85.6 | 16.6 | 91.2 | 91 |
| 10 nM | 5.2 | 70.8 | 86.5 | 9.6 | 83.3 | Dead |
| 100 nM | 4.4 | 78.4 | Dead | 9.4 | 86.6 | Dead |

Results are expressed as a percentage of CD14 (+) live cells (FCM).

To confirm the specificity of the observed effects, HL-60 cells harboring a dominant-negative mutation in the retinoid receptor, with the normal retinoid receptors RXR-α and RAR-α was introduced by retroviral gene transfer (HL-60/RXR and HL-60/RAR cell lines. As demonstrated in FIG. 18B, RXR-specific ligand LG-100268 increased CDDO-induced apoptosis only in cells expressing RXR but not RAR receptor.

Figure 30:
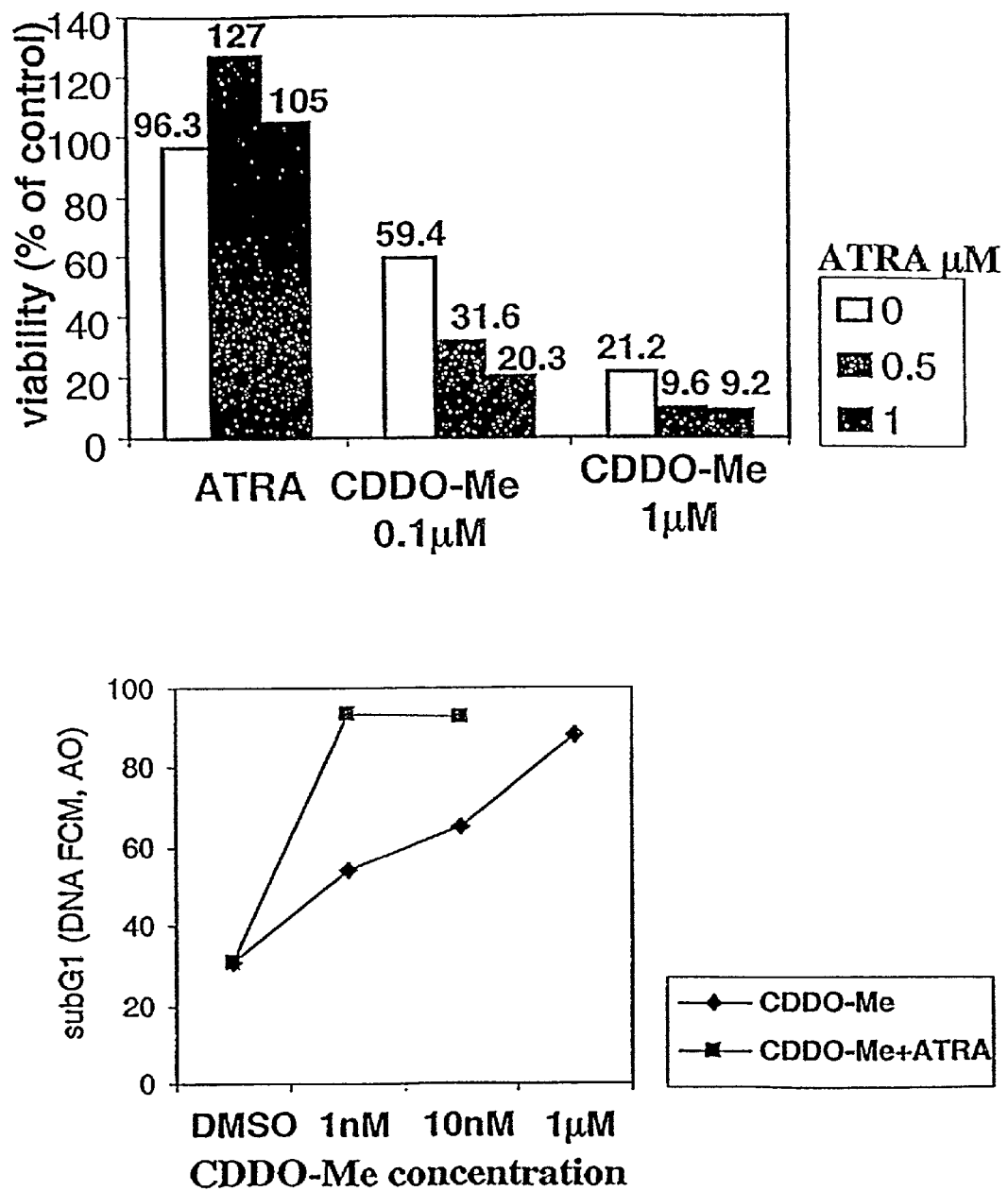
FIG. 30A and FIG. 30B. ATRA enhances CDDO-Me-induced cytotoxicity in HL-60 cells.
Figure 31:
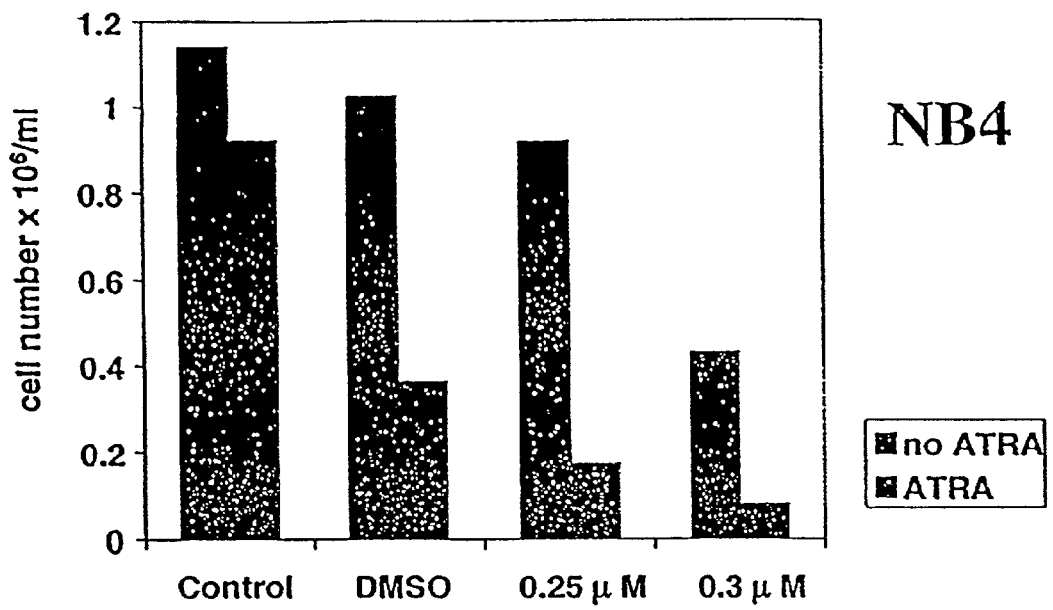
FIG. 31. ATRA (1 μM) enhances CDDO-Me-induced cytotoxicity in leukemic cell lines.
Figure 31:
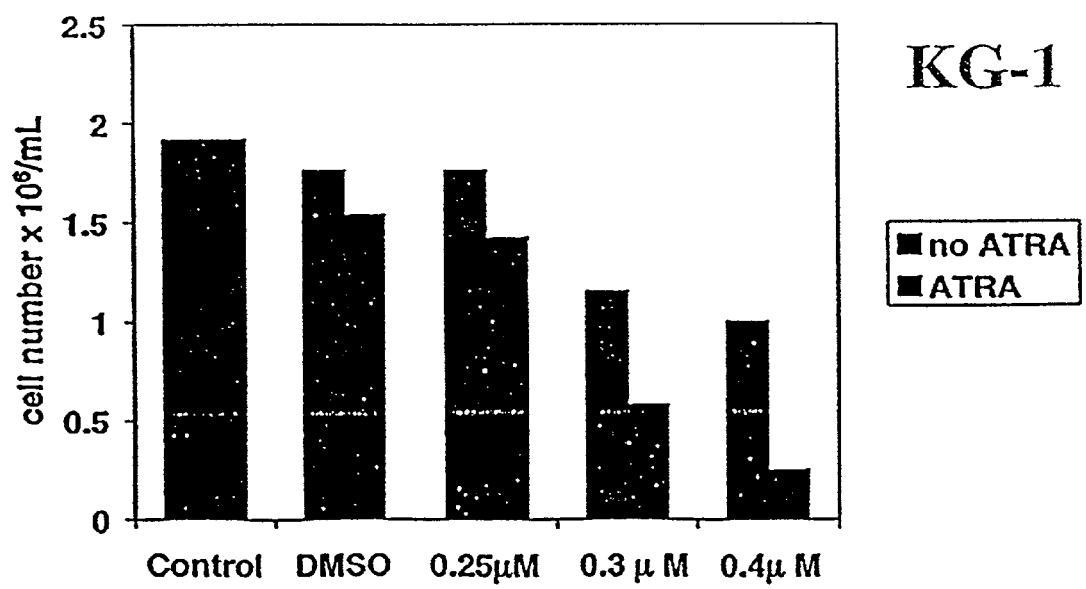
Figure 32:
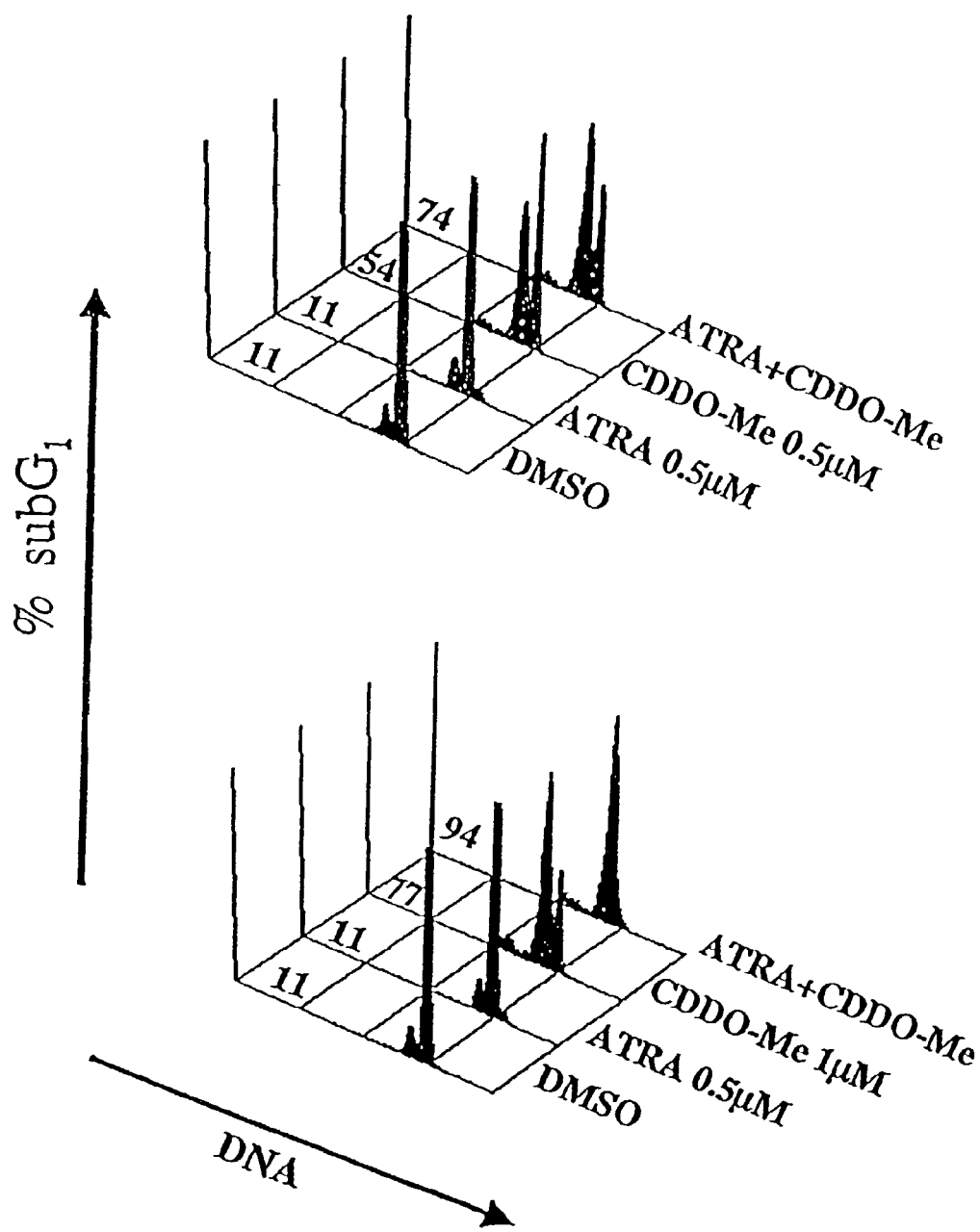
FIG. 32. ATRA enhances CDDO-Me-induced apoptosis in primary AML sample.

CDDO-Me. CDDO-Me and retinoids synergistically decrease viability and induce differentiation in leukemic cell lines. The inventors tested the Effect of CDDO-Me/ATRA combinations in different leukemic cell lines. The combination of CDDO-Me with ATRA significantly decreased the viability of HL-60 cells (FIG. 30A) and enhanced apoptosis in U937 cells (FIG. 30B). Combinations of both agents decreased viable cell numbers in all cell lines tested and exceeded the effects seen by CDDO-Me or ATRA alone (FIG. 31) indicating that combinations of both compounds activate apoptotic pathways. This was confirmed in HL-60 cells by annexin V staining (17.9 vs 30% positive cells when 0.1 µM of CDDO-Me was combined with 1 µM ATRA). In primary AML, ATRA enhanced CDDO-Me-induced apoptosis in ⅜ samples tested (an example of subG$_1$ flow cytometry in AML sample shown in FIG. 32).

The inventors and others previously demonstrated that ATRA downregulates Bcl-2 mRNA and protein (Andreeff et al., 1999; Bradbury et al., 1996). Therefore, the effects of combinations of CDDO-Me and ATRA on Bcl-2 protein level were studied. ATRA alone decreased Bcl-2 protein; however, no additive effect on Bcl-2 expression was noted when ATRA was combined with CDDO-Me.

Finally, the inventors examined if CDDO-Me combined with ATRA would enhance differentiation. HL-60 cells were cultured with of 0.1 µM of CDDO-Me for 72 hrs, alone or in combination with 1 µM ATRA. CDDO-Me exhibited profound synergism with ATRA in inducing granulo-monocytic differentiation as demonstrated by CD11b induction. At 48 hrs, 67.4% in CDDO-Me-treated cells and 63.5% in ATRA-treated cells were CD11b+ (compared with 40% in DMSO controls), while 85% of cells were positive when both compounds were given simultaneously. These studies were repeated 3 times and yielded essentially identical results. Next, combined treatment with CDDO-Me and RXR-specific ligand were tested for potentiation of anti-leukemic effects. RXR-specific ligand LG-100268 (Ligand Pharmaceuticals) used at 10, 100 nm and 1 µM enhanced killing of HL-60 cells in a dose-dependent manner (Table 6). At 1 µM of LG-100268 marked inhibition of cell growth was observed, and the percentage of cells in S+G$_2$M decreased by 50%. Collectively, these data demonstrate that CDDO-Me/retinoid combinations markedly decrease cell viability and induce terminal differentiation in myeloid leukemic cell lines.

TABLE 6

RXR-specific ligand LG-100268 enhances CDDO-Me-induced monocytic differentiation in HL-60 cells (24 hrs).

| CDDO-Me µM | CDDO-Me plus LG-100268 | |
| --- | --- | --- |
| | 0 | 0.1 |
| No Ligand | 4.4 | 22.4 |
| 10 nM | 6.8 | 34.4 |
| 100 nM | 6.2 | 40.3 |
| 1 µM | 6.3 | 61.6 |

CDDO-Compounds Inhibit Formation of Bone Marrow Endothelial Structures:

CDDO. PPARγ nuclear receptor is expressed in bone marrow endothelial cells, and PPARγ ligands inhibit inhibited endothelial cell proliferation. Recent data demonstrate an important role for the proliferation of endothelial cells, secretion of angiogenic factors and developing angiogenesis in the biology of leukemias. The present inventors therefore tested the effects of CDDO in endothelial cell assays. The formation of tube-like endothelial structures was performed using Matrigel®, a basement membrane matrix extracted from the Engelbreth-Holm Swarm mouse sarcoma cell line. Bone marrow endothelial cells with recombinant angiogenic cytokines were incubated in the presence or absence of CDDO, and formation of tube-like endothelial structures was assessed by direct observation using a inverted contrast-phase microscope. CDDO potently inhibited the formation of capillary-like structures by bone marrow endothelium (n=3). CDDO also diminished the proliferation of cytokine-stimulated vascular endothelial cells (HUVECs) as determined by [$^3$H]-Thymidine incorporation and by direct observation by inverted contrast-phase microscopy (n=3). Vascular endothelial cells (HUVEC) were grown in EBM-2 or EGM-2 media (Clonetics) containing VEGF, EGF, bFGF and IGF-1. The proliferation of endothelial cells was assessed by inverted contrast-phase microscope after 24 hrs of CDDO exposure in the indicated concentrations.

CDDO-Me. The formation of tube-like endothelial structures that are associated with angiogenesis was analyzed using a Matrigel system (Kubota et al., 1988). Capillary-like structure formation of bone marrow endothelium was inhibited by CDDO-Me. In addition, cytokine-stimulated vascular endothelial structure formation was also inhibited by CDDO-Me as determined by tritiated thymidine incorporation and phase-contrast microscopy. Furthermore, in a murine model of angiogenesis, angiogenic invasion promoted by ALL BM plasma was abrogated by CDDO-Me at 0.5 µM (n=8). Thus, CDDO-Me also has anti-angiogenic effects.

Example 3

AML NOD/Scid Model

AML CD34+38-cells are able to repopulate NOD/Scid mice (so called Scid-repopulating cells) (Lapidot et al., 1994). Recent data (Ailles et al., 1999) demonstrated consistent engraftment of AML in NOD/Scid mice: 8 weeks after the intravenous injection of 10$^7$ AML cells, the average percentage of human cells in mouse marrow was 13.3% (5.7% for "good" and 20.5% for "poor" cytogenetic abnormalities). These results provide a basis to use AML NOD/Scid system as the best pre-clinical model for AML. The present inventors therefore, established an AML-NOD/Scid model.

Figure 19:
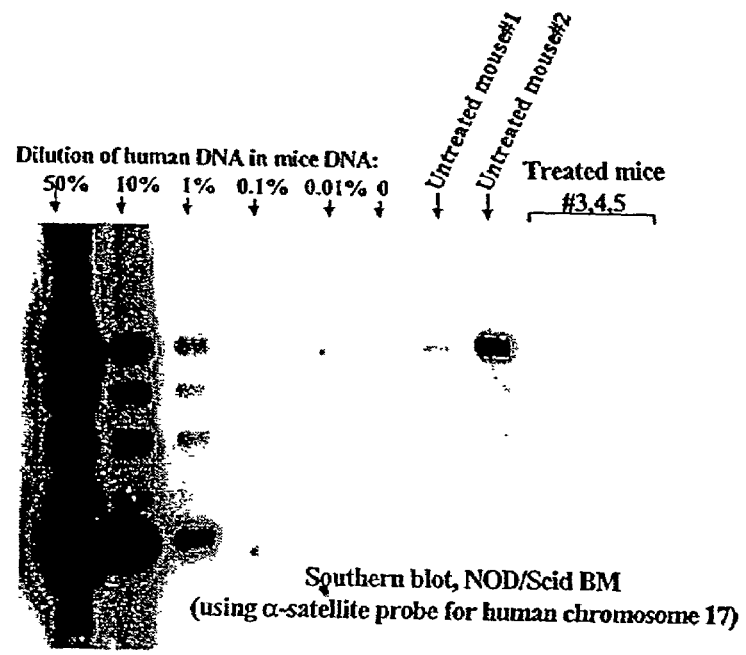
FIG. 19. Southern blot, NOD/Scid BM.

Each mouse was injected with 10$^7$ MACS-separated CD34+ leukemic cells. The engraftment of human leukemic cells is determined at 6-8 weeks after transplantation by CD45 flow cytometry and Southern blot analysis using human a-satellite probe for chromosome 17. The clonality of leukemic cells is determined by FISH based on the known karyotype of the samples studied. Under these conditions, consistent engraftment of AML was performed in 70% of cases. Phenotype of the leukemic cells and cytogenetic profile was similar to the characteristics of the patient's primary blasts. The CDDO-compounds are manufactured under GLP conditions utilizing the RAID program of CTEP as described above. Over 20 grams of each CDDO-compound is available for the proposed in vitro and in vivo studies. CDDO-compounds treatments provided to three AML-NOD/Scid mice resulted in lack of leukemic cells in the bone marrow in comparison to 2 untreated controls (FIG. 19).

The effect of CDDO on engraftment of leukemic cells was further tested in NOD/Scid mice transplanted with 1×10$^6$ human leukemic KBM-3 cells. Eleven mice were treated with CDDO at 6 mg/kg/day IP (divided in 3 injections per day) for 10 days; a control set of 9 mice received vehicle alone. The engraftment of human leukemic cells was determined by FISH based on the known karyotype of the cells (trisomy 8) at 5 weeks following transplantation. While 10.6±2.7% cells were leukemic in the bone marrow of the control group (range 0.12-21%), only 3±2.4% leukemic cells were found in CDDO-treated mice (range 0.04-12.5%, p=0.016). 5/11 CDDO-treated animals but only ⅛ controls had <1% leukemic cells by FISH analysis. Though preliminary, these results indicate anti-leukemic activity of CDDO in vivo.

CDDO-compounds Induce Growth Inhibition by Induction of Apoptosis and Differentiation in Myeloid Leukemias. Different in vitro and in vivo assays are contemplated to test cell killing induced in stromal cell-supported cultures, in clonogenic assays and in the NOD/Scid model transplanted with human leukemic cells. The enhancement of chemotherapy-induced apoptosis in AML by CDDO-compounds can also be examined by a person skilled in the art.

Effect of CDDO-compounds on the Proliferation, Differentiation and Apoptosis of Leukemic Cells from Primary AML. As CDDO-compounds decrease proliferation and induce apoptosis and differentiation in leukemic cell lines and in primary AML samples, effects of CDDO-compounds on allogenic stromal cell layers which resemble the in vivo stromal microenvironment can be tested. The inventors contemplate performing the following studies; experiments will be conducted with 50 primary AML samples. Samples containing >80% blasts will be used and samples with lower blast count will be enriched by magnetic separation (Vario-MACS, Miltenyi Biotech) for CD34+cells. This will include AML samples of different FAB subtypes and cytogenetic groups, at least 12 samples each will be tested for favorable (t(8;21), inv16, t(15;17)), intermediate (diploid) and poor-prognosis (all other abnormalities) cytogenetics.

Based on the preliminary paired data (mean=13.5%, std dev=14.4%), a sample size of 12 will yield 80% power with a two-sided one-sample t-test on the paired differences at level of significance 0.05 to test the hypothesis: Ho: difference in mean apoptosis for CDDO-compounds and DMSO is zero. Ha: CDDO-compounds results in 13.5% (absolute) more apoptosis than DMSO. (Note: a sample size of 15 will yield 85% power with Ha: CDDO-compounds results in 12.0% (absolute) more apoptosis than DMSO, or 91% power with Ha: CDDO-compounds results in 13.5% (absolute) more apoptosis than DMSO).

CDDO will be used at concentrations of 0.5, 1, 2 and 5 µM and CDDO-Me at 0.1, 0.3 and 0.5 µM for 72 hours. Effects on cells in suspension and adherent cells will be separately analyzed. Anti-proliferative effects of CDDO-compounds will be analyzed by cell count and histograms using propidium iodide and the analysis will be performed after gating on $CD34^+$ leukemic cells by flow cytometry. Apoptosis will be assayed by caspase cleavage (Phi-Phi-lux), PS/annexin V, and sub-$G_1$ DNA fragmentation. Induction of differentiation will be analyzed by flow cytometry of CD34, CD33, CD14, CD13 and CD11b.

The effect of CDDO-compounds on the clonogenic leukemic cells will be tested in the CFU-Blast assay, in extension of the results shown in FIG. 7. Fifty-eight AML samples of different FAB and cytogenetics groups (good vs. poor at 29 each) will be analyzed. Based on the preliminary data (mean=58%, std dev=11.2%) a sample size of 29 will allow the estimation of the % reduction in colony formation of AML progenitors (without regard to cytogenetics) with a 95% confidence interval with a bound on the error of estimation of 5% and coverage probability 0.90.

Effect of CDDO-compounds on NOD/Scid-repopulating AML progenitor cells. Each NOD/Scid mouse will be injected with $10^7$ MACS-separated CD34+ leukemic cells. The engraftment of human leukemic cells will be determined at 6-8 weeks after transplantation by CD45 flow cytometry and Southern blot analysis using human α-satellite probe for chromosome 17. The clonality of leukemic cells will be determined by FISH based on the known karyotype of the samples studied. The dose and route of administration (IV into tail vein, drinking water or via gavage) of CDDO-compounds will be determined and are described ahead.

Effects of CDDO-compounds in the NOD/Scid model using fresh or cryopreserved AML cells will be performed. About 50 AML samples will be analyzed for each experiment. A minimum of 6 mice will be injected with $10^7$ leukemic cells each. Three mice will be treated with CDDO-compounds 2 weeks after transplantation and 3 mice will remain untreated. As the leukemic cells will have engrafted in NOD/Scid mice by this timeframe, effects on leukemic cell growth will be determined. The inventors will estimate % reduction in NOD/Scid-repopulating AML cells with a 95% confidence interval.

As demonstrated above CDDO-compounds enhance ara-C killing in primary AML cells. Combinations of CDDO-compounds with ara-C and Doxorubicin will be tested at their respective $IC_{50}$ concentrations in primary AML (n=10) samples (n=10) in colony-forming assay. Based on the preliminary paired data (mean=11.4%, std dev=16.3%), a sample size of 19 will yield 80% power with a two-sided one-sample t-test on the paired differences at level of significance 0.05 to test the hypothesis: $H_o$: difference in mean cytotoxicity for (CDDO-compounds+ara-C) and ara-C alone is zero. Ha: (CDDO-compounds+ara-C) results in 11.4% (absolute) more cytotoxicity than ara-C alone. (Note: A sample size of 25 will yield 83% power with Ha: (CDDO-compounds+ara-C) results in 10.0% (absolute) more cytotoxicity than ara-C alone, or 91% power with Ha: (CDDO-compounds+ara-C) results in 11.4% (absolute) more cytotoxicity than ara-C alone.)

The normality assumption will be tested for the paired differences, and if the assumption is violated, an appropriate non-parametric procedure will be used to test the median difference in cytotoxicity between CDDO-compounds+ ara-C and ara-C alone.

Furthermore, the effects of CDDO-compounds on normal hematopoietic progenitor and stem cells will be tested. For these experiments, CD34+ MACS-separated bone marrow or apheresis-derived cells will be used. Toxic effect of CDDO-compounds will be tested on these normal progenitors in clonogenic assays and in the NOD/Scid model. The route and concentration of CDDO-compounds will be determined as described ahead. The inventors contemplate that these experiments will identify a "safe" therapeutic concentration range for CDDO-compounds. Based on preliminary data (mean=26.8%, std dev=7.5%) a sample size of 16 will allow the estimation of the % reduction in CFU-GM of normal CD34+ cells with a 95% confidence interval with a bound on the error of estimation of 5% and coverage probability 0.90. (Note: A sample size of 29 will allow the estimation of the % reduction in colony formation (without regard to cytogenetics) with a 95% confidence interval with a bound on the error of estimation of 3.3% and coverage probability 0.90. The sample size of 29 is that determined above for estimating the % reduction in AML progenitors.)

Example 4

Mechanisms of the Effects of CDDO-Compounds on Apoptosis in Leukemic Cells

The apoptotic pathways activated in response to the CDDO-compounds with regard to expression levels of Bcl-2 and induction of the CD95/Fas death receptor will be analyzed.

Intrinsic (mitochondrial) pathway. The inventors also contemplate examining if pro-caspase-9 is processed in leukemic cells in vitro in response to CDDO-compounds, thereby demonstrating the involvement of the mitochondriallcytochrome c pathway. In parallel, the inventors also contemplate studying drug-induced changes in the mitochondrial membrane potential ΔΨm using the cationic lipophilic fluorochrome CMXRos (Macho et al., 1996) and release of cytochrome c into the cytosol as assessed by subcellular fractionation studies Jurgensmeier et al., 1998; Matsuyama et al., 1998). To discriminate primary and secondary role of the mitochondrial damage in CDDO-compound-induced cell death all caspases will be blocked using the irreversible pan-caspase inhibitor zVAD-fmk. If mitochondrial damage precedes caspase activation and cell death, a $\Delta\Psi m$ loss and cytochrome c release despite the presence of zVAD-fmk is expected.

For these experiments, HL-60 and U937 cells will be treated in vitro with 1 µM CDDO or CDDO-Me in the presence or absence of 100 µM of zVAD-fmk. At 12, 24, 48 and 72 hours thereafter, $\Delta\Psi m$ will be quantitated by CMXRos fluorescence and endogenous caspase-3-like activity will be monitored using the cell-permeable fluorigenic substrate PhiPhi-LUX (Zapata et al., 1998.

As the Bcl-2 family of proteins are central to the regulation of the mitochondrial apoptotic pathway. The key function of Bcl-2-like proteins is to retain cytochrome c inside the mitochondria (Kluck et al., 1997; Yang et al., 1997). As shown herein CDDO-compounds decrease Bcl-2 expression at the mRNA and protein levels. CDDO-compounds cytotoxicity was also shown in Bcl-2-transfected U937 cells (with a 3-fold overexpression in the cells utilized). The inventors will further examine if CDDO-compounds can lower Bcl-2 levels below a critical threshold which permits apoptosis, even in cells overexpressing Bcl-2.

U937 and HL-60-transduced cells, selected for high levels of Bcl-2, and their respective vector-control counterparts will be treated with 1 µM CDDO or CDDO-Me for 72 hours. Bcl-2 protein levels will be determined by quantitative flow cytometry, and mRNA levels by TaqMan PCR. If dissipation of $\Delta\Psi m$ will precede Bcl-2 downregulation and apoptotic cell death in CDDO-compounds-treated cells, the inventors will test if pharmacological inhibitors of PT cyclosporin A and bongkrekic acid will inhibit mitochondrial alterations and apoptosis.

Extrinsic pathway. Fas/Fas-ligand can be induced by many cytotoxic drugs and is one of the mechanisms by which anticancer drugs kill cells (Friesen et al., 1996). Binding of FasL to Fas results in formation of the Fas death inducing signaling complex (DISC) with the prodomain of caspase-8 (Boldin et al., 1996; Muzio et al., 1996) and apoptosis. A p53-binding sequence was identified in the Fas promoter (Muller et al., 1998). The present inventors will investigate the activation of the Fas/Fas-ligand pathway in CDDO-compound mediated cell death in p53-wt cells (NB4).

The present inventors have demonstrated induction of CD95/Fas receptor in leukemic NB4 cells and in primary AML samples. The inventors will further investigate Fas-L expression levels and caspase-8 cleavage after treatment with CDDO-compounds. These experiments will be performed in NB4 cells treated with different concentrations of CDDO-compounds (0.5, 1 and 2 µM of CDDO) for 48 hours. Time-course experiments will also be performed in order to determine the induction of Fas/FasL and caspase-8 cleavage. In these experiments, Fas levels will be determined by flow cytometry. Fas-L and caspase-8 will be studied by Western blot analysis. The inventors contemplate that Fas- or Fas-L induction will precede capase-8 cleavage and apoptosis. Alternatively, in certain cells CDDO-compounds may directly induce caspase-8 activation without Fas- or Fas-L induction as was demonstrated in other cell systems (Wesselborg et al., 1999). Proteolytic processing of caspase-8, as well as downstream caspase-3, 6 and 7 will be monitored by immunoblotting. In parallel, the inventors will also assess caspase activity in cell extracts prepared from the same cells, using substrates that are relatively specific for caspase-8 (IEDT-AFC) and downstream effector caspases such as caspase-3 and 7 (DEVD-AFC). Caspase-8-like and caspase-3-like protease activity will be measured by fluorigenic assays using a spectrofluorometric plate reader ($EL_x808$, Bio-Tek Instruments, Inc., Winooski, Vt.) in the kinetic mode with excitation and emission wavelengths of 400 and 505 nm, respectively (Deveraux et al., 1997; Leoni et al., 1998). Activity will be measured by the release of 7-amino-4-trifluoromethyl-coumarin (AFC) from the synthetic peptidyl substrates.

The role of Fas in CDDO-compounds-induced apoptosis will also be analyzed by specific blockade of Fas receptor. Leukemic cells will be pre-treated with a Fas-blocking antibody (such as ZB4, 100 ng/ml, Immunotech, Miami, Fla.) for 1 hour prior to the CDDO-compound treatment. The endpoint will be the induction of apoptosis (annexin V and sub-$G_1$ DNA content). ZB4 blocked CDDO-compound-induced apoptosis indicates that the Fas/Fas-L interaction contributes significantly to the observed killing by CDDO-compounds. If no protection against killing by the CDDO-compounds is observed, the inventors will test the effect of a caspase-8 inhibitor (such as IEDT, Calbiochem, San Diego, Calif.). IEDT protection against the CDDO-compounds indicates that the CDDO-compounds activate caspase-8.

The inventors have demonstrated the expression of downstream inhibitors of both, intrinsic and extrinsic pathways, in AML cell lines and clinical samples. Specifically, XIAP and survivin, members of the inhibitor-of-apoptosis protein (IAP) family are overexpressed (Tamm et al., 1999; Carter et al., 1999). The inventors observed downregulation of XIAP mRNA and protein by CDDO. Further analysis of 20 primary AML samples with high (n=10) and low (n=10) XIAP and survivin levels with regard to their CDDO-compound sensitivity in stromal cell-supported culture systems are contemplated. This will elucidate the role of IAPs in the sensitivity and resistance to CDDO-compound-induced apoptosis.

Example 5

Promotion of CDDO-Compounds-Induced Cytotoxic Cell Death and Differentiation in Leukemic Cells by PPARγ

The present inventors have shown that CDDO-compounds specifically bind and transcativate the nuclear receptor PPARγ. This receptor and its heterodimeric partner RXR form a DNA-binding complex that regulates transcription of several target genes (Kliewer et al., 1992; Tontonoz et al., 1994). Ligation of PPARγ was reported to induce cell cycle arrest and differentiation Wu et al., 1996; Tontonoz and Spiegelman, 1994; Brunet al., 1996).

PPARγ expression in AML, ALL, and CML (Greene et al., 1995) cells is known but its biological function in hematopoietic cells has not been well investigated. A recent report by R. Evans's group demonstrates that other PPARγ ligands (15d-PGJ2 at 3 µM and BRL49653 at 5 µM) induce monocytic differentiation of HL-60 cells but do not exhibit killing (Tontonoz et al., 1998). PPARγ agonists decrease the transcriptional activity of Bcl-2-luciferase promoter construct (J Reed). The present inventors will assess the role of this signaling pathway in regard to the ability of the CDDO-compounds to induce differentiation and apoptosis.

Role of PPARγ in CDDO-compound-induced differentiation and apoptosis. To determine whether the expression of PPARγ is required for induction of differentiation and apoptosis by CDDO-compounds the inventors will examine their effect on the HL-60-derived subline CDM-1, which does not express PPARγ Nagy et al., 1995). Lack of induced differentiation and apoptosis in these cells by CDDO-compounds will indicate a critical role of PPARγ signaling in CDDO-compound-induced differentiation and/or apoptosis. In addition, PPARγ-receptor antagonists will be investigated for their ability to interfere with the activity of CDDO-compounds in PPARγ-expressing cells.

For quantitative assessment of differentiation, a morphological assessment of cells will be performed (for example by, Wright-Giemsa stained cytospin preparations), immunophenotype will be determined (CD11b/CD14 expression) and nitroblue tetrazolium reduction Drach et al., 1993). HL-60 and CDM-1 cells will be treated with different concentrations (0.3, 0.5, 1, and 2 μM) of CDDO for 72 hrs and apoptosis will be determined as described earlier. All experiments will be performed in triplicates.

If CDDO-compounds are found to be partially effective independently of PPARγ, the inventors contemplate that signaling through PPARγ may be complemented by other orphan receptors. In this case, the inventors contemplate investigating binding and transactivation of CDDO-compounds with other orphan receptors.

Comparison of CDDO-compounds with other PPARγ ligands. It is known that 15d-PGJ2 at 3%M and BRL49653 at 5 μM induces monocytic differentiation in HL-60 cells but do not cause cell killing. In contrast, CDDO induced monocytic differentiation at 0.5 to 1.0 μM and apoptosis at 1 μM in HL-60 cells. Therefore, the present inventors will compare 15d-PGJ2 (Alexis Corporation, San Diego, Calif.), BRL49653, oxidized low-density lipoprotein (OXLDL)(Intracel, Rockville, Md.) (Nagy et al., 1998) and CDDO from 0.1 to 10 μM in HL-60 and primary AML cells. Studies in primary AML (n=10) will be conducted at $IC_{50}$ concentrations and at concentrations that maximally induce differentiation in HL-60 cells. These experiments will define the ability of CDDO to induce differentiation and apoptosis in comparison to other PPARγ ligands. Similar experiments are contemplated with CDDO-Me.

Expression of PPARγ. The inventors have demonstrated that PPARγ is expressed in myeloid leukemic cell lines tested (HL-60, HL-60-DOX, U937, NB4, KG-1) and in 9/11 primary AML samples tested (see FIGS. 14, 15). PPARγ expression was also detected in lymphoid cells Jurkat, IM9, SupM2, Raji, SU-DHL and to a lesser extent in Daudi cells (see FIG. 13B). PPARγ protein was not detected in normal CD34+ cells (n=2). Thus, this invention provides that PPARγ is differentially expressed in normal and leukemic progenitor cells.

The inventors will further analyze PPARγ mRNA and protein expression in primary samples with AML and in normal CD34+cells by Northern blotting using $^{32}$P-labeled cDNA probe (Tontonoz et al., 1995). The inventors will then determine the effects of CDDO-compounds in the same samples (n=30) and correlate the efficacy of CDDO-compounds with PPARγ expression. Furthermore, the inventors will study primary AML samples with deletion of 3p25 (PPARγ mapping site) that do not express PPARγ. These studies will determine any correlation between PPARγ expression and the efficacy of CDDO-compounds.

The present inventors have demonstrated that CDDO-compounds downregulate mRNA expression of Bcl-2 anti-apoptotic genes. Several PPARγ agonists, including prostaglandin J2 and ciglitazone markedly suppressed the Bcl-2 promoter in Bcl-2 promoter-luciferase reporter assays. To determine whether changes in mRNA levels of Bcl-2 can be ascribed, at least in part, to differences in promoter activity induced by the CDDO-compounds, the inventors will transfect U937 cells (which expresses PPARγ) (Greene et al., 1995) with Bcl-2 luciferase reporter constructs. The inventors will then test the effect of CDDO or CDDO-Me and the other PPARγ agonist troglitazone on the Bcl-2 promoter-luciferase activity in transfected U937 cells.

Luciferase assay. U937 cells (2×10$^7$) will be transfected with 10-20 μg luciferase reporter DNA by electroporation at 875 V cm$^{-1}$, 960 μF (Bio-Rad Laboratories). After 1 hour recovery, transfected cells in triplicate samples will be treated with 1 μM CDDO or troglitazone. Luciferase activity will be assayed 18-36 h later using the Dual-luciferase reporter assay system (Promega) with the pRL-TK vector as the internal reporter control. Bcl-2 luciferase reporter encompasses the human 3.7 Kb Bcl-2 promoter region which contains both P1 and P2 transcription initiation sites.

The CDDO-compounds induce differentiation in leukemia cell lines and primary AML samples. In adipose tissue, ligation of PPARγ is known to induce differentiation of preadipocyte cells that is mediated by transcriptional activation of adipocyte-specific genes (Kliewer et al., 1992; Tontonoz et al., 1994). Specific hematopoietic gene promoters have not been tested for PPAR activation. To determine key downstream targets of PPARγ activation by CDDO-compounds, the inventors will use the Atlas cDNA expression array (Clontech) to identify genes whose expression are regulated by PPARγ activation. The inventors have already shown changes in the expression of 24 genes. Thus, new targets regulated by CDDO-compounds in primary AML samples will be identified by the analysis of isolated AML CD34+ cells (n=10). Differences in the expression levels ≧2-fold will be considered significant. Selected targets will be verified by RT-PCR, Northern and Western blotting.

To determine whether CDDO-compounds directly regulate transcription of the promoter of the target gene(s) identified by array analysis, the inventors will clone the region of the respective gene promoter into a luciferase reporter vector and cotransfect these constructs with CMX-mPPARγ expression vectors into CDM-1 cells. Following transfection, the cells will be treated with vehicle or 1 μM of CDDO or CDDO-Me. These experiments will determine if CDDO-compounds activate specific target genes directly through PPARγ.

Example 6

Synergistic Interactions between CDDO-Compounds and Retinoids in AML

Figure 18:
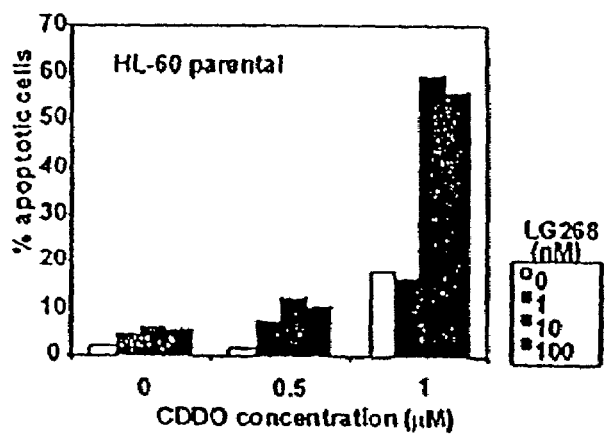
FIG. 18A. & FIG. 18B.
FIG. 18B. LG-100268 increases CDDO-induces killing in HL-60/RXR cells but not in HL-60/RAR cells.
Figure 18:
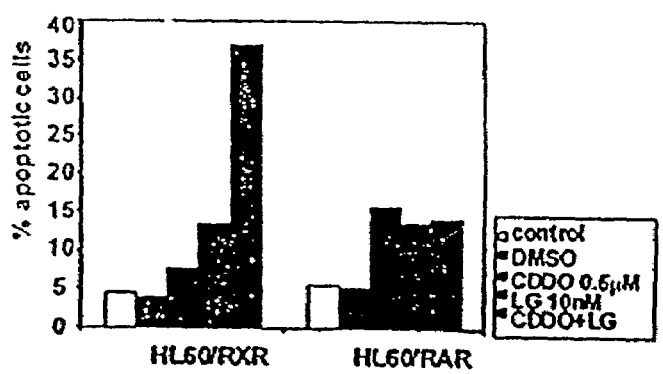

As demonstrated in Example 2, sub-micromolar combinations of the CDDO-compounds and ATRA or the RXR-specific ligand LG-100268 induce striking differentiation and apoptosis in HL-60 cells (FIG. 18 for CDDO). It is known that PPARγ and RXR form heterodimers, which upon concomitant ligation of both receptors exhibit maximal transcriptional activity (Kliewer et al., 1992; Tontonoz et al., 1994).

Interactions of retinoids with specific receptors can induce or suppress transcription of target genes. RAR can bind both ATRA and its naturally occurring double-bond isomer, 9-cis retinoid acid (9-cis RA), whereas RXR bind only 9-cis RA (Heyman et al., 1992). Activation of RAR-α is sufficient to induce differentiation, (Nagy et al., 1995; Mehta et al., 1996), whereas activation of RXR-α directly induces apoptosis via down-modulation of Bcl-2 mRNA and protein (Agarwal and Mehta, 1997). The inventors and others have demonstrated that ATRA transcriptionally downregulates Bcl-2 in AML (Andreeff et al., 1999). In normal hematopoiesis, Bcl-2 levels decrease dramatically during myeloid differentiation (Andreeff et al., 1999). This indicates that Bcl-2 functions as a downstream regulator of retinoid-induced cell growth and differentiation in hematopoietic cells.

Figure 34:
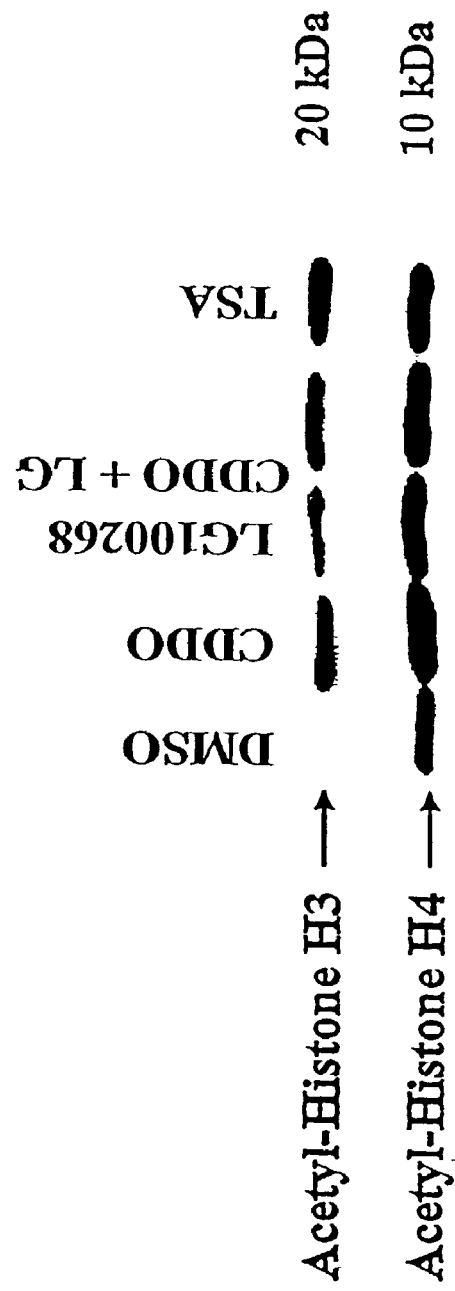
FIG. 34. CDDO induces histone acetylation in HL-60/RXR cells.

PPARγ must form a heterodimer with RXR to bind DNA and activate transcription (Nolte et al., 1998). RXR-specific ligands markedly induce the binding of the co-activator SRC-1 to PPARγ-RXR heterodimers (Westin et al., 1998), and assembly of this complex results in a large increase in transcriptional activity. The finding that SRC and CBP/p300 co-activator proteins possess intrinsic histone acetyltransferase activity indicate that ligand-mediated receptor transactivation may also involve targeted histone acetylation. One method to increase the effects of PPARγ ligands contemplated herein is by combination with ligands specific for RXR. Assembly of this complex results in a large increase in transcriptional activity. For example, in RXR-expressing HL-60 cells the inventors observed induction of acetylation of histones H3 and H4 by CDDO alone and in combination with RXR-specific ligand LG-100268 as determined by Western blot analysis of nuclear histones (see FIG. 34). TSA, the histone deacetylase inhibitor, served as a positive control. Combination of the PPARγ ligand CDDO with TSA synergistically induce differentiation in HL-60 cells and the present inventors contemplate that this is a result of transcriptional activation of target genes via histone acetylation.

Thus, combinations of CDDO-compounds and different retinoids will be tested in primary AML samples for increased spontaneous and chemotherapy-induced apoptosis. Primary samples will be studied for their sensitivity to CDDO-compound/retinoid combinations in suspension and in stromal-based cultures and in NOD/Scid model transplanted with human leukemic cells.

CDDO-compound/ATRA combinations induce apoptosis and differentiation in primary AML samples. The effect of CDDO-compounds and ATRA on apoptosis and differentiation will be assessed in 20 primary AML samples. The effects of CDDO-compounds and ATRA, alone and in combination, on apoptosis and differentiation of leukemic blasts will also be investigated. Apoptosis will be assessed by caspase cleavage (Phi-Phi-lux), PS/annexin V, and DNA fragmentation assays as described in the Examples above. Differentiation will be analyzed by expression of CD34, CD33, CD14, CD13 and CD11b by flow cytometry. The concentration levels of CDDO and CDDO-Me that will be tested initially are 0.1 µM, 0.3 µM, 0.5 µM, and 1 µM for 72 hours. The concentrations of ATRA that will be tested are 0 and 1 µM. This gives 4 concentrations of CDDO-compounds, 4 concentrations of CDDO-compounds+ATRA, and 1 concentration of ATRA alone for 4+4+1=9 treatment combinations. The controls will comprise a group with no treatment with either CDDO-compounds or ATRA. Therefore, 5 levels of CDDO-compounds (including 0) and 2 levels of ATRA (including 0) for a total of 5×2=10 treatment combinations. Thus, a 5×2 factorial experiment with 3 observations per treatment will be employed, giving a total of 30 observations. The data will be analyzed with a two-way analysis of variance with main effects (CDDO-compounds and ATRA) and an interaction term.

The inventors will therefore identify the combination of CDDO-compounds and ATRA that maximally induce apoptosis and/or differentiation. For evaluation of synergistic interactions the inventors will test a range of concentrations of both compounds and utilize the model described by Chou and Talalay, 1984.

Similar experiments will be performed with CDDO-compounds and the RXR-α specific ligand LG100268 in primary AML.

Effects of CDDO-compounds/ATRA and CDDO-compounds/LG100268 combinations on NOD/Scid-repopulating AML progenitors. The inventors will also test the effects of CDDO-compounds and ATRA or LG100268, alone and in combinations at concentrations identified above in the NOD/Scid model using fresh or frozen AML CD34+ cells. Ten AML samples will be tested for each combination. A minimum of 6 mice will be injected with $10^7$ leukemic CD34+ cells each. Three mice each will be treated with CDDO or CDDO-Me, ATRA, LG100268 and combinations 2 weeks after inoculation of the leukemic cells as described above in Example 3.

Mechanisms of CDDO-compounds/retinoid interactions. The inventors contemplate that the PPARγ agonist, CDDO-compounds, exerts synergistic effects with retinoids that activate the RXR receptor, due to the cooperative recruitment of coactivator SRC-1 by PPAR-RXR heterodimers. A synergistic effect observed with high concentrations of ATRA is due to its conversion into 9-cis RA under culture conditions (Heyman et al., 1992). The ability of ATRA to activate RXR in transactivation assays that is attributed to the isomerization into 9-cis-RA has been demonstrated (Mangelsdorf et al., 1990; Agarwal et al., 1996).

K562 cells will be transduced with RXR or RAR-α Parental K562 cells do not express RXR or RAR-α, are completely resistant to ATRA (Robertson et al., 1991) and will serve as controls. To determine whether RXR is required for CDDO-compound/retinoid effects on apoptosis and differentiation, if RXR-expressing cells respond to CDDO-compound/ATRA or CDDO-compound/LG100268 combinations, RXR is critical for CDDO-compound/retinoid interactions. If however, CDDO-compound/ATRA is effective in both, K562/RXR and K562/RAR-α cells, RAR-α may contribute to the combined effect of CDDO-compound/ATRA, by downregulation of Bcl-2 mRNA. In the latter case, the inventors will also investigate the effect of the RAR-specific ligand TTNPB (Sigma) in combination with CDDO-compounds.

To test the effects of ATRA and RXR-specific retinoid LG100268 combined with CDDO-compounds in K562 parental, K562/RAR and K562/RXR cells, the inventors will use ATRA and LG100268 at $10^{-6}$ to $10^{-9}$ M and 0.3 µM CDDO-compounds (a concentration that does not induce cell death), alone and in combination. K562 cells at the starting concentration $0.3\times10^6$ cells/ml will be cultured for 48, 72 and 96 hours. Apoptosis and differentiation will be determined as described above.

If RXR signaling is involved, the inventors anticipate synergistic effect of LG/CDDO-compounds combination in K562/RXR but not in parental or K562/RAR cells. This will be confirmed by the ability of the specific RXR antagonist (Ligand Pharmaceuticals, San Diego, Calif.) to block this effect.

If ATRA at low concentrations is synergistic with CDDO-compounds in K562/RAR cells, the involvement of RAR receptor signaling will be tested. First, a specific activator of RARs TTNPB, ((E)-4-[2-(5,6,7,8-tetrahydro-5,5,8,8-tetramethyl-2-naphthalenyl)-1-propenyl] benzoic acid), (Sigma) will be tested at $10^{-8}$ M, in combination with 0.3 µM CDDO or CDDO-Me. The pan-RAR-selective analog TTNPB exhibits high affinity to all three isoforms of RARs and is a potent inducer of their transcativation activity. It neither binds to RXR receptors nor transactivates their target gene expression (Nagy et al., 1995). If activation of RARs is involved, combined treatment with CDDO or CDDO-Me will elicit synergistic responses similar to ATRA in K562/RAR but not in parental or K562/RXR cells. This would be again confirmed by blocking of RAR-α with the antagonist (Allergan, Irvine, Calif.). K562/RAR-α-transfected cells will be cultured simultaneously with a sub-optimal concentration of ATRA (1 and 10 nmol/L) and increasing concentrations of the RAR- α-antagonist (0.05, 0.5, 1 µM) in the presence of 0.3 µM of CDDO or CDDO-Me for 72 and 96 hours.

The inventors have demonstrated that CDDO-compounds combined with 1 µM ATRA induce decrease in Bcl-2 mRNA in HL-60 cells. Further investigation to test if selective RAR/RXR ligands combined with CDDO-compounds will affect Bcl-2 mRNA and protein expression at sub-micromolar concentration are contemplated.

CDDO-compound/retinoid combinations exert their synergism by cooperative recruitment of co-activator SRC-1 to PPAR-RXR heterodimers. Transcriptional activation by nuclear receptors such as PPARγ and retinoid receptors requires recruitment of co-activator proteins, including SRC-1 (Onate et al., 1995; Kamei et al., 1996; Chakravarti et al., 1996; Torchia et al., 1997; Liu et al., 1998). The inventors will therefore study the combined effects of RAR-/RXR-specific ligands and CDDO-compounds on SRC-1 interactions with PPARγ-RXR heterodimers. The ability of LG-100268 and TTNPB at 10 nM and at their saturating concentration 1 µM, alone and combined with 0.1 and 1 µM of CDDO or CDDO-Me, to recruit $^{32}$P-labelled SRC-163373 to PPAR-RXR heterodimers bound to a PPAR responsive element (Kurokawa et al., 1994) will be analyzed. It is contemplated that LG-100268 but not TTNPB will induce binding of SRC-1 to PPARγ-RXR heterodimers, and that it will act synergistically with PPARγ-ligand CDDO-compounds.

Identification of new target genes for CDDO-compounds/RXR-ligand combination. Target genes that are activated by both, CDDO-compounds and the RXR-ligand LG100268, will be identified. A cell bank consisting of 12,000 vials of frozen cells from 2200 patients to will be used to identify activated genes utilizing the Atlas array (described in the Examples above). cDNA from specific AML samples that show synergistic responses to CDDO-compounds/retinoids will be analyzed and activated target genes will be validated as described above.

Example 7

PPARγ Nuclear Receptor as a Novel Therapeutic Target

PPAR-signaling is involved in cancer. The inventors have shown that the PPARγ protein is expressed in myeloid cell lines and in primary AML, ALL and CLL samples. CDDO is a PPARγ ligand and binds and transactivated PPARγ. Effects of the PPARγ ligands such as 15-deoxyΔ$^{12,14}$PGJ2, linoleic acid, thiazolidinediones (TZDs) such as troglitazone, BRL49653, and pioglitazone, L-805645, and GW347845X were tested on the proliferation, apoptosis and differentiation of leukemic cell lines. 15-deoxyΔ$^{12,14}$PGJ2, TZD and BRL49653 decreased the proliferation of leukemic cells as determined by cell count and $^3$H incorporation, with 15-deoxyΔ$^{12,14}$PGJ2 being most potent (IC50=5-10 µM). Six day treatment with 15-deoxyΔ$^{12,14}$PGJ2, BRL49653 and GW347845X induced CD11b expression in 1L-60 cells. Combination of TGZ with ATRA in U937 and THP1 cells, or 15-deoxyΔ$^{12,14}$pGJ2 with ATRA in HL-60 cells induced marked myelomonocytic differentiation followed by apoptosis of differentiated cells. TGZ+ATRA synergistically reduced the colony forming ability of THP1 and U937 cells and induced phagocytic activity in these cells. CDDO-compounds alone and in combination with retinoids such as ATRA also exert antiproliferative and apoptotic results on leukemic cell lines and primary AML, CLL and ALL samples in vitro as well as decreased Bcl-2 expression in leukemic blasts. Thus, novel PPARγ ligands, alone as well as in combination with retinoids or other chemotherapeutic compounds provide novel therapy for cancers especially leukemias. Ligation of PPARγ in combination with other chemotherapeutics especially retinoids provides maximal increase of transcriptional activity in target genes that control apoptosis and differentiation.

Example 8

Toxicity Pharmacokinetics and Tissue Distribution

Toxicity studies of CDDO-compounds in rats and mice were performed. Concentrations that were shown to exert biological effects in vitro (600 µg by gavage) did not result in any observed organ toxicity or premature death. Systematic subacute and chronic toxicity studies in BALB/c mice for CDDO-compounds are also presented. An HPLC assay for CDDO and CDDO-Me has been established and validated and will be utilize to investigate the pharmacokinetics and tissue distribution of the drug.

Subacute toxicity studies. An important aspect of this invention of CDDO-compounds and its combination therapies with other chemotherapeutics is to assess the toxicity and relative therapeutic efficacy of CDDO-compounds. The preliminary toxicity (i.e. determination of LD50 and MTD [maximum tolerated dose]) of CDDO-compounds was studied in healthy BALB/C mice (male and female, 25-30 g) after single i. v. or oral injections. Seven different dose levels (10 mice/dose level) were used after the appropriate pilot dosing experiments to define a MTD dose for both the oral and iv routes of administration. Animals were observed and weighed daily. The experiment was terminated on day 14. Surviving animals were sacrificed by exposure to carbon dioxide. The unit-dose effect line will be constructed and used to calculate lethal doses ($LD_{10}$ and $LD_{50}$).

Determination of MTD. 60 female Balb/C mice divided into 12 groups of 5 mice. With 5 mice per dose level, six dose levels for IV or oral drug administration were used.

Intravenous CDDO administration. Groups of mice received CDDO intravenously as a single bolus injection into the tail vein on Day 1. Euthanasia in a closed $CO_2$ chamber was after 14 days. Mice lost at other times are specified. The typical organs from each mouse that are examined include brain, heart, lungs, spleen, pancreas, kidneys, liver, gastrointestinal tract, lymph nodes, muscle, bone marrow, and skin. The lesions are described and the diagnoses are listed below for each animal. The major findings are given in Table 7 that follows to facilitate comparing groups of animals.

TABLE 7

| | | | IV CDDO Administration | |
|---|---|---|---|---|
| # | Ear Tag | Accession | Treatment | Diagnoses/observations |
| 1. | 349 | 0136 | 0.3 mg/kg | 1. Myeloid hyperplasia bone marrow |
| | | | | 2. Hyperplasia mesenteric lymph node |

TABLE 7-continued

IV CDDO Administration

| # | Ear Tag | Accession | Treatment | Diagnoses/observations |
|---|---|---|---|---|
| 2. | 350 | 0137 | 0.3 mg/kg | 1. Dystrophic calcification epicardium, heart<br>2. Myeloid hyperplasia bone marrow |
| 3. | 351 | 0138 | 0.3 mg/kg | Myeloid hyperplasia bone marrow |
| 4. | 352 | 0139 | 0.3 mg/kg | Myeloid hyperplasia bone marrow |
| 5. | 353 | 0140 | 0.3 mg/kg | 1. Dystrophic calcification epicardium, heart<br>2. Myeloid hyperplasia bone marrow<br>3. Hyperplasia cervical & mesenteric lymph nodes |
| 6. | 354 | 0141 | 1.0 mg/kg | No significant lesions |
| 7. | 355 | 0142 | 1.0 mg/kg | Hyperplasia cervical lymph nodes |
| 8. | 356 | 0143 | 1.0 mg/kg | 1. Lymphocytic sialoadenitis<br>2. Myeloid hyperplasia, bone marrow |
| 9. | 357 | 0144 | 1.0 mg/kg | Myeloid hyperplasia, bone marrow |
| 10. | 358 | 0145 | 1.0 mg/kg | Dystrophic calcification epicardium, heart |
| 11. | 359 | 0146 | 3.0 mg/kg | Myeloid hyperplasia, bone marrow |
| 12. | 360 | 0147 | 3.0 mg/kg | Myeloid hyperplasia, bone marrow |
| 13. | 361 | 0148 | 3.0 mg/kg | Myeloid hyperplasia, bone marrow |
| 14. | 362 | 0149 | 3.0 mg/kg | 1. Dystrophic calcification epicardium, heart<br>2. Myeloid hyperplasia bone marrow |
| 15. | 363 | 0150 | 3.0 mg/kg | Myeloid hyperplasia, bone marrow |
| 16. | 364 | 0151 | 10.0 mg/kg | 1. Myeloid hyperplasia bone marrow<br>2. Hyperplasia cervical lymph node |
| 17. | 365 | 0152 | 10.0 mg/kg | Myeloid hyperplasia, bone marrow |
| 18. | 366 | 0153 | 10.0 mg/kg | 1. Dystrophic calcification epicardium, heart<br>2. Myeloid hyperplasia spleen & bone marrow |
| 19. | 367 | 0154 | 10.0 mg/kg | 1. Myeloid hyperplasia bone marrow<br>2. Hyperplasia cervical lymph node |
| 20. | 368 | 0155 | 10.0 mg/kg | No significant lesions |
| 21. | 369 | 0156 | 30.0 mg/kg | 1. Myeloid hyperplasia bone marrow<br>2. Hyperplasia cervical lymph node |
| 22. | 370 | 0157 | 30.0 mg/kg | 1. Dystrophic calcification epicardium, heart<br>2. Myeloid hyperplasia bone marrow<br>3. Hyperplasia cervical lymph node |
| 23. | 371 | 0158 | 30.0 mg/kg | Myeloid hyperplasia, bone marrow |
| 24. | 372 | 0159 | 30.0 mg/kg | Myeloid hyperplasia, bone marrow |
| 25. | 373 | 0160 | 30.0 mg/kg | Lymphoid hyperplasia, spleen |
| 26. | 374 | 0130 | 100.0 mg/kg | EUTHANASIA @ 8 hours: moribund<br>1. Lymphocyte apoptosis thymus, spleen, lymph nodes<br>2. Dystrophic calcification epicardium, heart |
| 27. | 378 | 0131 | 100.0 mg/kg | EUTHANASIA @ 9 hours: moribund<br>1. Lymphocyte apoptosis spleen & lymph nodes<br>2. Hyperplasia mesenteric lymph nodes |
| 28. | 376 | 0132 | 100.0 mg/kg | EUTHANASIA @ 9 hours: moribund<br>1. Lymphocyte apoptosis spleen & lymph nodes<br>2. Myeloid hyperplasia, bone marrow |
| 29. | 375 | 0134 | 100.0 mg/kg | EUTHANASIA @ 10 days: tail necrosis<br>1. Myeloid hyperplasia spleen & bone marrow<br>2. Hyperplasia cervical lymph node<br>3. Hyperplasia GALT |
| 30. | 377 | 0135 | 100.0 mg/kg | EUTHANASIA @ 10 days: tail necrosis<br>1. Myeloid hyperplasia spleen & bone marrow<br>2. Hyperplasia cervical lymph node |

Oral CDDO administration. Groups of mice received CDDO oral gavage on day 1. Euthanasia was performed in a closed $CO_2$ chamber after 14 days. The typical organs from each mouse that are examined include brain, heart, lungs, spleen, pancreas, kidneys, liver, gastrointestinal tract, lymph nodes, muscle, bone marrow, and skin. The lesions are described and the diagnoses are listed below for each animal. The major findings are given in Table 8 that follows to facilitate comparing groups of animals.

TABLE 8

Oral CDDO Administration

| # | Ear Tag | Accession | Treatment | Diagnoses/observations |
|---|---|---|---|---|
| 1. | 379 | 0193 | 0.3 mg/kg | 1. Dystrophic calcification epicardium, heart<br>2. Myeloid hyperplasia bone marrow<br>3. Lymphoid hyperplasia spleen |
| 2. | 380 | 0194 | 0.3 mg/kg | 1. Myeloid hyperplasia bone marrow<br>2. Hyperplasia cervical & mesenteric lymph node |

TABLE 8-continued

Oral CDDO Administration

| # | Ear Tag | Accession | Treatment | Diagnoses/observations |
|---|---------|-----------|-----------|------------------------|
| 3. | 381 | 0195 | 0.3 mg/kg | 1. Dystrophic calcification epicardium, heart |
|   |     |      |           | 2. Myeloid hyperplasia bone marrow |
| 4. | 382 | 0196 | 0.3 mg/kg | No significant lesions |
| 5. | 383 | 0197 | 0.3 mg/kg | 1. Dystrophic calcification epicardium, heart |
|   |     |      |           | 2. Myeloid hyperplasia bone marrow |
|   |     |      |           | 3. Lymphoid hyperplasia spleen |
|   |     |      |           | 4. Hyperplasia GALT |
| 6. | 384 | 0198 | 1.0 mg/kg | 1. Dystrophic calcification epicardium, heart |
|   |     |      |           | 2. Hyperplasia cervical & mesenteric lymph node |
| 7. | 385 | 0199 | 1.0 mg/kg | Hyperplasia mesenteric lymph node |
| 8. | 386 | 0200 | 1.0 mg/kg | 1. Myeloid hyperplasia bone marrow |
|   |     |      |           | 2. Hyperplasia cervical lymph node |
|   |     |      |           | 3. Hyperplasia GALT |
| 9. | 387 | 0201 | 1.0 mg/kg | 1. Dystrophic calcification epicardium, heart |
|   |     |      |           | 2. Hyperplasia cervical lymph node |
| 10. | 388 | 0202 | 1.0 mg/kg | No significant lesions |
| 11. | 389 | 0203 | 3.0 mg/kg | Myeloid hyperplasia bone marrow |
| 12. | 390 | 0204 | 3.0 mg/kg | 1. Dystrophic calcification epicardium, heart |
|   |     |      |           | 2. Hyperplasia cervical & mesenteric lymph node |
| 13. | 391 | 0205 | 3.0 mg/kg | 1. Myeloid hyperplasia bone marrow |
|   |     |      |           | 2. Hyperplasia mesenteric lymph node |
| 14. | 392 | 0206 | 3.0 mg/kg | 1. Myeloid hyperplasia bone marrow |
|   |     |      |           | 2. Hyperplasia cervical lymph node |
| 15. | 393 | 0207 | 3.0 mg/kg | 1. Dystrophic calcification epicardium, heart |
|   |     |      |           | 2. Myeloid hyperplasia bone marrow |
|   |     |      |           | 3. Hyperplasia GALT |
| 16. | 394 | 0208 | 10.0 mg/kg | Myeloid hyperplasia bone marrow |
| 17. | 395 | 0209 | 10.0 mg/kg | 1. Myeloid hyperplasia bone marrow |
|   |     |      |           | 2. Hyperplasia cervical lymph node |
| 18. | 396 | 0210 | 10.0 mg/kg | 1. Dystrophic calcification epicardium, heart |
|   |     |      |           | 2. Myeloid hyperplasia bone marrow |
| 19. | 397 | 0211 | 10.0 mg/kg | 1. Chronic-active cystitis & pylonephritis |
|   |     |      |           | 2. Lymphoid hyperplasia spleen |
|   |     |      |           | 3. Myeloid hyperplasia bone marrow |
| 20. | 398 | 0212 | 10.0 mg/kg | No significant lesions |
| 21. | 399 | 0213 | 30.0 mg/kg | 1. Dystrophic calcification epicardium, heart |
|   |     |      |           | 2. Myeloid hyperplasia bone marrow |
|   |     |      |           | 3. Hyperplasia cervical & mesenteric lymph node |
| 22. | 400 | 0214 | 30.0 mg/kg | No significant lesions |
| 23. | 401 | 0215 | 30.0 mg/kg | 1. Myeloid hyperplasia bone marrow |
|   |     |      |           | 2. Hyperplasia GALT |
| 24. | 402 | 0216 | 30.0 mg/kg | 1. Dystrophic calcification epicardium, heart |
|   |     |      |           | 2. Hyperplasia cervical lymph node |
| 25. | 403 | 0217 | 30.0 mg/kg | Hyperplasia cervical lymph node |
| 26. | 404 | 0218 | 100.0 mg/kg | No significant lesions |
| 27. | 405 | 0219 | 100.0 mg/kg | 1. Dystrophic calcification epicardium, heart |
|   |     |      |           | 2. Myeloid hyperplasia bone marrow |
| 28. | 406 | 0220 | 100.0 mg/kg | Acute cholecystitis |
| 29. | 407 | 0221 | 100.0 mg/kg | 1. Dystrophic calcification epicardium, heart |
|   |     |      |           | 2. Hyperplasia cervical lymph node |
| 30. | 408 | 0222 | 100.0 mg/kg | Myeloid hyperplasia bone marrow |

NOTE:
Dystrophic calcification of the epicardium is a common incidental finding in mice (Vargas et al., 1996).

The majority of animals in both the intravenous and oral groups have myeloid hyperplasia of the bone marrow. This diagnosis is based upon finding the medullary cavities of decalcified bones filled with hematopoiesis that shows an overwhelming predominance of mature granulocytes. A few animals also had myeloid hyperplasia of the red pulp of the spleen (a normal site for extramedullary hematopoiesis). These hyperplastic changes are often encountered in mice without an apparent target and in the absence of known injury. Myeloid hyperplasia can be verified by doing a differential count on peripheral blood. If circulating granulocytes are not increased, then the appropriate diagnosis for increased granulocytes in the sites of myelopoiesis would be myeloid metaplasia.

The diagnosis of hyperplasia for lymph nodes, white pulp of the spleen, and gut-associated lymphoid tissue (GALT) is made when follicles with germinal centers are observed. As with the myeloid hyperplasia, this is a change that is commonly encountered in control, untreated mice and in mice from a wide variety of studies.

Intravenous CDDO-Me administration. Groups of mice received CDDO-Me intravenously as a single bolus injection into the tail vein on Day 1. Euthanasia in a closed $CO_2$ chamber was after 14 days. Mice lost at other times are specified. The typical organs from each mouse that are examined include brain, heart, lungs, spleen, pancreas, kidneys, liver, gastrointestinal tract, lymph nodes, muscle, bone marrow, and skin. The lesions are described and the diagnoses are listed below for each animal. The major findings are given in Table 9 that follows to facilitate comparing groups of animals.

TABLE 9

Intravenous CDDO-Me Administration

| # | Ear Tag | Accession | Treatment | Diagnoses/Observations |
|---|---------|-----------|-----------|------------------------|
| 1. | 431 | 0270 | 0 mg/kg | 1. Myeloid hyperplasia bone marrow<br>2. Hyperplasia cervical lymph node |
| 2. | 436 | 0271 | 0 mg/kg | Myeloid hyperplasia bone marrow |
| 3. | 441 | 0272 | 0 mg/kg | 1. Dystrophic calcification epicardium, heart<br>2. Myeloid hyperplasia bone marrow |
| 4. | 447 | 0273 | 0 mg/kg | Myeloid hyperplasia spleen & bone marrow |
| 5. | 452 | 0274 | 0.3 mg/kg | 1. Myeloid hyperplasia bone marrow<br>2. Hyperplasia mesenteric & subcutaneous lymph nodes |
| 6. | 428 | 0275 | 0.3 mg/kg | 1. Dystrophic calcification heart epicardium, heart<br>2. Myeloid hyperplasia bone marrow |
| 7. | 429 | 0276 | mg/kg | Myeloid hyperplasia bone marrow |
| 8. | 430 | 0277 | 0.3 mg/kg | 1. Dystrophic calcification epicardium, heart<br>2. Myeloid hyperplasia bone marrow |
| 9. | 432 | 0253 | 1.0 mg/kg | DIED @ 5 minutes |
| 10. | 433 | 0278 | 1.0 mg/kg | Dystrophic calcification epicardium, heart |
| 11. | 434 | 0279 | 1.0 mg/kg | Dystrophic calcification epicardium, heart |
| 12. | 435 | 0280 | 1.0 mg/kg | 1. Dystrophic calcification epicardium, heart<br>2. Myeloid hyperplasia bone marrow<br>3. Hyperplasia cervical lymph node |
| 13. | 437 | 0281 | 3.0 mg/kg | Myeloid hyperplasia bone marrow |
| 14. | 438 | 0282 | 3.0 mg/kg | 1. Myeloid hyperplasia bone marrow<br>2. Hyperplasia cervical lymph nodes |
| 15. | 439 | 0283 | 3.0 mg/kg | No significant lesions |
| 16. | 440 | 0284 | 3.0 mg/kg | Myeloid hyperplasia spleen & bone marrow |
| 17. | 443 | 02825 | 10.0 mg/kg | No significant lesions |
| 18. | 444 | 0286 | 10.0 mg/kg | Myeloid hyperplasia bone marrow |
| 19. | 445 | 0287 | 10.0 mg/kg | Dystrophic calcification epicardium, heart |
| 20. | 446 | 0288 | 10.0 mg/kg | Myeloid hyperplasia bone marrow |
| 21. | 448 | 0289 | 30.0 mg/kg | No significant lesions |
| 22. | 449 | 0290 | 30.0 mg/kg | Myeloid hyperplasia bone marrow |
| 23. | 450 | 0291 | 30.0 mg/kg | DRUG NOT ADMINISTERED<br>1. Dystrophic calcification epicardium, heart<br>2. Hyperplasia GALT |
| 24. | 451 | 0292 | 30.0 mg/kg | 1. Myeloid hyperplasia spleen & bone marrow<br>2. Hyperplasia cervical lymph nodes |
| 25. | 453 | 0293 | 100.0 mg/kg | Myeloid hyperplasia spleen & bone marrow |
| 26. | 454 | 0294 | 100.0 mg/kg | 1. Granulosa cell tumor (benign), ovary<br>2. Dystrophic calcification epicardium, heart<br>3. Myeloid hyperplasia spleen & bone marrow |
| 27. | 455 | 0295 | 100.0 mg/kg | Myeloid hyperplasia spleen & bone marrow |
| 28. | 456 | 0296 | 100.0 mg/kg | Myeloid hyperplasia spleen & bone marrow |

Oral CDDO-Me administration. Groups of mice received CDDO-Me oral gavage on day 1. Euthanasia was performed in a closed $CO_2$ chamber after 14 days. The typical organs from each mouse that are examined include brain, heart, lungs, spleen, pancreas, kidneys, liver, gastrointestinal tract, lymph nodes, muscle, bone marrow, and skin. The lesions are described and the diagnoses are listed below for each animal. The major findings are given in Table 10 that follows to facilitate comparing groups of animals.

TABLE 10

Oral CDDO-Me Administration

| # | Ear Tag | Accession | Treatment | Diagnoses/Observations |
|---|---------|-----------|-----------|------------------------|
| 1. | 501 | 0304 | 0 mg/kg | Focal acute to subacute lymphadenitis, cervical lymph node |
| 2. | 502 | 0305 | 0 mg/kg | No significant lesions |
| 3. | 503 | 0306 | 0 mg/kg | 1. Dystrophic calcification epicardium, heart<br>2. Hyperplasia cervical lymph node |
| 4. | 504 | 0307 | 0 mg/kg | Myeloid hyperplasia bone marrow |
| 5. | 505 | 0308 | 0 mg/kg | Myeloid hyperplasia bone marrow |
| 6. | 506 | 0309 | 0.3 mg/kg | 1. Hyperplasia cervical lymph nodes<br>2. Myeloid hyperplasia bone marrow |
| 7. | 507 | 0310 | 0.3 mg/kg | Myeloid hyperplasia bone marrow |
| 8. | 058 | 0311 | 0.3 mg/kg | Myeloid hyperplasia bone marrow |
| 9. | 509 | 0312 | 0.3 mg/kg | Dystrophic calcification epicardium, heart |

TABLE 10-continued

Oral CDDO-Me Administration

| # | Ear Tag | Accession | Treatment | Diagnoses/Observations |
|---|---------|-----------|-----------|------------------------|
| 10. | 510 | 0313 | 0.3 mg/kg | 1. Hyperplasia cervical lymph nodes |
|   |   |   |   | 2. Myeloid hyperplasia bone marrow |
| 11. | 511 | 0314 | 1.0 mg/kg | No significant lesions |
| 12. | 512 | 0315 | 1.0 mg/kg | 1. Focal chronic myocarditis, IVS, base of heart |
|   |   |   |   | 2. Myeloid hyperplasia bone marrow |
| 13. | 513 | 0316 | 1.0 mg/kg | 1. Hyperplasia cervical & mesenteric lymph nodes |
|   |   |   |   | 2. Chronic, unilateral pyelonephritis |
| 14. | 514 | 0317 | 1.0 mg/kg | No significant lesions |
| 15. | 515 | 0318 | 1.0 mg/kg | Myeloid hyperplasia bone marrow |
| 16. | 516 | 0319 | 3.0 mg/kg | No significant lesions |
| 17. | 517 | 0320 | 3.0 mg/kg | 1. Hyperplasia cervical lymph nodes |
|   |   |   |   | 2. Myeloid hyperplasia bone marrow |
| 18. | 518 | 0321 | 3.0 mg/kg | Dystrophic calcification epicardium, heart |
| 19. | 519 | 0322 | 3.0 mg/kg | 1. Dystrophic calcification epicardium, heart |
|   |   |   |   | 2. Myeloid hyperplasia bone marrow |
| 20. | 520 | 0323 | 3.0 mg/kg | No significant lesions |
| 21. | 521 | 0324 | 10.0 mg/kg | 1. Dystrophic calcification epicardium, heart |
|   |   |   |   | 2. Hyperplasia cervical lymph nodes |
| 22. | 522 | 0325 | 10.0 mg/kg | 1. Dystrophic calcification epicardium, heart |
|   |   |   |   | 2. Hyperplasia cervical & mesenteric lymph nodes |
|   |   |   |   | 3. Focal granulomatous fasciitis, serosa, urinary bladder |
| 23. | 523 | 0326 | 10.0 mg/kg | 1. Hyperplasia cervical lymph nodes |
|   |   |   |   | 2. Myeloid hyperplasia bone marrow |
| 24. | 524 | 0327 | 10.0 mg/kg | Dystrophic calcification epicardium, heart |
| 25. | 525 | 0328 | 10.0 mg/kg | 1. Hyperplasia cervical lymph nodes |
|   |   |   |   | 2. Subacute, unilateral pyelonephritis |
|   |   |   |   | 3. Myeloid hyperplasia bone marrow |
| 26. | 526 | 0329 | 30.0 mg/kg | Dystrophic calcification epicardium, heart |
| 27. | 527 | 0330 | 30.0 mg/kg | Dystrophic calcification epicardium, heart |
| 28. | 528 | 0331 | 30.0 mg/kg | Dystrophic calcification epicardium, heart |
| 29. | 529 | 0332 | 30.0 mg/kg | No significant lesions |
| 30. | 530 | 0333 | 30.0 mg/kg | No significant lesions |
| 31. | 531 | 0334 | 100.0 mg/kg | 1. Necrotizing pericarditis |
|   |   |   |   | 2. Dystrophic calcification epicardium, heart |
|   |   |   |   | 3. Necrotizing pleuritis & pheumonitis |
|   |   |   |   | 4. Myeloid hyperplasia spleen & bone marrow |
|   |   |   |   | 5. Lymphoid atrophy spleen |
|   |   |   |   | 6. Erythroid atrophy bone marrow |
| 32. | 532 | 0335 | 100.0 mg/kg | Dystrophic calcification epicardium, heart |
| 33. | 533 | 0336 | 100.0 mg/kg | Dystrophic calcification epicardium, heart |
| 34. | 534 | 0337 | 100.0 mg/kg | No significant lesions |
| 35. | 535 | 0338 | 100.0 mg/kg | No significant lesions |

Dystrophic calcification of the epicardium is a common finding in mice (Vargas et al., 1996). The majority of animals in both the intravenous and oral groups have myeloid hyperplasia of the bone marrow. This diagnosis is based upon finding the medullary cavities of decalcified bones filled with hematopoiesis that shows an overwhelming predominance of mature granulocytes. A few animals also had myleoid hyperplasia of the red pulp of the spleen (a normal site for extramedullary hematopoiesis). These hyperplastic changes are often encountered in mice without an apparent target and in the absence of known injury.

The diagnosis of hyperplasia for lymph nodes, white pulp of the spleen, and gut-associated lymphoid tissue (GALT) is made when follicles with germinal centers are observed. As with the myeloid hyperplasia, this is a change that is commonly encountered in control, untreated mice and in mice from a wide variety of studies.

Chronic toxicity studies. For these studies, Balb/c mice of both sexes will be treated with 10 weekly i. v. doses of 20%, 30%, 40% and 50% of the predetermined single dose LD10 of CDDO-compounds. Animals will be weighed weekly and survival rates in different groups will be recorded. Differences in toxic doses between sexes and between routes of administration will be determined and compared.

Analytical Assays and Pharmacokinetics. Understanding the pharmacokinetics and tissue distribution of CDDO-compounds is necessary for optimal application of this agent in the clinical setting and for adequate interpretation of preclinical toxicity and efficacy data. It is clear, however, that before pharmacokinetic and biodistribution studies of CDDO-compounds can proceed, there must be reliable, validated methods with sufficient sensitivity and specificity to quantify low levels of CDDO-compounds in relevant biological matrices (i.e. plasma and urine). The inventors have developed and validated an HPLC/UV based method for determination of CDDO-compounds. Coordinate with this assay is the development of a parallel assay using LC/MS that can be used for determination of CDDO-compounds metabolites. The drug is well suited to extraction using solid phase C18 cartridges. Analysis of the drug can be accomplished using one of two methods. The first involves an HPLC (Waters Alliance system) equipped with a Bondapak C18, 5 micron particle size reverse phase column (with UV detection at 284 nm) where the isocratic mobile phase consists of ammonium acetate buffer and acetonitrile (50:50, v:v). Analyses of the drug and its metabolites can be determined using a Micromass Platform mass spectrometer with electrospray ionization (positive mode) where examination of the m/z 492 ion [positive electrospray mode] is followed. Both assays use a methyl ester derivative of CDDO as an internal standard.

CDDO-compounds prepared in DMSO (10 mg/ml) will be injected i.p. or orally (by gavage) into Balb/c mice at the respective MTD doses. At selected time points post-injection (5 min, 15, 30, 45 min, 1 hr, 2, 4, 8, 12, 24, 48 and 72 hr), groups of mice will be killed (5 mice per time point), and plasma prepared from blood. Samples will be frozen at −80° C. until analysis. Separate groups (n 5) of mice will be placed in metabolism cages and urine and feces collected every 8 hr for 48 hr to determine elimination of CDDO-compounds and related metabolites. Mice sacrificed for pharmacokinetic studies will immediately be used to harvest tissues (e.g. liver, spleen, lung, heart, kidney, small intestine, large intestine, and skeletal muscle) in order to determine tissue distribution of CDDO-compounds. The 72-hr time point is necessary to insure adequate sampling of the CDDO-compounds elimination phase. Plasma and urine samples will be extracted and analyzed as previously described. The concentration of CDDO in each sample will be calculated by determining the ratio of the CDDO-compounds peak area to that of the corresponding peak of the internal standard CDDO methyl ester and by comparing the ratio with a standard curve prepared in the appropriate matrix. All pharmacokinetic parameters will be analyzed by non-compartmental analysis using the WIN-NONLIN software program. CDDO-compound's elimination half-life (t½), area under the curve (AUC), volume of distribution (Vd), clearance (Cl), and peak plasma (Cmax) will be calculated. In addition, total fecal and urinary clearance of CDDO will be determined as well as relative oral bioavailability.

Tissue distribution. Organs harvested from Balb/c mice at various time points post-injection can be harvested, blotted, weighed, and homogenized. A portion of homogenized samples can be extracted and analyzed as described above.

Antitumor Efficacy. The relative antitumor efficacy of CDDO-compounds and its combinations with chemotherapeutics such as retinoids can also be assessed against both human solid tumors (MX1 breast, HT29 colon and BRO melanoma) as well as against human leukemia cell lines in SCID mice.

Example 9

In Vivo Effects of CDDO

Figure 35:
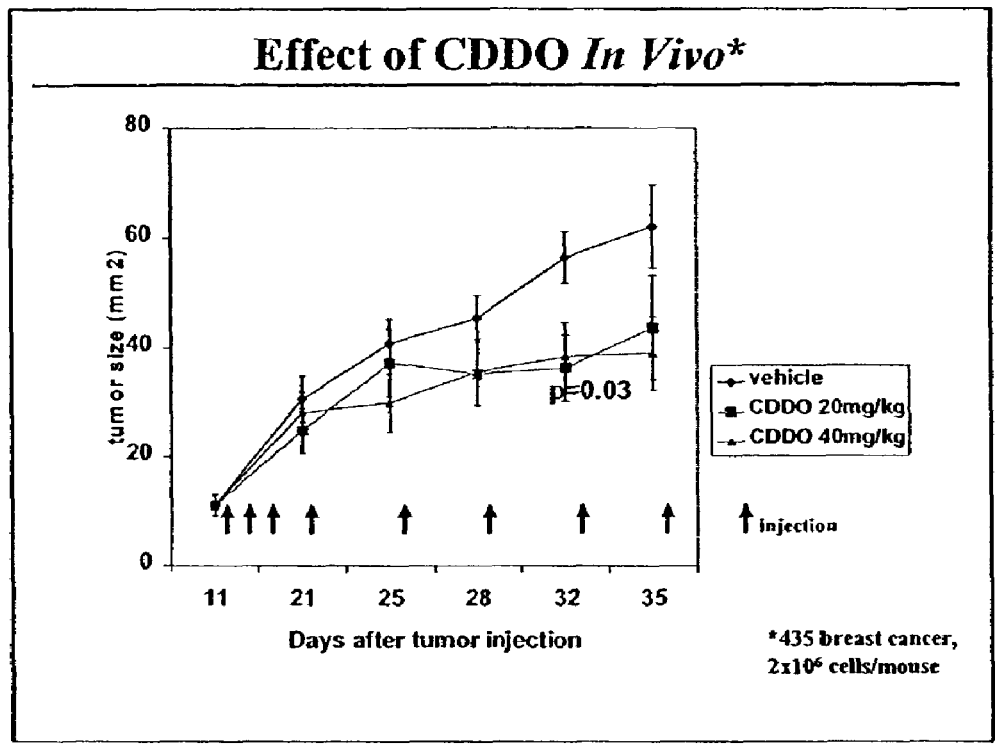
FIG. 35. Activity of CDDO against breast-cancer cells in vivo.

The activity of CDDO against breast cancer cells has also been demonstrated in vivo. CDDO was given at 20 and 40 mg/kg i.v. twice a week 10 days after nude mice were injected s.c. with 2×10⁶ estrogen-receptor negative, PPARγ positive 435 breast cancer cells. Results shown in FIG. 35 demonstrate that CDDO inhibits the growth of breast cancer cells in vivo at both concentrations used.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Agarwal and Mehta, "Possible involvement of Bcl-2 pathway in resinoid X receptor alpha-induced apoptosis of HL-60 cells," *Biochem Biophys Res Common,* 230(2):25 1-253, 1997.

Agarwal, Chandraratna, Teng, Nagpal, Rorke, Eckert, "Differential regulation of human ectocervical epithelial cell line proliferation and differentiation by resinoid X receptor- and resinoid acid receptor-specific retinoids," *Cell Growth Differ,* 7(4):521-530, 1996.

Ailles, Gerhard, Kawagoe, Hogge, "Growth characteristics of acute myelogenous leukemia progenitors that initiate malignant hematopoiesis in nonobese diabetic/severe combined immunodeficient mice," *Blood,* 94(5):1761-1772, 1999.

Andreeff, "Acute myeloid leukemia," In: *Cancer Treatment,* Haskell (Ed.), W. B. Saunders, 911-922, 1995.

Andreeff, Jiang, Zhang, Konopleva, Estrov, Snell, Xie, Okcu, Sanchez-Williams, Dong, Estey, Champion, Komblau, Reed, Zhao, "Expression of bcl-2-related genes in normal and AML progenitors: Changes induced by chemotherapy and cationic acid," *Leukemia,* 13(11):18811892, 1999.

Beran, Estey, O'Brian, Cortes, Koller, Giles, Kornblau, Andreeff, Vey, Pierce, Hayes, Wong, Keating, Kantarijian, "Topotecan and cytarabine is an active combination regimen in myelodysplastic syndromes and chronic myelomonocytic leukemia," *J. Clinical Oncology,* 17(9): 2819-2830, 1999.

Boldin, Goncharov, Goltsev, Wallach, Involvement of MACH, a novel MORT 1/FADD-interacting protease, in Fas/APO-1- and TNF receptorinduced cell death," *Cell,* 85(6):803-815, 1996.

Brun, Tontonoz, Forman, Egis, Chen, Evans, Spiegelman, Differential activation of adipogenesis by multiple PPAR isoforms," *Genes Dev,* 10(8):974-984, 1996.

Carter, Algiers, Andreeff, "Expression of survivin, a member of the inhibitor of apoptosis (IAP) family of caspase inhibitors is expressed in AML and regulated by cytokines and ATRA," *Blood,* 94(Sappy 1), 1999.

Castaigne, Chomienne, Daniel, Ballerina, Bergen, Fenaux, Degas, "All-trans resinoid acid as a differentiation therapy for acute promyelocytic leukemia," *Blood,* 76(9):1704-1709, 1990.

Chakravarti, LaMorte, Nelson, Nakajima, Schulman, Juguilon, Montminy, Evans, "Role of CBP/P300 in nuclear receptor signalling, *Nature,* 383(659S):99-103, 1996.

Chou and Talalay, "Quantitative analysis of dose-effect relationships: the combined effects of multiple drugs or enzyme inhibitors," *Adv Enzyme Regal.,* 22:27-55:27-55, 1984.

Deveraux, Roy, Stennicke, Van Arsdale, Zhou, Srinivasula, Alnemri, Salvesen, Reed, "IAPS block apoptotic events induced by caspase-8 and cytochrome c by direct inhibition of distinct campuses," *EMBO J,* 17(8):2215-2223, 1998.

Deveraux, Takahashi, Salvesen, Reed, "X-linked IAP is a direct inhibitor of cell-death pretestes," *Nature,* 388(6639): 300-304, 1997.

Drach, Lopez-Berestein, McQueen, Andreeff, Mehta, "Induction of differation in myeloid leukemia cell lines and acute promyelocytic leukemia cells by liposomal all-trans-retinoic acid," *Cancer Research,* 53:2100-2102, 1993.

Estey, Giles, Kantarjian, O'Brien, Cortes, Freireich, LopezBerestein, Keating, "Molecular remissions induced by liposomal-encapsulated all-trans resinoid acid in newly diagnosed acute promyelocytic leukemia," *Blood,* 94:2230-2235, 1999. Pfahl M, Apfel R, Bendik I, Fanjul A, Graupner G, Lee M O, La Vista N, Lu X P, Estey, Thall, Pierce, Cortex, Beran, Kantarjian, Keating, Andreeff, Freireich, "Randomized phase II study of fludarabine+cytosine arabinoside+idarubicin+all-trans retinoic acid+granulocyte-colony stimulating factor in poor prognosis newly-diagnosed non-APL, AML and MDS, Blood, 1998.

Evans, "The steroid and thyroid hormone receptor superfamily," *Science,* 240(4854):889-895, 1988.

Fanjul, Delia, Pierotti, Rideout, Yu, Pfahl, Qiu, "4-Hydroxyphenyl retinamide is a highly selective activator of resinoid receptors," *J Biol Chem,* 271(37):22441-22446, 1996.

Forman, Chen, Evans, "Hypolipidemic drugs, polyunsaturated fatty acids, and eicosanoids are ligands for peroxisome proliferator-activated receptors alpha and delta," Proc Natl Acad Sci USA, 94(9):4312-43 17, 1997.

Forman, Tontonoz, Chen, Brun, Spiegelman, Evans, 15-Deoxy-delta 12, 14-prostaglandin J2 is a ligand for the adipocyte determination factor PPAR gamma," *Cell,* 83(5): 803-812, 1995.

Friesen, Herr, Krammer, Debatin, "Involvement of the CD95 (APO1/FAS) receptor/ligand system in drug-induced apoptosis in leukemia cells," *Nature Med,* 2(5):574-577, 1996.

Friesen, Herr, Krammer, Debatin, "Involvement of the CD95 (Apo1/Fas) receptor/ligand system in drug-induced apoptosis in leukemia cells," *Nature Med,* 2(5):574-577, 1996.

Gliniak B, Le T, "Tumor necrosis factor-related apoptosis-inducing ligand's antitumor activity in vivo is enhanced by the chemotherapeutic agent CPT-11", *Cancer Research* 59, 6153-6258, 1999.

Greenberg, Advani, Tallman, Letendre, Saba, Dugan, Lee, Lum, Sikic, Paietta, Bennett, Rowe, "Treatment of refractory/relapsed AML with PSC833 plus mitoxantrone, etoposide, cytarabine (PSC-MEC) vs. MEC, randomized phase III trial (E2995)," *Blood,* 94(1):383a, 1999.

Greene, Blumberg, McBride, Yi, Kronquist, Kwan, Hsieh, Greene, Nimer, "Isolation of the human peroxisome proliferator activated receptor gamma cDNA: expression in hematopoietic cells and chromosomes mapping," *Gene Expr,* 4(4-5):281-299, 1995.

Heyman, Mangelsdorf, Dyck, Stein, Eichele, Evans, Thaller, "9-cis resinoid acid is a high affinity ligand for the resinoid X receptor," *Cell,* 63(2):397-406, 1992.

Jiang, Ting, Seed, "PPAR-gamma agonists inhibit production of monocyte inflammatory cytokines," *Nature,* 391(6662): 82-86, 1998.

Johansson, Billstrom, Kristoffersson, Akerman, Garmcz, Ahlgren, Maim, Mitelman, "Deletion of chromosome arm 3p in hematologic malignancies," *Leukemia,* 11(8):1207-1213, 1997.

Jurgensmeier, Xie, Deveraux, Ellerby, Bredesen, Reed, "Bax directly induces release of cytochrome c from isolated mitochondria," *Proc Natl Acad Sci USA,* 95(9):4997-5002, 1998.

Keenan, Sato, Marvin, Lander, Gilmour, Mitchell, "IS-Deoxy-Delta(12,14)-prostaglandin J(2), a ligand for peroxisome proliferator-activated receptor-gamma, induces apoptosis in JEG3 choriocarcinoma cells," *Biochem Biophys Res Common,* 262(3):579-585, 1999.

Khmer, Xu, Heinzel, Torchia, Kurokawa, Gloss, Lin, Heyman, Rose, Glass, Rosenfeld, "A CBP integrator complex mediates transcription's activation and AP-1 inhibition by nuclear receptors," *Cell,* 85(3):403-414, 1996.

Kim, Lotan, Yue, Sporn, Suh, Gribble, Honda, Hong, Sun, "Capasase-3 activation is involved in apoptosis induced by a synthetic triterpenoid in Non-small cell lung cancer (NSCLC) cells," *Proc. Amer. Assoc. Cancer Res.,* 2000

Kitamura, Miyazaki, Shinomura, Kinds, Kanayama, Matsuzawa, "Peroxisome proliferator-activated receptor gamma induces growth arrest and differentiation markers of human colon cancer cells," *Jpn J Cancer Res,* 90(1):75-80, 1999.

Kliewer, Forman, Blumberg, Ong, Borgmeyer, Mangelsdorf, Umesono, Evans, "Differential expression and activation of a family of murine peroxisome proliferator-activated receptors," *Proc Natl Acad Sci USA,* 91(15):7355-7359, 1994.

Kliewer, Lenhard, Willson, Patel, Morris, Lehmann, "A prostaglandin J2 metabolite binds peroxisome proliferator-activated receptor gamma and promotes adipocyte differentiation," *Cell,* 83(5): 813-819, 1995.

Kliewer, Umesono, Norman, Heyman, Evans, "Convergence of 9-cos resinoid acid and peroxisome proliferator signalling pathways through heterodimer formation of their receptors," *Nature,* 358(63 89):771-774, 1992.

Kluck, Bossy-Wetzel, Green, Newmeyer, "The release of cytochrome c from mitochondria: A primary site for bcl-2 regulation of apoptosis," *Science,* 275(5303):1132-1136, 1997.

Kolitz, George, Hurd, Hoke, Dodge, Velez-Garcia, Powell, Moore, Caligiuri, Vardiman, Bloomfield, Larson, "Parallel Phase I trials of multi-drug resistance (MDR) modulation with PSC-833 (PSC) in untreated patients (pts) with acute myeloid leukemia (AML)<60 years old: preliminary results of CALGB 9621," *Blood,* 94(10:1):384a, 1999.

Konopleva and Andreeff, "Regulatory pathways in programmed cell death," *Cancer Mol Biol.,* 6:1229-1260, 1999.

Konopleva, Estrov, Stiouf, Chang, Zhao, Harris, Leysath, Xie, Jackson, Hong, Honda, Gribble, Place, Suh, Spom, Andreeff, "Novel synthetic triterpenoid, CDDO, and its methyl ester: Potent antiproliferative, proapoptotic and differentiating agents in AML," *Blood,* 94(Sappy 1), 1999.

Konopleva, Monaco, Zhao, Leysath, Estey, Belmont, Andreeff, "Engraftment potential of AML progenitors into NOD/scid mice is dependent on baseline CXCR4 expression," *Blood,* 94(Sappy 1). 1999.

Konopleva, Zhao, Xie, Segall, Youths, Claxton, Estrov, Komblau, Andreeff, "Apoptosis: molecules and mechanisms," *Adv Exp Med Biol,* 457:217-236, 1998.

Kornblau, Konopleva, Andreeff, Apoptosis regulating proteins as targets of therapy for hematological malignancies. *Exp. Opin. Inv. Drugs* 8:2027-2057, 1999.

Kornblau, Estey, Madden, Tran, Zhao, Consoli, Snell, Sanchez-Williams, Kantarjian, Keating, Newman, Andreeff, "Phase I study of mitoxantrone plus etoposide with multidrug blockage by SDZ PSC-833 in relapsed or refractory acute myelogenous leukemia," *J. Clin. Oncol.,* 15(5):1796-1802, 1997.

Kurokawa, DiRenzo, Boehm, Sugarman, Gloss, Rosenfeld, Heyman, Glass, "Regulation of resinoid signalling by receptor polarity and allosteric control of ligand binding," *Nature,* 371(6497):528-531, 1994.

Lapidot, Sirard, Vormoor, Murdoch, Hoang, Caceres-Cortes, Minden, Paterson, Caligiuri, Dick, "A cell initiating human acute myeloid leukaemia after transplantation into SCID mice," *Nature,* 367(6464):645-648, 1994.

Lehmann, Lenhard, Oliver, Ringold, Kliewer, "Peroxisome proliferator-activated receptors alpha and gamma are activated by indomethacin and other non-steroidal anti-inflammatory drugs," *J Biol Chem,* 272(6):3406-3410, 1997.

Lehmann, Moore, Smith-Oliver, Wilkison, Willson, Kliewer, "An antidiabetic thiazolidinedione is a high affinity ligand for peroxisome proliferator-activated receptor gamma (PPAR gamma)," *J Biol Chem,* 270(22): 12953-12956, 1995.

Leoni, Chao, Cottam, Gemini, Rosenbach, Carrara, Budihardjo, Wang, Carson, "Induction of an apoptotic program in cell-ftee extracts by 2-chloro-2'-deoxyadenosine 5'-triphosphate and cytochrome," *Proc Natl Acad Sci USA,* 95(16):9567-9571, 1998.

Liu, Yao, Kirschenbaum, Levine, "NS398, a selective cyclooxygenase-2 inhibitor, induces apoptosis and down-regulates bcl-2 expression in LNCaP cells," *Cancer Res,* 58(19):4245-4249, 1998.

Macho, Decaudin, Castedo, Hirsch, Susin, Zamzami, Kroemer, "Chloromethyl-X-Rosamine is an aldehyde-fixable potential-sensitive fluorochrome for the detection of early apoptosis," *Cytometry,* 25(4):333-340, 1996.

Mangelsdorf, Ong, Dyck, Evans, "Nuclear receptor that identifies a novel resinoid acid response pathway," *Nature,* 345(6272):224-229, 1990.

Matsuyama, Xu, Velours, Reed, "The Mitochondrial FOF1-ATPase proton pump is required for function of the proapoptotic protein Bax in yeast and mammalian cells," *Mol Cell,* 1(3):327-336, 1998.

Mehta, McQueen, Neamati, Collins, Andreeff, "Activation of resinoid receptors RAR alpha and RXR alpha induces differentiation and apoptosis, respectively, in HL-60 cells," *Cell, Growth Differ,* 7(2): 179-186, 1996.

Mueller, Sarraf, Tontonoz, Evans, Martin, Zhang, Fletcher, Singer, Spiegelman, Terminal differentiation of human breast cancer through PPAR gamma," *Mol Cell,* 1(3):465-470, 1998.

Mukherjee, Davies, Crumble, Bischoff, Cesario, Jow, Hamann, Boehm, Monday, Nadzan, Patemiti, Heyman, "Sensitization of diabetic and obese mice to insulin by resinoid X receptor agonists," *Nature,* 386(6623):407-410, 1997.

Mullet, Wilder, Bannasch, Israeli, Lehibach, Li-Weber, Friedman, Galle, Stremmel, Oren, Krammer, "ps3 activates the CD95 (APO1/Fas) gene in response to DNA damage by anticancer drugs," *J Exp Med,* 188(11):2033-204S, 1998.

Muzio, Chinnaiyan, Kischkel, O'Rourke, Shevchenko, Ni, Scaffidi, Brett, Zhang, Rentz, Rummer, Peter, Rixit, "FLICE, a novel FADD-homologous ICE/CED-3-like protease, is recruited to the CD95 (Fas/APO-1) death-inducing signaling complex," *Cell,* 85(6):817-827, 1996.

Nagy, Thomazy, Shipley, Fesus, Lymph, Heyman, Chandraratna, Davies, "Activation of resinoid X receptors induces apoptosis in HL-60 cell lines," *Mol Cell Biol,* 15(7):3540-3551, 1995.

Nagy, Thomazy, Shipley, Fesus, Lymph, Heyman, Chandraratna, Davies, "Activation of resinoid X receptors induces apoptosis in HL-60 cell lines," *Mol Cell Biol,* 15(7):3540-3551, 1995.

Nagy, Tontonoz, Alvarez, Chen, Evans, "Oxidized LDL regulates macrophage gene expression through ligand activation of PPARgamma," *Cell,* 93(2):229-240, 1998.

Nichols, Parks, Consler, Blanchard, "Development of a scintillation proximity assay for peroxisome proliferator-activated receptor gamma ligand binding domain," *Anal Biochem,* 257(2):112-119, 1998.

Nolte, Wisely, Weston, Cobb, Lambert, Kurokawa, Rosenfeld, Willson, Glass, Milbum, "Ligand binding and coactivator assembly of the peroxisome proliferator-activated receptor-gamma," *Nature,* 395(6698): 137-143, 1998.

Onate, Tsai, Tsai, O'Malley, "Sequence and characterization of a deactivator for the steroid hormone receptor superfamily," *Science,* 270(5240): 1354-1357, 1995.

Owen-Schaub, Radinsky, Kruzgl, Berry, Yonehara, "Anti-Fas on nonhematopoietic tumors: levels of Fas/APO-1 and bcl-2 are not predictive of biological responsiveness," *Cancer Res.,* 54(6):1580-1586, 1994.

Piedrafita and Ortiz, "Nuclear resinoid receptors and their mechanism of action," *Vitam. Horm.,* 49:327-82:327-382, 1994.

Ricote, Li, Willson, Kelly, Glass, "The peroxisome proliferator-activated receptor-gamma is a negative regulator of macrophage activation," *Nature,* 391(6662):79-82, 1998.

Robertson, Mueller, Collins, "Resinoid acid receptors in myeloid leukemia:
characterization of receptors in resinoid acid-resistant K-562 cells," *Blood,* 77(2):340-347, 1991.

Sarraf, Mueller, Smith, Wright, Kum, Aaltonen, de la, Spiegelman, Eng, "Loss-of-function mutations in PPAR gamma associated with human colon cancer," *Mol Cell,* 3(6):799-804, 1999.

Schadendorf D, Kern M A, Artuc M, Pahl H L, Rosenbach T, Fichtner I, Nurnberg W, Stuting S, von Stebut E, Worm M, Makki A, Jurgovsky K, Kolde G, Henz B M, "Treatment of melanoma cells with the synthetic retinoid CD437 induces apoptosis via activation of AP-1 in vitro, and causes growth inhibition in xenografts in vivo",*J. Cell Biol,* 135:1889-1898, 1996.

Suh, Wang, Honda, Gribble, Dmitrovsky,k Hickey, Maue, Place, Porter, Spinella, Williams, Wu, Dannenberg, Flanders, Letterio, Mangelsdorf, Nathan, Nguyen, Porter, Ren, Roberts, Roche, Subbaramaiah, Sporn, "A novel synthetic oleanane triterpenoid, 2-cyano-3, 12-dioxoolean-1, 9-dien-28-oic acid, with potent differentiating, antiproliferative, and anti-inflammatory activy," *Cancer Res.,* 59(2): 336-341, 1999.

Tamm, Segall, Kitada, Scudiero, Tudor, Myers, Monks, Andreeff, Reed, "Expression of IAP-family genes in human cancers and leukemias," *Blood,* Suppl. 1, 1999.

Tontonoz, Hu, Devine, Belle, Spiegelman, "PPAR gamma 2 regulates adipose expression of the phosphoenolpyruvate carboxykinase gene," *Mol Cell Biol,* 15(1):351-357, 1995.

Tontonoz, Hu, Graves, Budavari, Spiegelman, "mPPAR gamma 2: tissue-specific regulator of an adipocyte enhancer," *Genes Dev,* 8(10):12241234, 1994.

Tontonoz, Hu, Spiegelman, "Stimulation of adipogenesis in fibroblasts by PPAR gamma 2, a lipid-activated transcription factor, *Cell,* 79(7): 1147-1156, 1994.

Tontonoz, Nagy, Alvarez, Thomazy, Evans, "PPARgamma promotes monocyte/macrophage differentiation and uptake of oxidized LDL," *Cell,* 93(2):241-252, 1998.

Tontonoz, Singer, Forman, Sarraf, Fletcher, Fletcher, Brun, Mueller, Altiok, Oppenheim, Evans Spiegelman, "Terminal differentiation of human liposarcoma cells induced by ligands for peroxisome proliferator-activated receptor gamma and the resinoid X receptor," *Proc Natl Acad Sci USA,* 94(1):237-241, 1997.

Torchia, Rose, Inostroza, Khmer, Weston, Glass, Rosenfeld, "The transcription's coactivator p/CIP binds CBP and mediates nuclear-receptor function," *Nature,* 387(6634): 677-684, 1997.

Vargas et al., "Dystrophic cardiac calcinosis in C3H/HeN mice," *Lab. Anim. Sci.* 46:572-575, 1996.

Veiga, Keenan, Barata, Sallan, Nudger, Cardoso, "Peroxisome proliferator-activated receptor-gamma (PPAR gamma) expression by bone marrow endothelium reveals a potential target for therapeutic intervention in acute lymphoblastic leukemia," *Blood,* 94:10(1):627a. 1999.

Vermes, Haanen, Stiffens-Nakken, Reutelingsperger, "A novel assay for apoptosis. Flow cytometric detection of phosphatidylserine expression on early apoptotic cells using fluorescein labelled Annexin V," *J Immunol Methods,* 184(1):39-51, 1995.

Verna, Wang, Rao, Tang, Chen, Kramer, Grant, "Induction of apoptosis and differentiation by fludarabine in human leukemia cells (U937): interactions with the macrocyclic lactose bryostatin 1," *Leukemia,* 13(7):10461055, 1999.

Walczak H, Miller R E, Ariail K, Gliniak B, Griffith T S, Kubin M, Chin W, Jones J, Woodward A, Le T, Smith C, Smolak P, Goodwin R G, Rauch C T, Schuh J C, Lynch D H, "Tumoricidal activity of tumor necrosis factor-related apoptosis-inducing ligand in vivo", *Nature Medicine,* 5:157-163, 1999.

Wang Y, Porter W W, Suh N, Honda T, Gribble G W, Leesnitzer L M, Plunket K D, Mangelsdorf D J, Blanchard S G, Willson T M, Sporn M B: A synthetic triterpenoid, 2-cyano-3,12-dioxooleana-1,9-dien-28-oic acid (CDDO), is a ligand for the peroxisome proliferator-activated receptor gamma. Mol.Endocrinol. 14: 1550-1556, 2000.

Warrens, Frankel, Wilson, "Differentiation therapy of acute promyelocytic leukemia with tretinoin (all-trans-retinoic acid)," *N Engl J Med,* 324:1385-1393, 1991.

Wesselborg, Engulf, Rossmann, Los, Schultz-Osthoff, "Anticancer drugs induce caspase-8/FLICE activation and apoptosis in the absence of CD9S receptor/ligand interaction," *Blood,* 93(9):3053-3063, 1999.

Westin, Kurokawa, Nolte, Wisely, McInerney, Rose, Milbum, Rosenfeld, Glass, "Interactions controlling the assembly of nuclear receptor heterodimers and coactivators," *Nature,* 395(6698):199-202, 1998.

Willson, Cobb, Cowan, Wiethe, Cornea, Prakash, Beck, Moore, Kliewer, Lehmann, "The structure-activity relationship between peroxisome proliferator-activated receptor gamma egotism and the antihyperglycemic activity of thiazolidinediones," *J Med Chem,* 39(3):665-668, 1996.

Wu, Bucher, Farmer, "Induction of peroxisome proliferator-activated receptor gamma during the conversion of 3T3 fibroblasts into adipocytes is mediated by C/EBPbeta, C/EBPdelta, and glucocorticoids," *Mol Cell Biol,* 16(8): 4128-4136, 1996.

Xie, Zhao, Xu, McQueen, Andreeff, "Differential expression patterns in human myeloblastic leukemia HL-60 and multidrug resistant HL-60/Dox cells analyzed by human cDNA expression array," *Blood,* 92 (Sappy 1)[10], 387a. 1998.

Yang, Liu, Bhalla, Kim, Abrade, Cai, Peng, Jones, Wang, "Prevention of apoptosis by bcl-2: Release of cytochrome c from mitochondria blocked," *Science,* 275(S303):1129-1132, 1997.

Yang, Liu, Bhalla, Kim, Ibrado, Cai, Peng, Jones, Wang, "Prevention of apoptosis by Bcl-2: release of cytochrome c from mitochondria blocked," *Science,* 275(5303):1129-1132, 1997.

Zapata, Takahashi, Salvesen, Reed, "Granzyme release and caspase activation in activated human T-lymphocytes," *J Biol Chem,* 273(12):69166920, 1998.

What is claimed is:

1. A method for inducing cytotoxicity in a cancer cell comprising contacting said cell with 2-cyano-3,12-dioxoolean-1,9-dien-28-methyl ester (CDDO-Me) and a chemotherapeutic agent, wherein the CDDO-Me and the chemotherapeutic agent are provided in a combined amount effective to induce cytotoxicity in said cell.

2. The method of claim 1, wherein the CDDO-Me is contacted with said cancer cell prior to contacting said cell with said chemotherapeutic agent.

3. The method of claim 1, wherein said chemotherapeutic agent is contacted with said cell prior to contacting said cell with the CDDO-Me.

4. The method of claim 1, wherein said cancer cell is a leukemic cell.

5. The method of claim 4, wherein said leukemic cell is a blood cancer cell, a myeloid leukemia cell, a monocytic leukemia cell, a myelocytic leukemia cell, a promyelocytic leukemia cell, a myeloblastic leukemia cell, a lymphocytic leukemia cell, an acute myelogenous leukemic cell, a chronic myelogenous leukemic cell, a lymphoblastic leukemia cell, a hairy cell leukemia cell.

6. The method of claim 1, wherein said cancer cell is a solid tumor cell.

7. The method of claim 6, wherein said solid tumor cell is a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, a soft tissue cancer cell.

8. The method of claim 1, wherein said cancer cell is located in a human subject.

9. The method of claim 8, wherein said CDDO-Me is administered locally.

10. The method of claim 9, wherein said CDDO-Me is administered by direct intratumoral injection.

11. The method of claim 9, wherein said CDDO-Me is administered by injection into tumor vasculature.

12. The method of claim 8, wherein said CDDO-Me is administered systemically.

13. The method of claim 12, wherein the CDDO-Me is administered intravenously.

14. The method of claim 12, wherein the CDDO-Me is administered intra-arterially.

15. The method of claim 12, wherein the CDDO-Me is administered intra-peritoneally.

16. The method of claim 12, wherein the CDDO-Me is administered orally.

17. The method of claim 12, wherein the CDDO-Me is administered during ex vivo purging.

18. The method of claim 1, wherein said chemotherapeutic agent is doxorubicin, decitabine, daunorubicin, dactinomycin, mitoxantrone, cisplatin, procarbazine, mitomycin, carboplatin, bleomycin, etoposide, teniposide, mechlroethamine, cyclophosphamide, ifosfamide, melphalan, chlorambucil, ifosfamide, meiphalan, hexamethylmelamine, thiopeta, busulfan, carmustine, lomustine, semustine, streptozocin, dacarbazine, adriamycin, 5-fluorouracil (5FU), camptothecin, actinomycin-D, hydrogen peroxide , nitrosurea, plicomycin, tamoxifen, taxol, transplatinum, vincristin, vinblastin, TRAIL, dolastatin-10, bryostatin, annamycin, mylotarg, sodium phenylacetate, sodium butyrate, methotrexate, a cortocosteroid or tacrolimus.

19. The method of claim 1, wherein said chemotherapeutic agent is a retinoid.

20. The method of claim 19, wherein said retinoid is selected from the group consisting of all-trans-retinoic acid, 9-cis-retinoic acid, LG100268, LGD1069, fenretinide, and CD437.

21. The method of claim 20, wherein said retinoid is LG100268.

22. The method of claim 1, wherein said cell is contacted with the CDDO-Me a second time.

23. The method of claim 1, wherein said cell is contacted with said chemotherapeutic agent a second time.

24. The method of claim 1, wherein the CDDO-Me and said chemotherapeutic agent are contacted with said cell at the same time.

25. The method of claim 8, further comprising tumor resection.

26. The method of claim 25, wherein said tumor resection occurs prior to said contacting.

27. The method of claim 25, wherein said contacting comprises treating a resected tumor bed with the CDDO-Me and said chemotherapeutic agent.

28. The method of claim 25, wherein said tumor resection occurs after said contacting.

29. The method of claim 25, wherein said contacting occurs both before and after said tumor resection.

30. A method of killing a tumor cell comprising contacting said tumor cell with 2-cyano-3,12-dioxoolean-1,9-dien-28-methyl ester (CDDO-Me) and a chemotherapeutic agent, wherein said CDDO-Me and said chemotherapeutic agent are provided in a combined amount effective to kill said tumor cell.

31. The method of claim 30, wherein said chemotherapeutic agent is a retinoid.

32. A method of inducing apoptosis in a tumor cell comprising contacting said tumor cell with 2-cyano-3,12-dioxoolean-1,9-dien-28-methyl ester (CDDO-Me) and a chemotherapeutic agent, wherein said CDDO-Me and said chemotherapeutic agent are provided in a combined amount effective to induce apoptosis of said tumor cell.

33. The method of claim 32, wherein said chemotherapeutic agent is a retinoid.

34. A method of inducing differentiation in a tumor cell comprising contacting said tumor cell with a 2-cyano-3,12-dioxoolean-1,9-dien-28-methyl ester (CDDO)-Me and a chemotherapeutic agent, wherein said CDDO-Me and said chemotherapeutic agent are provided in a combined amount effective to induce the differentiation of said tumor cell.

35. The method of claim 34, wherein said chemotherapeutic agent is a retinoid.

36. A method of treating cancer in a human patient comprising administering 2-cyano-3,12-dioxoolean-1,9-dien-28-methyl ester (CDDO-Me) and a chemotherapeutic agent to said human patient, wherein said CDDO-Me and said chemotherapeutic agent are provided in a combined amount effective to treat said cancer.

37. The method of claim 36, wherein said chemotherapeutic agent is a retinoid.

38. A method of potentiating the effect of a chemotherapeutic agent on a tumor cell comprising contacting said tumor cell with 2-cyano-3,12-dioxoolean-1,9-dien-28-methyl ester (CDDO-Me) and the chemotherapeutic agent.

39. The method of claim 38, wherein said chemotherapeutic agent is a retinoid.

40. A method of inhibiting growth of a tumor cell comprising contacting said tumor cell with 2-cyano-3,12-dioxoolean-1,9-dien-28-methyl ester (CDDO-Me) and a chemotherapeutic agent wherein the CDDO-Me and the chemotherapeutic agent are provided in a combined amount effective to inhibit growth of said tumor cell.

41. The method of claim 40, wherein said chemotherapeutic agent is a retinoid.

42. A method of inducing apoptosis in a lymphoid cell that expresses Bcl-2 comprising contacting said lymphoid cell with 2-cyano-3,12-dioxoolean-1,9-dien-28-methyl ester (CDDO-Me) and an immunosupressive agent.

43. The method of claim 42, wherein the Bcl-2 is endogenous.

44. The method of claim 42, wherein the Bcl-2 is exogenous.

45. The method of claim 44, wherein the Bcl-2 is expressed by a expression vector that comprises a nucleic acid that encodes Bcl-2 under the control of a promoter active in the lymphoid cell.

46. The method of claim 42, wherein the lymphoid cell is a T-cell.

47. The method of claim 42, wherein the lymphoid cell is a cancer cell.

48. The method of claim 42, wherein the lymphoid cell is located in a human.

49. The method of claim 42, where the immunosuppressive agent is a corticosteroid.

50. The method of claim 42, where the immunosuppressive agent is a tacrolimus.

51. The method of claim 42, wherein the lymphoid cell is further contacted with a chemotherapeutic agent.

* * * * *

UNITED STATES PATENT AND TRADEMARK OFFICE
CERTIFICATE OF CORRECTION

PATENT NO. : 7,435,755 B2  Page 1 of 1
APPLICATION NO. : 09/998009
DATED : October 14, 2008
INVENTOR(S) : Marina Konopleva et al.

It is certified that error appears in the above-identified patent and that said Letters Patent is hereby corrected as shown below:

In claim 18, column 93, line 58, delete "meiphalan" and insert --melphalan-- therefor.

Signed and Sealed this

Thirtieth Day of December, 2008

JON W. DUDAS
*Director of the United States Patent and Trademark Office*

```
                      SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
caagatggat tgcacgcagg                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
gagcaaggtg agatgacagg                                                  20
```